(12) United States Patent
Poolman et al.

(10) Patent No.: US 9,567,377 B2
(45) Date of Patent: Feb. 14, 2017

(54) IMMUNOGENIC COMPOSITION

(75) Inventors: Jan Poolman, Rixensart (BE); Cindy Castado, Rixensart (BE); Vincent Weynants, Rixensart (BE); Nathalie Isabelle Devos, Rixensart (BE)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 13/583,314

(22) PCT Filed: Mar. 10, 2011

(86) PCT No.: PCT/EP2011/053632
§ 371 (c)(1),
(2), (4) Date: Sep. 7, 2012

(87) PCT Pub. No.: WO2011/110636
PCT Pub. Date: Sep. 15, 2011

(65) Prior Publication Data
US 2013/0045231 A1    Feb. 21, 2013

Related U.S. Application Data

(60) Provisional application No. 61/312,574, filed on Mar. 10, 2010, provisional application No. 61/312,550, filed on Mar. 10, 2010, provisional application No. 61/312,582, filed on Mar. 10, 2010, provisional application No. 61/312,792, filed on Mar. 11, 2010, provisional application No. 61/312,799, filed on Mar. 11, 2010, provisional application No. 61/312,804, filed on Mar. 11, 2010.

(51) Int. Cl.
*A61K 39/095* (2006.01)
*C12P 21/00* (2006.01)
*C07K 14/22* (2006.01)
*A61K 39/00* (2006.01)

(52) U.S. Cl.
CPC ............. *C07K 14/22* (2013.01); *A61K 39/095* (2013.01); *A61K 2039/60* (2013.01); *C07K 2319/00* (2013.01)

(58) Field of Classification Search
CPC ........... A61K 2039/55505; A61K 2039/55555; A61K 2039/55566; A61K 2039/60; A61K 39/00; A61K 39/095; C07K 14/22
See application file for complete search history.

(56) References Cited

U.S. PATENT DOCUMENTS 7,862,827 B2   1/2011  Giuliani et al.
2007/0031449 A1*  2/2007  Bos et al. ................. 424/203.1

FOREIGN PATENT DOCUMENTS

| WO | 2004/014418 | 2/2004 |
| WO | 2007/144316 | 12/2007 |
| WO | 2007/144317 | 12/2007 |
| WO | 2010/025964 | 3/2010 |
| WO | 2000/055327 | 9/2010 |
| WO | 2009/114485 | 9/2010 |

OTHER PUBLICATIONS

Zollinger, et al., (2010), Vaccine, vol. 28, No. 31, pp. 5057-5067.
Lewis, et al., (2009), Expert Review of Cawines, vol. 8, No. 6, pp. 729-745.
Michiel, et al., (2010), PLOS Pathogens, vol. 6, No. 7, pp. E1000969-1.
Harrison, et al., (2009), Vaccine, vol. 27, pp. B51-B63.
Kahler, et al. (1998), Critical Reviews in Microbiology, vol. 24, No. 4, pp. 281-334.
Jolley, et al., (2007), FEMS Microbiology Reviews, vol. 31, No. 1, pp. 89-96.
Moe, et al., (2001), Infection and Immunity, vol. 69, No. 6, pp. 3762-3771.
Vaughan, et al., (2006), Vaccine, vol. 24, No. 25, pp. 5277-5293.
Koeberling, et al., (2009), Clinical and Vaccine Immunology, vol. 16, No. 2, pp. 156-162.
Beernink, et al., (2008), Infection and Immunity, vol. 76, No. 6, pp. 2568-2575.
Beernink, et al., (2007), Journal of Infectious Diseases, vol. 195, No. 10, pp. 1472-1479.
Tan, et al., (2010), Journal of Infection, vol. 61, No. 6, pp. 516-517.
Koeberling, et al., (2008), Journal of Infectious Diseases, vol. 198, No. 2, pp. 262-270.
Schneider, et al., (2009), Nature, vol. 458, No. 7240, pp. 890-893.
Stork, et al., PLoS Pathog, 2013 9(10,:e1003733.
Stork, et al., PLoS, 2010, 6(7): e100969.
Van Ulsen P et al., FEMS Immuno & Med Microbiology, 2001, 32. pp. 53-64.
Bowe F et al., Infection and Immunity, 2004, 72, pp. 4052-4060.
Sjolinder H et al., Infection & Immunity, 2008, 76, pp. 5412-5420.
Turner PC et al., Microbiology, 2001, 147, pp. 1277-1290.

\* cited by examiner

*Primary Examiner* — Padma V Baskar
(74) *Attorney, Agent, or Firm* — Eric J. Kron

(57) ABSTRACT

Compositions for the treatment or prevention of Neisserial infection and methods for their use and manufacture are provided herein.

4 Claims, 2 Drawing Sheets

Figure 2
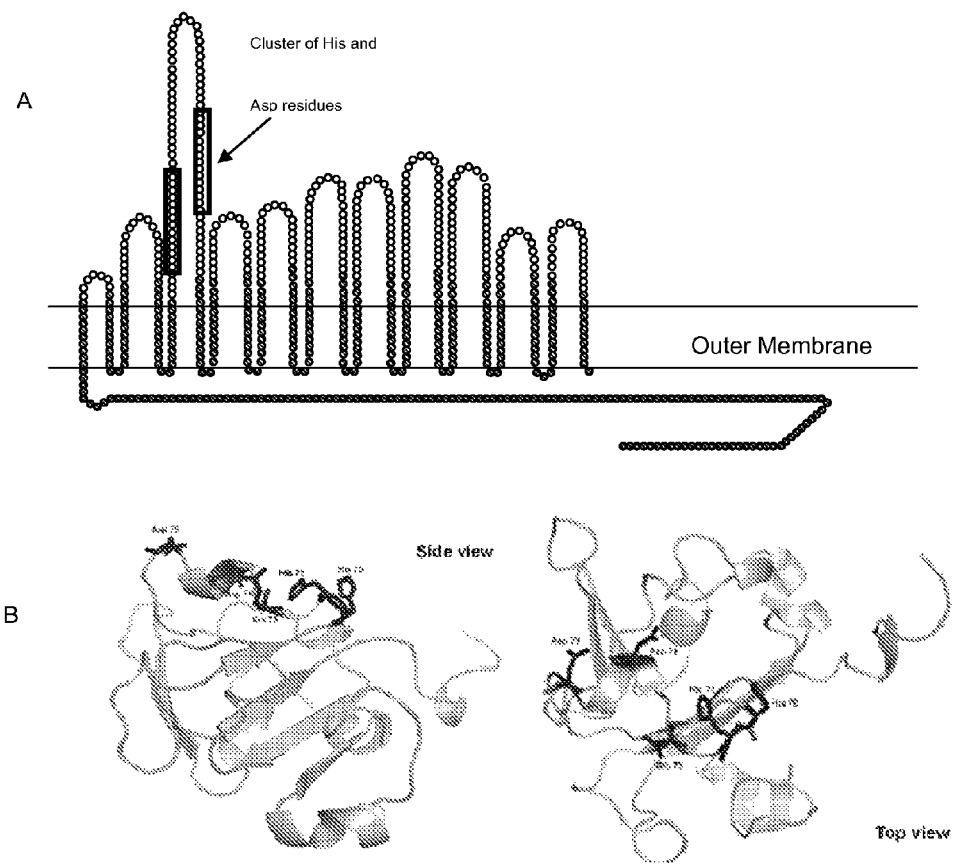
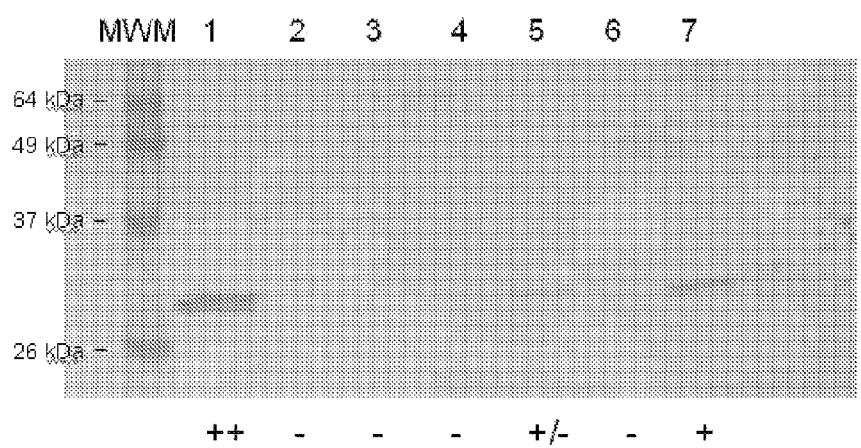
Strains: 1, M95-250687; 2, B16B6; 3, 2986; 4, 3356; 5, BZ232; 6, M05-0240072; 7, DE10427-05
Figure 3

IMMUNOGENIC COMPOSITION

This application is filed pursuant to 35 U.S.C. §371 as a United States National Phase Application of International Patent Application Serial No. PCT/EP2011/053632 filed Mar. 10, 2011, which claims priority from Provisional Application No. 61/312,574 filed Mar. 10, 2010, Provisional Application No. 61/312,550 filed Mar. 10, 2010, Provisional Application No. 61/312,582 filed Mar. 10, 2010, Provisional Application No. 61/312,792 filed Mar. 11, 2010, Provisional Application No. 61/312,799 filed Mar. 11, 2010 and Provisional Application No. 61/312,804 filed Mar. 11, 2010.

FIELD

The disclosure relates to the field of Neisserial immunogenic compositions and vaccines, their manufacture and the use of such compositions in medicine.

BACKGROUND

Neisserial strains of bacteria are the causative agents for a number of human pathologies, against which there is a need for effective vaccines to be developed. In particular *Neisseria gonorrhoeae* and *Neisseria meningitidis* cause pathologies which could be treated by vaccination.

*Neisseria meningitidis* is an important pathogen, particularly in children and young adults. Septicemia and meningitis are the most life-threatening forms of invasive meningococcal disease (IMD). This disease has become a worldwide health problem because of its high morbidity and mortality.

Thirteen *N. meningitidis* serogroups have been identified based on antigenic differences in the capsular polysaccharides, the most common being A, B and C which are responsible for 90% of disease worldwide. Serogroup B is the most common cause of meningococcal disease in Europe, USA and several countries in Latin America Vaccines based on the capsular polysaccharide of serogroups A, C, W and Y have been developed and have been shown to control outbreaks of meningococcal disease (Peltola et al 1985 Pediatrics 76; 91-96). However serogroup B is poorly immunogenic and induces only a transient antibody response of a predominantly IgM isotype (Ala'Aldeen D and Cartwright K 1996, J. Infect. 33; 153-157). There is therefore no broadly effective vaccine currently available against the serogroup B meningococcus which is responsible for the majority of disease in most temperate countries. This is particularly problematic since the incidence of serotype B disease is increasing in Europe, Australia and America, mostly in children under 5. The development of a vaccine against serogroup B meningococcus presents particular difficulties because the polysaccharide capsule is poorly immunogenic owing to its immunologic similarity to human neural cell adhesion molecule.

Strategies for vaccine production have therefore concentrated on the surface exposed structures of the meningococcal outer membrane but have been hampered by the marked variation in these antigens among strains.

One antigen contemplated for use in vaccines against *Neisseria meningitidis* is fHbp. Lewis et al discloses the status of fHbp as a vaccine candidate Expert Reviews Vaccines 8(6)$_{p729}$, (2009).

SUMMARY

The present disclosure relates to an immunogenic composition comprising:
(1) a first, fHbp, polypeptide antigen; and
(2) a second antigen capable of generating an antibody response against *Neisseria meningitidis* ST269
for prevention of Neisserial infection or disease.

In a further aspect the disclosure relates to a method of treatment or prevention of Neisserial infection or disease comprising administering to an individual in need thereof a protective dose of an immunogenic composition comprising:
(1) a first, fHbp, polypeptide antigen and
(2) a second antigen capable of generating an antibody response against *Neisseria meningitidis* ST269.

In a further aspect the disclosure relates to an immunogenic composition comprising (1) a first, fHbp, polypeptide antigen and (2) a second antigen capable of generating an antibody response against *Neisseria meningitidis* ST269.

In a further aspect the disclosure relates to use of
(1) a first, fHbp, polypeptide antigen and
(2) a second antigen capable of generating an antibody response against Neisserial meningitidis ST269
in the preparation of a medicament for prevention of infection or disease caused by *Neisseria* infection or disease.

In a further aspect the disclosure relates to a kit comprising
(1) a first, fHbp, polypeptide antigen and
(2) a second antigen capable of generating an antibody response against Neisserial meningitidis ST269

In a further aspect the disclosure relates to a method for the preparation for an immunogenic composition, the method comprising combining fHbp with a second antigen capable of generating an antibody response against *Neisseria meningitidis* ST269.

In a further aspect the disclosure relates to an immunogenic composition or method as described herein, wherein the second antigen is a TdfI or Hsf or Hap or TdfH.

In a further aspect the disclosure relates to an immunogenic composition or method as described herein wherein the composition is capable of preventing Neisserial meningitidis infection or disease caused by at least 70% of invasive MenB clonal complexes.

BRIEF DESCRIPTION OF THE DRAWINGS

FIG. 2 TdfI structure

FIG. 3—shows a Western-blot of whole-cells expressing different level of fHBP: high (line 1), intermediate (line 7), low (line 5) and non-detectable (lines 2, 3, 4, 6).

SEQUENCE IDENTIFIERS

Figure 1:
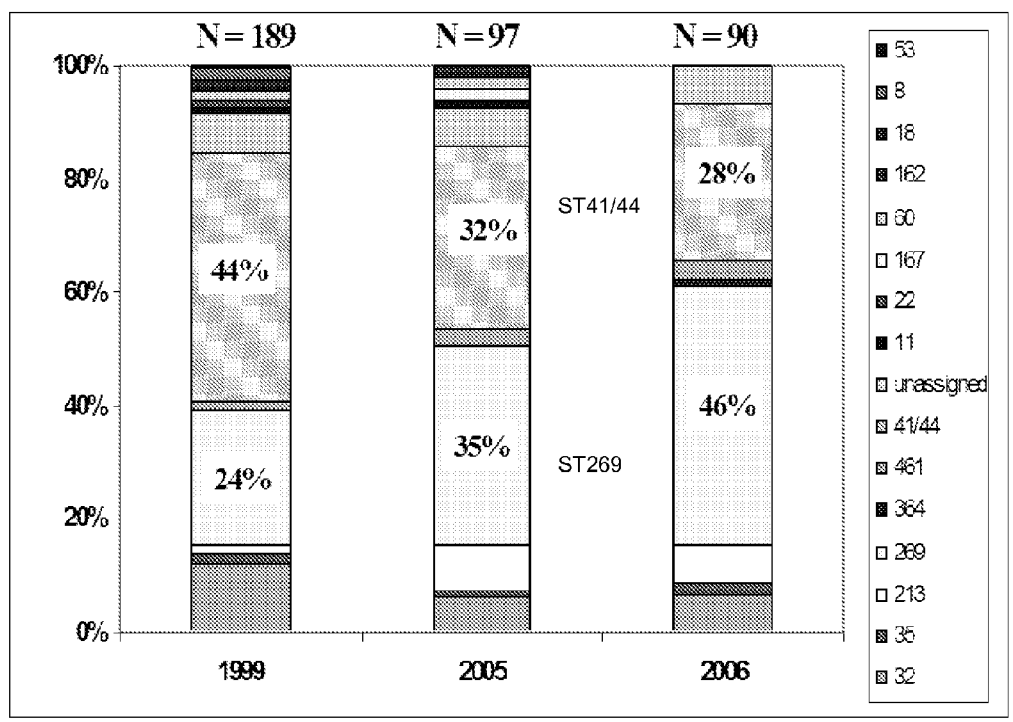
FIG. 1 Clonal complexes of serogroup B meningococcal case isolates submitted to the Health Protection Agency UK 1999-2006. An increase in ST269 cases can be seen.

The following sequence identifiers are included in the sequence listing and mentioned throughout the description:

SEQ ID NO: 1—amino acid residues 1 to 137 of the mature sequence of a family B fHbp protein SEQ ID NO: 2—amino acid residues 136 to 254 of the mature sequence of a family A fHbp protein SEQ ID NO: 3—consensus sequence from Family A over region 113-135

SEQ ID NO: 4—consensus sequence from Family B over region 113-135

SEQ ID NO: 5—mature Family B fHbp sequence from strain MC58

SEQ ID NO: 6—nucleic acid sequence for mature Family B fHbp sequence from strain MC58

SEQ ID NO: 7—mature Family A fHbp sequence from strain 8047

SEQ ID NO: 8—nucleic acid sequence for mature Family A fHbp sequence from strain 8047

SEQ ID NO: 9—amino acid 27 to 273 of full length fHbp sequence from strain 8047 with histidine tag (LVL489)

SEQ ID NO: 10—nucleic acid sequence for LVL489

SEQ ID NO: 11—amino acid 73 to 320 of full length fHbp sequence from strain MC58 with histidine tag (LVL 490)

SEQ ID NO: 12—nucleic acid sequence for LVL490

SEQ ID NO: 13—amino acid 66-72 of the full length Family B fHbp sequence

SEQ ID NO: 14—sequence of Histidine affinity tag

SEQ ID NO: 15—The peptide GENT (aa residues 136-139 in 8047 of family A and MC 58 of family B mature sequences) identical in family A and B SEQ ID NO: 16—amino acid sequence Fusion protein LVL491

SEQ ID NO: 17—nucleic acid sequence for LVL491

SEQ ID NO: 18—amino acid sequence of fusion protein A

SEQ ID NO: 19—nucleic acid sequence for fusion protein A

SEQ ID NO: 20—amino acid sequence of fusion protein B

SEQ ID NO: 21—nucleic acid sequence for fusion protein B

SEQ ID NO: 22—amino acid sequence of fusion protein C

SEQ ID NO: 23—nucleic acid sequence for fusion protein C

SEQ ID NO: 24—amino acid sequence of fusion protein E

SEQ ID NO: 25—nucleic acid sequence for fusion protein E

SEQ ID NO: 26—amino acids within positions 242-246 indicating Family A

SEQ ID NO: 27—amino acids within positions 242-246 indicating Family B

DETAILED DESCRIPTION

The present disclosure reveals the difficulty of achieving effective protection against sequence type ST269 strains utilizing Neisserial meningitidis fHbp protein alone, as described elsewhere herein. ST269 is a prevalent sequence type in the UK population, for example (see Journal of clinical microbiology 2009, page 3577-3585). The present disclosure provides fHbp vaccine compositions comprising an antigen effective against ST269, i.e. capable of providing protection against infection or disease caused an ST269 strain.

Sequence types are identified by Multilocus sequence typing (MLST), which characterises isolates of bacterial species using the sequences of internal fragments of seven house-keeping genes. For each house-keeping gene, the different sequences present within a bacterial species are assigned as distinct alleles and, for each isolate, the alleles at each of the seven loci define the allelic profile or sequence type (ST). Sequence types are grouped into clonal complexes by their similarity to a central allelic profile (genotype). For *Neisseria*, generally once a central genotype has been identified, clonal complexes are defined as including any ST that matches the central genotype at four or more loci unless it more closely matches another central genotype. Reference to Neisserial meningitidis ST269 or ST11 herein includes reference to Neisserial meningitidis ST269 or ST11 clonal complexes, respectively.

In some aspects, suitable immunogencic compositions of the disclosure are capable of protecting against infection or disease caused by >50%, suitably >60%, suitably >70%, suitably >80%, suitably >90% of *Neisseria meningitidis* B strains.

In some aspects, suitable immunogenic compositions of the disclosure are capable of protecting against infection or disease caused by >50%, suitably >60%, suitably >70%, suitably >80%, suitably >90% of the following group of *Neisseria meningitidis* B clonal complexes: ST41/44, ST269, ST213.

In one aspect is provided a full length fHBP polypeptide or fragment thereof, which is capable of eliciting antibodies against fHbp. Such fHbp may be a fusion polypeptide as disclosed in, for example, WO/2009/114485. The fHbp may be from any fHbp family. In one aspect an fHbp polypeptide is any polypeptide that comprises an epitope capable of eliciting antibodies against fHbp. fHBP is also referred to as as GNA1870 and lipoprotein 2086.

fHbp may be lipidated.

In one aspect the fHbp protein may be a chimaeric fHbp protein, comprising a fusion of amino acids from different fHbp proteins. The terms chimaeric fHbp protein and fHbp fusion protein are used interchangeably herein.

The present disclosure identifies 2 families of fHbp protein, A and B, and thus allows for the construction of chimaeric fHbp fusion proteins with sequences from 2 families, providing protection against *Neisseria meningitidis* infection or disease.

In a first aspect, the disclosure relates to a fusion protein comprising amino acid sequences F1 and F2, where F1 is a N-terminal fragment of a first fHbp amino acid sequence and F2 is a C-terminal fragment of a second fHbp amino acid sequence.

In one aspect the fusion protein comprises an F1 N-terminal fragment from fHbp Family B and F2 C-terminal fragment from fHbp Family A.

In one aspect F1 and F2 are at least 10 amino acids in length but suitably comprise 20 amino acids, suitably 30 amino acids, suitably 40 amino acids, suitably 50 amino acids, suitably 60 amino acids, suitably 70 amino acids, suitably 80 amino acids, suitably 90 amino acids, suitably 100 amino acids or suitably 110 amino acids, suitably taken contiguously from the amino acid sequence of an fHbp protein.

In one aspect the F1 and F2 fragments do not comprise overlapping sequences, when considered in respect of an alignment between the first and second fHbp family sequences.

In one aspect the fusion protein F1+F2 has a combined length of at least 200 amino acids, suitably at least 210, at least 220, at least 230, at least 240, at least 250 amino acids, and in one aspect is a full length FHBP protein of 254 amino acids.

The 2 parts, F1 and F2, of any fusion protein of the disclosure do not need to be directly linked, and may include a linker between F1 and F2. However, in one aspect, the F1 and F2 parts are directly linked.

Optionally the fusion protein may have additions, substitutions or deletions.

In one aspect both the F1 and F2 portions of the sequence comprise an immunogenic epitope.

In one aspect the F1 or F2 portion of the sequence contains epitopes suitable for generation of antibodies against family A and family B fHbp proteins.

In one aspect an N terminal fragment may be equivalent to, or part of, the 140 N-terminal amino acids of the mature sequence of a fHbp family B protein, suitably all or part of the N-terminal 135, 136, 137, 138 or 139 amino acids of the mature sequence of the fHbp protein.

Amino acid residues 1 to 137 of the mature sequence of a family B fHbp protein represent amino acid residues 66 to 202 of the full length family B fHbp sequence.

Suitable fragments are amino acid residues, 1 to 135, 1 to 136, 1 to 137, 1 to 138, 1 to 139, 8 to 135, 8 to 137 or 8 to 139 of the mature sequence of a family B fHbp protein. Residues 1 to 137 of the mature sequence are represented by strain MC58 of Family B shown in Seq ID No. 1 below or the equivalent regions of other strains of Family B.

In one aspect proteins in the same family have >80% identity based upon the sequence of fHbp starting from amino acid 136 of the mature protein to the C terminus.

In one aspect proteins in different families have 50-75% identity based upon the sequence of fHbp starting from amino acid 136 of the mature protein to the C terminus.

In one aspect the family identity is assessed over region 113-135.

In one aspect proteins in the same family have >69% identity based upon the region 113-135 of the mature amino acid sequence of fHbp.

In one aspect proteins in different families have <20% identity based upon the region 113-135 of the mature amino acid sequence of fHbp.

In one aspect Family A and B may be distinguished by the presence of one or more of the following amino acids:

SEQ ID No. 1:
CSSGGGGVAADIGAGLADALTAPLDHKDKGLQSLTLDQSVRKNEKLKLAAQGAEKTYGNGDSL

NTGKLKNKVSRFDFIRQIEVDGQLITLESGEFQVYKQSHSALTAFQTEQIQDSEHSGKMVAKRQF

RIGDIAGE

In one aspect, one or more of the first seven amino acids of the mature sequence of the F1 N terminal fragment are replaced by a histidine tag, or other affinity tag, to facilitate purification. In a further aspect a histidine tag, or other affinity tag, is added to the N terminus of the mature protein to facilitate purification.

In one aspect a C-terminal fragment is equivalent to, or part of, amino acids 130-254 of the mature fHbp sequence of a family A fHbp protein, suitably all or part of amino acids 136-254, 137-254, 138-254, 139-254, or 140 to 254 of the mature sequence.

Amino acid residues 136 to 254 of the mature sequence of a family A fHbp protein represent amino acid residues 155 to 273 of the full length family A fHbp sequence.

Some suitable fragments are amino acid residues 136 to 254, 137-254, 138 to 254, 139-254, or 140 to 254 of the mature sequence of a family A fHbp protein. Residues 136 to 254 of the mature sequence are represented by strain 8047 of Family A shown in Seq ID No. 2 below or the equivalent regions of other strains of Family A.

| AA position | Family A | Family B |
|---|---|---|
| 98 | I | V |
| 102 | D/N | S |
| 106-107 | VV | LT |
| 111 | I | T |
| 140 | A | S |
| 142-143 | NQ | D/GK |
| 146 | No amino acid equivalent to position 146 in family B. | E/K |
| 149 | K | m/r/s |
| 151 | E | T |
| 153 | H | R |
| 155 | K | T |
| 158 | S | G |
| 186 | T | S |
| 197-198 | EL | D/YI |
| 200 | A | P |
| 204 | S | R/H |
| 209 | L | S |
| 211-213 | DTR | SVL |
| 215-217 | GG/SE | NQA/D |

SEQ ID No. 2:
GEHTA FNQLPDGKAE YHGKAFSSDD AGGKLTYTID FAAKQGHGKI EHLKTPEQNV

ELAAAELKADEKSHAVILGDTRYGSEEKGTYHLALFGDRAQEIAGSATVK IGEKVHEIGIAGKQ

Amino acid residues GENT are conserved among family A and B (aa residues 136-139 in 8047 of family A and MC 58 of family B) and can therefore be included in the amino acid sequence from either family.

FHbp proteins are defined into two families, A and B, herein.

In one aspect the family classification is disclosed in "Sequence Diversity of the Factor H Binding Protein Vaccine Candidate in Epidemiologically Relevant Strains of Serogroup B *Neisseria meningitides*. The Journal of infectious diseases 2009, vol. 200, n°3, pp. 379-389"

In one aspect the family identity is assessed over region 136-254.

-continued

| AA position | Family A | Family B |
|---|---|---|
| 221 | T | S |
| 223 | H | S |
| 225-226 | AL | GI |
| 229-230 | DR | GK/Q |
| 234 | I | V |
| 239 | T | E |
| 242-246 | IG/REKV (SEQ ID NO. 26) | TA/VNGI (SEQ ID NO. 27) |
| 248 | E | H |

| AA position | Family A | Family B |
|---|---|---|
| 251 | I | L |
| 253 | G | A |

In one aspect family A and B comprises the following consensus sequence from region 113-135:

(SEQ ID NO. 3)
A KINNPDK(I/T)DSLIN(Q/R)RSFLVSGLG (SEQ ID NO. 4)
B Q(V/I/E)QD(S/P)E(D/H)S(G/R)(K/S)MVAKR(Q/R)F(R/K)IGDI(A/V)

An example of a family B sequence (SEQ ID NO. 5) is strain MC58:

1 CSSGGGGVAA DIGAGLADAL TAPLDHKDKG LQSLTLDQSV RKNEKLKLAA

51 QGAEKTYGNG DSLNTGKLKN DKVSRFDFIR QIEVDGQLIT LESGEFQVYK

101 QSHSALTAFQ TEQIQDSEHS GKMVAKRQFR IGDIAGEHTS FDKLPEGGRA

151 TYRGTAFGSD DAGGKLTYTI DFAAKQGNGK IEHLKSPELN VDLAAADIKP

* *

201 DGKRHAVISG SVLYNQAEKG SYSLGIFGGK AQEVAGSAEV KTVNGIRHIG

251 LAAKQ

Amino acids identified within this sequence as being of potential importance include:

Gly121 and Lys122: residues essential for the binding of MAbs JAR3 and 5

Peptide Glu146→Arq149 and Arq204: residues essential for the binding of MAb502

Residues Pro145, Phe227, Gly228, Lys230 and Glu233: could potentially play a minor role in MAb502 recognition Glu218 and Glu239 (*): involved in factor H-binding Corresponding nucleic sequence (SEQ ID No. 6):

1 TGCAGCAGCG GAGGGGGTGG TGTCGCCGCC GACATCGGTG CGGGGCTTGC

51 CGATGCACTA ACCGCACCGC TCGACCATAA AGACAAAGGT TTGCAGTCTT

101 TGACGCTGGA TCAGTCCGTC AGGAAAAACG AGAAACTGAA GCTGGCGGCA

151 CAAGGTGCGG AAAAAACTTA TGGAAACGGT GACAGCCTCA ATACGGGCAA

201 ATTGAAGAAC GACAAGGTCA GCCGTTTCGA CTTTATCCGC CAAATCGAAG

251 TGGACGGGCA GCTCATTACC TTGGAGAGTG GAGAGTTCCA AGTATACAAA

301 CAAAGCCATT CCGCCTTAAC CGCCTTTCAG ACCGAGCAAA TACAAGATTC

351 GGAGCATTCC GGGAAGATGG TTGCGAAACG CCAGTTCAGA ATCGGCGACA

401 TAGCGGGCGA ACATACATCT TTTGACAAGC TTCCCGAAGG CGGCAGGGCG

451 ACATATCGCG GGACGGCGTT CGGTTCAGAC GATGCCGGCG GAAAACTGAC

501 CTACACCATA GATTTCGCCG CCAAGCAGGG AAACGGCAAA ATCGAACATT

551 TGAAATCGCC AGAACTCAAT GTCGACCTGG CCGCCGCCGA TATCAAGCCG

601 GATGGAAAAC GCCATGCCGT CATCAGCGGT TCCGTCCTTT ACAACCAAGC

651 CGAGAAAGGC AGTTACTCCC TCGGTATCTT TGGCGGAAAA GCCCAGGAAG

701 TTGCCGGCAG CGCGGAAGTG AAAACCGTAA ACGGCATACG CCATATCGGC

751 CTTGCCGCCA AGCAATAA

Other examples of family B species include strains H44/76, M982, M060240006, 03s-0408, and other examples will be well known to the skilled person.

An example of a family A sequence (SEQ ID NO. 7) is strain 8047:

```
  1 CSSGGGGVAA DIGARLADAL TAPLDHKDKS LQSLTLDQSV RKNEKLKLAA

51 QGAEKTYGNG DSLNTGKLKN DKVSRFDFIR QIEVDGQLIT LESGEFQIYK

101 QDHSAVVALQ IEKINNPDKI DSLINQRSFL VSGLGGEHTA FNQLPDGKAE

151 YHGKAFSSDD AGGKLTYTID FAAKQGHGKI EHLKTPEQNV ELAAAELKAD
                    *                    *

201 EKSHAVILGD TRYGSEEKGT YHLALFGDRA QEIAGSATVK IGEKVHEIGI

251 AGKQ
```

Amino acids identified within this sequence as being of potential importance include:
Ala173: residue essential for the binding of MAb JAR11
Lys179 and Glu191: residues essential for the binding of MAb JAR10
Ser215: residue essential for the binding of MAb JAR13
Glu217 (*) and Glu238: involved in factor H-binding. Remark: the second glutamate could be replaced by a Thr238 (*) in some strains (it is the case in the strain 8047). These strains can also bind the factor H.

Corresponding nucleic sequence (SEQ ID NO. 8):

```
  1 TGCAGCAGCG GAGGCGGCGG TGTCGCCGCC GACATCGGCG CGAGGCTTGC

51 CGATGCACTA ACCGCACCGC TCGACCATAA AGACAAAAGT TTGCAGTCTT

101 TGACGCTGGA TCAGTCCGTC AGGAAAAACG AGAAACTGAA GCTGGCGGCA

151 CAAGGTGCGG AAAAAACTTA TGGAAACGGC GACAGCCTCA ATACGGGCAA

201 ATTGAAGAAC GACAAGGTCA GCCGCTTCGA CTTTATCCGT CAAATCGAAG

251 TGGACGGGCA GCTCATTACC TTGGAGAGCG GAGAGTTCCA AATATACAAA

301 CAGGACCACT CCGCCGTCGT TGCCCTACAG ATTGAAAAAA TCAACAACCC

351 CGACAAAATC GACAGCCTGA TAAACCAACG CTCCTTCCTT GTCAGCGGTT

401 TGGGCGGAGA ACATACCGCC TTCAACCAAC TGCCTGACGG CAAAGCCGAG

451 TATCACGGCA AAGCATTCAG CTCCGACGAT GCTGGCGGAA AACTGACCTA

501 TACCATAGAT TTCGCCGCCA AACAGGGACA CGGCAAAATC GAACACCTGA

551 AAACACCCGA GCAAAATGTC GAGCTTGCCG CCGCCGAACT CAAAGCAGAT

601 GAAAAATCAC ACGCCGTCAT TTTGGGCGAC ACGCGCTACG GCAGCGAAGA

651 AAAAGGCACT TACCACCTCG CCCTTTTCGG CGACCGCGCC CAAGAAATCG

701 CCGGCTCGGC AACCGTGAAG ATAGGGGAAA AGGTTCACGA AATCGGCATC

751 GCCGGCAAAC AGTAG
```

Other examples of family A species include strains M1239, M981, M08_240117, M97252153, and other examples will be well known to the skilled person.

The fusion protein is suitably capable of eliciting antibodies against both family members A and B as defined herein. In one aspect the fusion protein is able to elicit neutralising antibodies, suitably in response to infection by N. meningitidis expressing family A or family B fHbp molecules.

Suitably the chimaeric protein, when administered at an effective dose, elicits a protective immune response against Neisserial infection, more suitably protective against N. meningitidis serogroup B infection.

In one aspect the fusion protein is immunologically reactive with antibodies generated against Neisserial full-length fHbp proteins or with antibodies generated by infection of a mammalian host with Neisseria.

In one aspect chimeric proteins are able to elicit the production of bactericidal antibodies mediating the complement killing of strains expressing either the fHbp A or fHbp B.

In one aspect the fusion protein of the disclosure has at least one at least one mutation to prevent or reduce Factor H binding.

In one aspect the mutation is a deletion, insertion or substitution. Factor H binding may be human factor H binding, for example as assessed by ELISA or surface plasmon resonance, as disclosed in M. C. Schneider et al., 2009 "Neisseria meningitidis recruits factor H using protein mimicry of host carbohydrates" Nature Letters.

In one aspect the mutation to prevent factor H binding is contained within the C-terminal F2 fragment, from amino acids 136-254 of fHbp.

In one aspect the mutation to prevent factor H binding comprises substituting at least one Glu to Ala in fHbp. In a further aspect the mutation to prevent factor H binding comprises substituting one or more of the following residues contained within an F2 fragment to prevent fHbp binding: Glu 217, Glu/Thr 238 of fHbp Family A; Glu 218, Glu 239 of fHbp Family B. In one aspect one or more of the residues are mutated to alanine.

Factor H binding may be assessed by ELISA. For example, fHbp poylpeptides (chimeric or not) may be coated on a microplate. After saturation and washes, purified human fH or recombinant human fH is incubated in microwells and binding to fHBP is revealed (after washes) via addition of rabbit antibodies directed against the human fH and subsequent incubation with anti-rabbit IgG conjugated to peroxidise.

In one aspect, where the F1 fragment is from family B, the F1 fragment comprises both Gly at position 121 and Lys at position 122, (numbering based on the $MC_{5-8}$ strain as a reference family B strain).

In one aspect the fusion protein is capable of binding to antibodies JAR3 or JARS In one aspect, where the F2 fragment is from family A, the F2 fragment comprises one, or more or all of the following amino acids (numbering based on the 8047 strain as a reference A strain): Ala 173; Ser 215; Lys 179 and Glu 191, and in one aspect comprises both Lys 179 and Glu 191. In one aspect the fusion protein is capable of binding to one or more of antibodies JAR10, JAR11, JAR13.

In one aspect, where the F2 fragment is from family A, the fusion protein being constructed to comprise one or more or all of the following amino acids replacing the naturally occurring amino acids: ala 217, optionally ala at position 238, Glu146, Gly inserted at position 146, after the glutamine (subsequent numbers being shifted by +1 with respect to the wild type 8047 sequence), Gly148, Arg149 and Arg204 (numbering based on the $MC_{5-8}$ strain as a reference family B strain). In one aspect the fusion protein is capable of binding to MAb502

In one aspect, where F2 fragment is from family A, then the fragment may comprises one or more or all of Pro 145, Phe 227, Gly 228, Lys 230 and Glu 233. In one aspect the fusion protein is capable of binding to MAb502.

Antibodies mentioned above are referred to in the following publications, herein fully incorporated by reference: P. T. Beernink and D. M. Granoff, 2008 "Bactericidal antibody induced by meningococcals recombinant chimeric factor H-binding protein vaccines" Inf. & Imm. vol. 76, p. 2568-2575; P. T. Beernink et al., 2008 "Fine antigenic specificity and cooperative bactericidal activity of monoclonal antibodies directed at the meningococcal vaccine candidate Factor H-binding protein" Inf. & Imm. vol. 76, p. 4232-4240; M. Scarselli et al., 2009 "Epitope mapping of a bactericidal monoclonal antibody against the factor H binding protein of *Neisseria meningitidis*" J. Mol. Biol. vol. 386, p. 97-108). In one aspect fHbp includes amino acids disclosed as being relevant for immunogenicity in any such publication.

In one aspect the chimaeric protein of the disclosure comprising one or more amino acid alterations as defined above, demonstrates an increase of the bactericidal titers against strains expressing fHbp compared to the chimeric proteins without these modifications.

In one aspect the fusion protein of the present disclosure comprises residues 1 to 135, 1 to 136, 1 to 137, 1 to 138 or 1 to 139 from a mature family B fHbp protein and residues 136 to 254, 137 to 254, 138 to 254, 139 to 254 or 140 to 254 of a mature family A fHbp protein, and is unable to bind to Factor H.

In one aspect the fusion protein of the present disclosure comprises residues 8 to 135, 8 to 136, 8 to 137, 8 to 138 or 8 to 139 from a mature family B fHbp protein, optionally with a histidine tag, and residues 136 to 254, 137 to 254, 138 to 254, 139 to 254 or 140 to 254 of a mature family A fHbp protein, and is unable to bind to Factor H.

In one aspect, one or more of the first seven amino acids from a mature family B fHbp protein are absent and may be replaced by a histidine tag, or other affinity tag, to facilitate purification. In such cases, the family B fHbp portion of the fusion protein starts at residue 2, 3, 4, 5, 6 or 7 of the mature sequence.

In one aspect the fusion polypeptide comprises residues 1 to 135, 1 to 136, 1 to 137, 1 to 138, or 1 to 139 from a family B fHbp protein, for example having the MC58 sequence, and residues 136 to 254, 137 to 254, 138 to 254, 139 to 254 or 140 to 254 of a family A fHbp protein, for example having the sequence of strain 8047, the fusion protein being constructed to comprise the following amino acids replacing the naturally occurring amino acids: Ala217, optionally Ala at position 238, Glu146, Gly inserted at position 146, after the glutamine (subsequent numbers being shifted by +1 with respect to the wild type 8047 sequence), Gly148, Arg149 and Arg204 of family B mature protein sequence from strain MC58. These amino acids are found in construct C exemplified below. In one aspect the fusion polypeptide additionally comprises one or more or all of pro 145, phe 227, gly 228, lys 230 and glu 233. These amino acids are found in construct E exemplified below.

In one aspect the fusion polypeptide is selected from fusion proteins LVL491 (SEQ ID NO. 16), A (SEQ ID NO. 18), B (SEQ ID NO. 20), C (SEQ ID NO. 22), D, E (SEQ ID NO. 24) or F as disclosed herein, particularly from fusion proteins A, B, C, and E.

The composition also comprises an antigen effective against infection or diseases caused by meningococcal bacteria within the ST269 clonal complex.

Reference to an immunogenic composition comprising both antigens herein is intended to encompass true combinations of different antigens for combined delivery, for example in the form of a single vaccine dose, as well as an immunogenic composition comprising both antigens for simultaneous delivery, or substantially simultaneous delivery (for example by an injection of each component on the same visit to a medical practitioner), as well as a sequential delivery of one antigen followed, after a time interval, with delivery of a second antigen. Thus the immunogenic composition of the disclosure may be unitary or comprise separable components for combined or sequential delivery, as appropriate.

The antigen capable of generating an antibody response against a *Neisseria meningitidis* ST269 may be any suitable antigen, suitably an antigen capable of generating an immune response which protects or ameliorates the infection or disease caused by infection with ST269.

In one aspect an antigen which is effective against ST269 is an antigen capable of protecting against infection or disease caused by >50%, >60%, >70%, >80%, >90% of *Neisseria meningitidis* ST269, more suitably substantially all of *Neisseria meningitidis* ST269 clonal types.

In one aspect the antigen is selected from TdfI, Hsf and Hap or a combination thereof, for instance selected from the group consisting of a combination of two or more of said antigens such as TdfI and Hap, TdfI and Hsf, Hap and Hsf, and TdfI and Hap and Hsf. These antigens are discussed in more detail below.

The composition may also comprise an antigen capable of generating an antibody response against a *Neisseria meningitidis* L2 immunotype. The inventors have found that the majority of L2 strains tested express fHbp at poor levels.

The antigen capable of generating an antibody response against a *Neisseria meningitidis* L2 immunotype may be any suitable antigen capable of generating an immune response which protects or ameliorates the infection or disease caused by infection by >50%, >60%, >70%, >80% or >90% of L2 immunotypes, suitably an antigen capable of generating an immune response which protects against or ameliorates the infection or disease caused by infection by the L2 immunotype.

In one aspect the antigen is one which is encoded or expressed by >50%, >60%, >70%, >80% or >90% of *Neisseria meningitidis* L2 immunotypes, more suitably substantially all of *Neisseria meningitidis* L2 immunotypes, and more suitably wherein the % expression is determined in respect of the strains circulating in a given country or region.

In one aspect the antigen is selected from L2 LOS, TdfI, Hsf or Hap, or is selected from the group consisting of a combination of two or more of said antigens such as L2 LOS and TdfI, L2 LOS and Hap, L2 LOS and Hsf, TdfI and Hap, TdfI and Hsf, Hap and Hsf, TdfI and Hap and Hsf, L2 LOS and TdfI and Hap, L2 LOS and TdfI and Hsf, and L2 LOS and Hap and Hsf. These antigens are discussed in more detail below.

The composition may also comprise an antigen capable of generating an antibody response against a *Neisseria meningitidis* ST11 clonal complex strain. The inventors have found that many L2 immunotype strains are from the ST11 clonal complex.

In one aspect of the disclosure the combination of the disclosure includes an antigen that is also effective against ST11, which reference includes the ST11 clonal complex. In one aspect the antigen effective against ST11 clonal complex is selected from L2 LOS, Hap, TdfI and Hsf (discussed in more detail below), or is selected from the group consisting of a combination of two or more of said antigens such as L2 LOS and TdfI, L2 LOS and Hap, L2 LOS and Hsf, TdfI and Hap, TdfI and Hsf, Hap and Hsf, TdfI and Hap and Hsf, L2 LOS and TdfI and Hap, L2 LOS and TdfI and Hsf, and L2 LOS and Hap and Hsf.

The antigen capable of generating an antibody response against a *Neisseria meningitidis* ST11 strain may be any suitable antigen, suitably an antigen capable of generating an immune response which protects or ameliorates the infection or disease caused by infection with ST11.

In one aspect an antigen which is effective against ST11 is an antigen capable of protecting against infection or disease caused by >50%, >60%, >70%, >80%, >90% of *Neisseria meningitidis* ST11, more suitably substantially all of *Neisseria meningitidis* ST11 clonal types.

Reference or claim to any specific antigen herein includes all deletion, insertion and substitution mutations of that antigen, or other specific variant of that antigen as described herein, or (where the antigen is a polypeptide) to polypeptides having 80% or more, suitably at least 85%, at least 90%, at least 95%, at least 96%, at least 97%, at least 98%, at least 99% identity to that polypeptide, suitably being immunogenic.

Hsf:

Hsf has a structure that is common to autotransporter proteins. For example, Hsf from *N. menigitidis* strain H44/76 consists of a signal sequence made up of amino acids 1-51, a head region at the amino terminus of the mature protein (amino acids 52-479) that is surface exposed and contains variable regions (amino acids 52-106, 121-124, 191-210 and 230-234), a neck region (amino acids 480-509), a hydrophobic alpha-helix region (amino acids 518-529) and an anchoring domain in which four transmembrane strands span the outer membrane (amino acids 539-591).

Although full length Hsf may be used in immunogenic compositions of the disclosure, various Hsf truncates and deletions may also be advantageously used depending on the type of vaccine.

Where Hsf is used in a subunit vaccine, in one aspect a portion of the soluble passenger domain is used; for instance the complete domain of amino acids 52 to 479, most suitably a conserved portion thereof, for instance the particularly advantageous sequence of amino acids 134 to 479. In one aspect forms of Hsf may be truncated so as to delete variable regions of the protein disclosed in WO01/55182.

In one aspect variants would include the deletion of one, two, three, four, or five variable regions as defined in WO01/55182. The above sequences and those described below, can be extended or truncated by up to 1, 3, 5, 7, 10 or 15 amino acids at either or both N or C termini.

In one aspect fragments of Hsf therefore include the entire head region of Hsf, suitably containing amino acids 52-473. Additional fragments of Hsf can include surface exposed regions of the head including one or more of the following amino acid sequences; 52-62, 76-93, 116-134, 147-157, 157-175, 199-211, 230-252, 252-270, 284-306, 328-338, 362-391, 408-418, 430-440 and 469-479.

Where Hsf is present in an outer membrane vesicle preparation, it may be expressed as the full-length protein or suitably as an advantageous variant made up of a fusion of amino acids 1-51 and 134-591 (yielding a mature outer membrane protein of amino acid sequence 134 to the C-terminus). In one aspect forms of Hsf may be truncated so as to delete variable regions of the protein disclosed in WO01/55182. In one aspect variants would include the deletion of one, two, three, four, or five variable regions as defined in WO01/55182. In one aspect the first and second variable regions are deleted.

In one aspect variants would delete residues from between amino acid sequence 52 through to 237 or 54 through to 237, more suitably deleting residues between amino acid 52 through to 133 or 55 through to 133. The mature protein would lack the signal peptide.

Hap:

Computer analysis of the Hap-like protein from *Neisseria meningitidis* reveals at least three structural domains. Considering the Hap-like sequence from strain H44/76 as a reference, Domain 1, comprising amino-acid 1 to 42, encodes a sec-dependant signal peptide characteristic of the auto-transporter family, Domain 2, comprising amino-acids 43 to 950, encode the passenger domain likely to be surface exposed and accessible to the immune system, Domain 3, comprising residues 951 to the C-terminus (1457), is predicted to encode a beta-strands likely to assemble into a barrel-like structure and to be anchored into the outer-membrane. Since domains 2 is likely to be surface-exposed, well conserved (more than 80% in all strain tested) and could be produced as subunit antigens in *E. coli*, it represents an interesting vaccine candidates. Since domains 2 and 3 are likely to be surface-exposed, are well conserved (Pizza et al. (2000), Science 287: 1816-1820), they represent interesting vaccine candidates. Domain 2 is known as the passenger domain.

Immunogenic compositions of the disclosure may comprise the full-length Hap protein, suitably incorporated into an OMV preparation. Immunogenic compositions of the disclosure may also comprise the passenger domain of Hap which in strain H44/76 is composed of amino acid residues 43-950, or the N-terminal fragment from residues 43-1178. These fragments of Hap would be particularly advantageously used in a subunit composition of the disclosure. The above sequence for the passenger domain of Hap (or N-terminal fragment) can be extended or truncated by up to 1, 3, 5, 7, 10, 15, 20, 25, or 30 amino acids at either or both N or C termini.

TdfI:

Neisserial antigen NMB0964 (NMB numbers refer to *Neisseria meningitidis* group B genome sequences available from www.neisseria.org) [known as NMA1161 in the *Neisseria meningitidis* group A genome of strain Z2491, and as BASB082 in WO 00/55327, and as ZnuD] is a conserved antigen throughout *neisseria* and can induce bactericidal antibodies against a range of neisserial strains. The inventors have found this antigen functions as a $Zn^{2+}$ receptor in the bacterium, and its expression is regulated by the level of $Zn^{2+}$ in the medium.

By the term NMB0964 polypeptide herein it includes the neisserial TdfI polypeptide (encoded by the tdfI gene) in general from any neisserial strain (the protein is so well conserved amongst neisserial strains its identity in any particular neisserial strain is readily ascertainable by persons skilled in the art). The term therefore includes the NMA1161 sequence, and the BASB082 polypeptide sequence (and all the Polypeptides of the Disclosure concerning the BASB082 polypeptide) of WO 00/55327. For instance the NMB0964 polypeptide of the disclosure will cover SEQ ID NO: 2 of WO00/55327 or polypeptides with more than 70, 80, 90 or 95% sequence identity with said SEQ ID NO:2, or polypeptides comprising immunogenic fragments of 7, 10, 12, 15 or 20 (or more) contiguous amino acids from said SEQ ID NO: 2 (in particular said immunogenic fragments being capable of eliciting—if necessary when coupled to a protein carrier—an immune response which can recognise said SEQ ID NO: 2). NMB0964 immunogenic fragment embodiments include those extracellular loop sequences shown in the topology diagram of FIG. 2 as applied to any given NMB0964 sequence. Said NMB0964 immunogenic fragment polypeptide sequences may have more than 70, 80, 90 or 95% sequence identity with said extracellular loop sequences (as defined in FIG. 2) from SEQ ID NO:2 of WO 00/55327, or may be polypeptides comprising immunogenic fragments of 7, 10, 12, 15 or 20 (or more) contiguous amino acids from said extracellular loop sequences (as defined in FIG. 2) from SEQ ID NO: 2 (in particular said immunogenic fragments being capable of eliciting—if necessary when coupled to a protein carrier—an immune response which can recognise said SEQ ID NO: 2) and are provided as NMB0964 polypeptides of the disclosure. Said NMB0964 immunogenic fragment polypeptide sequences may have more than 70, 80, 90, 95, 99 or 100% sequence identity with the sequence from the third extracellular loop sequence given in FIG. 2 (wherein optionally the 2 Cys residues should be conserved, and may or may not be disulphide linked), or may be polypeptides comprising immunogenic fragments of 7, 10, 12, 15 or 20 (or more) contiguous amino acids from said extracellular loop sequence (in particular said immunogenic fragments being capable of eliciting—if necessary when coupled to a protein carrier—an immune response which can recognise SEQ ID NO: 2 of WO00/55327) and are provided as NMB0964 polypeptides of the disclosure. In one embodiment the NMB0964 immunogenic fragment polypeptides are not full-length NMB0964 (mature sequence or with signal sequence) polypeptides.

In one aspect NMB0964 may be used as an isolated antigen in a subunit vaccine approach.

In another aspect the NMB0964 antigen may be used in the form of isolated outer membrane vesicles prepared from a *Neisseria* species bacterium, wherein the *Neisseria* species bacterium produces a level of a NMB0964 polypeptide sufficient to provide for production of a vesicle that, when administered to a subject, elicits anti-NMB0964 antibodies; and a pharmaceutically acceptable excipient.

This may be achieved due to the *Neisseria* species bacterium being genetically modified in NMB0964 polypeptide production by for instance: disrupting the functional expression of the Zur repressor (NMB1266)—a protein which switches off expression of NMB0964 in the presence of $Zn^{2+}$ in the medium; replacing the NMB0964 promoter with one that does not bind Zur, in particular with a stronger promoter than the endogenous NMB0964 promoter such as a lac promoter; or through using a medium low in $Zn^{2+}$ concentration—i.e. under 5, 4, 3, 2, 1, 0.9, 0.8, 0.7, 0.6, 0.5, 0.4, 0.3, 0.2, 0.1, 0.05 or 0.01 μM free $Zn^{2+}$—(such as Roswell Park Memorial Institute medium 1640 (RPMI) which has around 1.69 μM $Zn^{2+}$ by ICP-MS), or removing $Zn^{2+}$ in the medium, for instance using a known zinc chelator such as TPEN (N,N,N',N'-Tetrakis(2-pyridylmethyl)ethylenediamine)—enough should be added to the medium such that the expression of the NMB0964 is maximised.

The *Neisseria* species bacterium may be deficient in capsular polysaccharide, for instance through disruption of functional expression of the siaD gene. It may be disrupted in the functional expression of the msbB and/or htrB genes to detoxify the LOS in the outer membrane vesicle. It may be disrupted in the expression of one or more the following genes: PorA, PorB, OpA, OpC, PilC, or FrpB. It may be disrupted in the functional expression of the lgtB gene. Such disruption methods are described in WO 01/09350 and WO2004/014417. The *Neisseria* species bacterium may be of immunotype L2 or L3.

Methods for the preparation or isolation of outer membrane vesicles (also known as microvesicles or blebs) from Neisserial strains are well known in the art, and are described in WO 01/09350 and WO2004/014417, and also below. Typically outer membrane vesicles are isolated by extracting either without a detergent, or with 0-0.5, 0.02-0.4, 0.04-0.3, 0.06-0.2, or 0.08-0.15% detergent, for instance deoxycholate, e.g. with around or exactly 0.1% deoxycholate.

An OMV vaccine prepared either in specific culture conditions low in Zn2+, or from a mutant *N. meningitidis* strain engineered to either over-express NMB0964 or to remove the Zinc repression mechanism mediated through Zur, is enriched in NMB0964, and such OMVs may elicit good bactericidal antibody responses compared to OMVs which have not been prepared with these methods.

In one aspect the disclosure relates to an immunogenic composition comprising an isolated outer membrane vesicles prepared from a *Neisseria* species bacterium, wherein the *Neisseria* species bacterium produces a level of a NMB0964 polypeptide sufficient to provide for production of a vesicle that, when administered to a subject, elicits anti-NMB0964 antibodies; and a pharmaceutically acceptable excipient. The NMB0964 polypeptide may be endogenous to the *Neisseria* species bacterium. The *Neisseria* species bacterium may be genetically modified to contain a nucleic acid encoding an exogenous NMB0964 polypeptide.

The NMB0964 polypeptide may be expressed from an NMB0964 gene with an endogenous promoter. The *Neisseria* species bacterium may be genetically modified in NMB0964 polypeptide production. The *Neisseria* species bacterium may be genetically modified through the disruption of functional expression of the Zur repressor (NMB1266).

The *Neisseria* species bacterium may be genetically modified to provide for expression of a NMB0964 polypeptide from a heterologous promoter. The heterologous promoter in one aspect does not bind the Zur repressor. In one aspect the heterologous promoter is a stronger promoter in the Neisserial species bacterium than the non-repressed endogenous promoter of the NMB0964 gene. In one aspect the heterologous promoter is an IPTG-inducible lac promoter.

In one aspect the level of NMB0964 polypeptide produced by the *Neisseria* species bacterium is greater than that made by *N. meningitidis* strain H44/76 grown in tryptic soy broth (TSB). In one aspect level of NMB0964 polypeptide produced by the *Neisseria* species bacterium is the same or greater than that made by *N. meningitidis* strain H44/76 grown in Roswell Park Memorial Institute medium 1640 (RPMI). In one aspect the level of NMB0964 polypeptide produced by the *Neisseria* species bacterium is the same or greater than that made by *N. meningitidis* strain H44/76 grown in Roswell Park Memorial Institute medium 1640 (RPMI) with 1 μM TPEN (N,N,N',N'-Tetrakis(2-pyridylmethyl)ethylenediamine). In one aspect the level of NMB0964 polypeptide produced by the *Neisseria* species bacterium is the same or greater than that made by *N. meningitidis* strain H44/76 in a medium which has less than 5, 4, 3, 2, 1, 0.9, 0.8, 0.7, 0.6, 0.5, 0.4, 0.3, 0.2, 0.1, 0.05 or 0.01 μM free $Zn^{2+}$.

In one aspect the Neisserial species bacterium is *Neisseria meningitidis*, or *Neisseria meningitidis* serogroup B. In one aspect the *Neisseria* species bacterium is deficient in capsular polysaccharide. In one aspect the *Neisseria* species bacterium is deficient in capsular polysaccharide through disruption of functional expression of the siaD gene. In one aspect the *Neisseria* species bacterium is disrupted in the functional expression of the msbB and/or htrB genes. In one aspect the *Neisseria* species bacterium is disrupted in the expression of one or more the following genes: PorA, PorB, OpA, OpC, PDC, or FrpB. In one aspect the *Neisseria* species bacterium is disrupted in the functional expression of the IgtB gene. In one aspect wherein the *Neisseria* species bacterium is of immunotype L2 or L3.

In one aspect the outer membrane vesicles are isolated by extracting with 0-0.5, 0.02-0.4, 0.04-0.3, 0.06-0.2, or 0.08-0.15% detergent, for instance deoxycholate, e.g. with around or exactly 0.1% deoxycholate.

In one aspect the disclosure relates to a method of producing an immunogenic composition, the method comprising: culturing a *Neisseria* species bacterium producing a NMB0964 polypeptide, wherein the NMB0964 polypeptide is produced at a level sufficient to provide for production of outer membrane vesicles that, when administered to a subject, elicit anti-NMB0964 antibodies; preparing outer membrane vesicles from the cultured bacterium; and combining the outer membrane vesicles with a pharmaceutically acceptable excipient to produce an immunogenic composition suitable for administration to a subject in combination with an fHbp polypeptide. In one aspect the NMB0964 polypeptide is endogenous to the *Neisseria* species bacterium. In one aspect wherein the *Neisseria* species bacterium has been genetically modified to contain a nucleic acid encoding an exogenous NMB0964 polypeptide. In one aspect the NMB0964 polypeptide is expressed from an NMB0964 gene with an endogenous promoter. In one aspect the *Neisseria* species bacterium has been genetically modified in NMB0964 polypeptide production. In one aspect the Neisserial species bacterium has been genetically modified through the disruption of functional expression of the Zur repressor (NMB1266). In one aspect wherein the *Neisseria* species bacterium has been genetically modified to provide for expression of a NMB0964 polypeptide from a heterologous promoter. In one aspect the heterologous promoter does not bind the Zur repressor. In one aspect heterologous promoter is a stronger promoter in the Neisserial species bacterium than the non-repressed endogenous promoter of the NMB0964 gene. In one aspect the heterologous promoter is an IPTG-inducible lac promoter. In one aspect the level of NMB0964 polypeptide produced by the *Neisseria* species bacterium is greater than that made by *N. meningitidis* strain H44/76 grown in tryptic soy broth (TSB). In one aspect the level of NMB0964 polypeptide produced by the *Neisseria* species bacterium is the same or greater than that made by *N. meningitidis* strain H44/76 grown in Roswell Park Memorial Institute medium 1640 (RPMI). In one aspect the level of NMB0964 polypeptide produced by the *Neisseria* species bacterium is the same or greater than that made by *N. meningitidis* strain H44/76 grown in Roswell Park Memorial Institute medium 1640 (RPMI) with 1 μM TPEN (N,N,N',N'-Tetrakis(2-pyridylmethyl)ethylenediamine). In one aspect the level of NMB0964 polypeptide produced by the *Neisseria* species bacterium is the same or greater than that made by *N. meningitidis* strain H44/76 in a medium which has less than 5, 4, 3, 2, 1, 0.9, 0.8, 0.7, 0.6, 0.5, 0.4, 0.3, 0.2, 0.1, 0.05 or 0.01 μM free $Zn^{2+}$. In one aspect culturing of the *Neisseria* species bacterium is in a medium which has less than 5, 4, 3, 2, 1, 0.9, 0.8, 0.7, 0.6, 0.5, 0.4, 0.3, 0.2, 0.1, 0.05 or 0.01 μM free $Zn^{2+}$.

In one aspect culturing of the Neisserial species bacterium is in a medium comprising a $Zn^{2+}$ chelator. In one aspect $Zn^{2+}$ chelator is present in the medium at a concentration of 0.01-100, 0.1-10, 0.3-5, or 0.5-1 μM. In one aspect the $Zn^{2+}$ chelator present in the medium is TPEN. In one aspect the concentration of TPEN is between 1 and 50 μM, such as 1-30 μM.

In one aspect the step of preparing outer membrane vesicles is carried out by extracting with 0-0.5, 0.02-0.4, 0.04-0.3, 0.06-0.2, or 0.08-0.15% detergent, for instance deoxycholate, e.g. with around or exactly 0.1-0.5% deoxycholate. In one aspect the step of preparing outer membrane vesicles is carried out without use of a detergent.

In one aspect the fHbp polypeptide is combined with a peptide sequence sharing more than 50, 60, 70, 80, 90, 95, 99, or of 100% sequence identity with the following sequence: RDQYGLPAHSHEYDDCHADIIWQKSLINKRYLQLYPHLLTEEDIDYDNPGLSCGFHDDDN AHAHTHS, or a polypeptide comprising an immunogenic fragment of 7, 10, 12, 15 or 20 (or more) contiguous amino acids from said sequence (optionally wherein said peptide sequence or said immunogenic fragment is capable of eliciting—if necessary when coupled to a protein carrier—an immune response which can recognise SEQ ID NO: 2 of WO00/55327), and a pharmaceutically acceptable carrier. In one aspect the two Cys residues are present in the polypeptide, and may di-sulphide linked. In one aspect the polypeptide is not a full length mature NMB0964 polypeptide, or is not a full length NMB0964 polypeptide with signal sequence intact.

In one aspect the immunogenic composition comprises an antigen capable of generating an antibody response against a *Neisseria meningitidis* L2 immunotype. Such an antigen may be the L2 LOS.

LPS (lipopolysaccharide, also known as LOS-lipooligosaccharide) is the endotoxin on the outer membrane of *Neisseria*. The polysaccharide moiety of the LPS is known to induce bactericidal antibodies. The structure and function of Los is described inn Verheul Microbiological reviews, March 1993, Vol 57, no 1, p 34-49.

Heterogeneity within the oligosaccharide moiety of the LPS generates structural and antigenic diversity among different neisserial strains (Griffiss et al. Inf. Immun. 1987; 55: 1792-1800). This has been used to subdivide meningococcal strains into L2 immunotypes (Scholtan et al. J Med Microbiol 1994, 41:236-243). Immunotypes L3, L7, & L9 are immunologically and structurally similar (or even the same) and have therefore been designated L3, 7, 9 (or, for the purposes of this specification, generically as"L3"). Meningococcal LPS L3, 7, 9 (L3), L2 and L5 can be modified by sialylation, or by the addition of cytidine 5'-monophosphate-N-acetylneuraminic acid. See M. P. Jennings et al, Microbiology 1999, 145, 3013-3021 and Mol Microbiol 2002, 43: 931-43 for further illustration of LPS structure and heterogeneity.

L2 LOS defines the L2 immunotype and thus is a potential antigen to supplement an fHbp based vaccine.

L2 LOS suitably generates antibodies capable of killing a Neisserial L2 immunotype. In one aspect reference to L2 LOS herein includes L3V strains.

L2 LOS may be presented in an outer membrane vesicle (OMV—The term 'bleb' and 'outer membrane vesicle' are used interchangeably herein), suitably where the vesicle is extracted with a low percentage detergent, more suitably 0-0.5%, 0.02-0.4%, 0.04-0.3%, 0.06-0.2%, 0.08-0.15% or 0.1%, most suitably deoxycholate [DOC]) but may also be part of a subunit vaccine.

More generally, OMVs of the present disclosure may be extracted using a low percentage detergent, more suitably 0-0.5%, 0.02-0.4%, 0.04-0.3%, 0.06-0.2%, 0.08-0.15% or 0.1%, most suitably deoxycholate [DOC])

LOS may be used plain or conjugated to a source of T-cell epitopes such as tetanus toxoid, Diphtheria toxoid, CRM-197 or OMV outer membrane proteins.

L2 LOS may be detoxified.

Details of all such aspects are described in more detail below, in relation to the choice and preparation of LOS.

Where LPS, suitably meningococcal LPS, is included in a vaccine of the disclosure, suitably and advantageously either or both of immunotypes L2 and L3 are present.

In one aspect the second antigen is a meningococcal LPS having a least a PEA on position 6 on Hep II of inner core with or without a second PEA or a glucose on this Hep II.

Suitable other antigens that may be included in the immunogenic composition of the disclosure may be selected from categories of proteins including adhesins, autotransporter proteins, toxins, integral outer membrane proteins and Fe acquisition proteins.

In one aspect, the disclosure provides immunogenic compositions that comprise at least or exactly two, three, four, five, six, seven, eight, nine or ten different *Neisseria* antigens. Most suitably these antigens are selected from at least or exactly two, three, four or five groups of proteins selected from the following:

a Neisserial adhesion, optionally selected from the group consisting of FhaB, NspA PilC, MafA, MafB, Omp26, NMB 0315, NMB 0995, NMB 1119 and NadA;

a Neisserial autotransporter optionally selected from the group consisting of IgA protease, AspA, and NadA;

a Neisserial toxin optionally selected from the group consisting of FrpA, FrpC, FrpA/C, VapD, NM-ADPRT and either or both of LPS immunotype L2 and LPS immunotype L3;

a Neisserial Fe or zinc acquisition protein, or other metal acquisition protein, optionally selected from the group consisting of TbpA, TbpB, LbpA, LbpB, HpuA, HpuB, Lipo28 (GNA2132), Sibp, NMB0293, FbpA, Bcp, BfrA, BfrB and P2086 (XthA); and a Neisserial membrane-associated protein, suitably outer membrane protein, particularly integral outer membrane protein, optionally selected from the group consisting of PilQ, OMP85, FhaC, NspA, TbpA, LbpA, TspA, TspB, TdfH, PorB, MltA, HpuB, HimD, H isD, OstA, HlpA (GNA1946), NMB 1124, NMB 1162, NMB 1220, NMB 1313, NMB 1953, HtrA, and PldA (OmplA).

The antigens of the present disclosure are suitably isolated, meaning that they are altered by the hand of man. In one aspect they are purified to some degree, most suitably more than 40, 50, 60, 70, 80, 90, 95 or 99% pure (before combination with the other components of the immunogenic compositions of the disclosure).

Where a protein is specifically mentioned herein, it is suitably a reference to a native, full-length protein, and to its natural variants (i.e. to a native protein obtainable from a Neisserial, suitably meningococcal strain) but it may also encompass antigenic fragments thereof (particularly in the context of subunit vaccines). These are fragments (often specifically described herein) containing or comprising at least 15 amino acids, suitably at least 20 amino acids, at least 30 amino acids, at least 40 amino acids or at least 50 amino acids, taken contiguously from the amino acid sequence of the protein. Antigenic fragments may also be immunogenic fragments. It is further envisaged that reference to proteins and protein sequences herein includes a polypeptide comprising an immunogenic fragment of 7, 10, 12, 15, 20, 30, 40 or 50 (or more) contiguous amino acids from said protein sequence or from the amino acid sequence of said protein (optionally wherein said immunogenic fragment is capable of eliciting—if necessary when coupled to a protein carrier—an immune response which can recognise said protein or said protein sequence). In addition, antigenic fragments denotes fragments that are immunologically reactive with antibodies generated against the Neisserial full-length proteins or with antibodies generated by infection of a mammalian host with *Neisseria*. Antigenic fragments also includes fragments that when administered at an effective dose, elicit a protective immune response against Neisserial infection, more suitably it is protective against *N. meningitidis* and/or *N. gonorrhoeae* infection, most suitably it is protective against *N. meningitidis* serogroup B infection.

Also included are recombinant fusion proteins of Neisserial proteins, or fragments thereof. These may combine different Neisserial proteins or fragments thereof in the same polypeptide. Alternatively, the disclosure also includes individual fusion proteins of Neisserial proteins or fragments thereof, as a fusion protein with heterologous sequences such as a provider of T-cell epitopes or purification tags, for example: p-galactosidase, glutathione-S-transferase, green fluorescent proteins (GFP), epitope tags such as FLAG, myc tag, poly histidine, or viral surface proteins such as influenza virus haemagglutinin, tetanus toxoid, diphtheria toxoid, CRM197.

Antigens of the disclosure associated with NMB references (or GNA references) refer to known reference numbers corresponding to known sequences (well-known to a skilled person) which can (for example) be accessed from www.neisseria.org.

Details of the 5 classes of proteins mentioned above are included in WO/2004/014418, hereby incorporated fully by reference.

1. Adhesins include FhaB (WO98/02547), NadA (J. Exp. Med. (2002) 195: 1445; NMB 1994), Hsf also known as NhhA (NMB 0992) (WO99/31132) as mentioned above, Hap (NMB 1985) (WO99/55873) as mentioned above, NspA (WO96/29412), MafA (NMB 0652) and MafB (NMB 0643) (Annu Rev Cell Dev Biol. 16; 423-457 (2000); Nature Biotech 20; 914-921 (2002)), Omp26 (NMB 0181), NMB 0315, NMB 0995, NMB 1119 and PDC (Mol. Microbiol. 1997, 23; 879-892). These are proteins that are involved in the binding of Neisseria to the surface of host cells. Hsf is an example of an adhesin, as well as being an autotranporter protein. Immunogenic compositions of the disclosure may therefore include combinations of Hsf and other autotransporter proteins where Hsf contributes in its capacity as an adhesin. These adhesins may be derived from Neisseria meningitidis or Neisseria gonorrhoeae or other Neiserial strains. The disclosure also includes other adhesins from Neisseria.

FhaB This antigen has been described in WO98/02547 SEQ ID NO 38 (nucleotides 3083-9025)—see also NMB0497. The present inventors have found FhaB to be particularly effectively at inducing anti-adhesive antibodies alone and in particular with other antigens of the disclosure. Although full length FhaB could be used, the inventors have found that particular C-terminal truncates are surprisingly at least as effective and suitably even more effective in terms of cross-strain effect. Such truncates have also been advantageously shown to be far easier to clone. FhaB truncates of the disclosure typically correspond to the N-terminal two-thirds of the FhaB molecule, suitably the new C-terminus being situated at position 1200-1600, more suitably at position 1300-1500, and most suitably at position 1430-1440. Specific embodiments have the C-terminus at 1433 or 1436. Accordingly such FhaB truncates of the disclosure and vaccines comprising such truncates are independent aspects of the present disclosure as well as being components of the combination immunogenic compositions of the disclosure. The N-terminus may also be truncated by up to 10, 20, 30, 40 or 50 amino acids.

2. Autotransporter Proteins: Autotransporter proteins typically are made up of a signal sequence, a passenger domain and an anchoring domain for attachment to the outer membrane. Examples of autotransporter proteins include Hsf (WO99/31132) (NMB 0992) as mentioned above, HMW, Hia (van Ulsen et al Immunol. Med. Microbiol. 2001 32; 53-64), Hap (NMB 1985) (WO99/55873; van Ulsen et al Immunol. Med. Microbiol. 2001 32; 53-64) as mentioned above, UspA, UspA2, NadA (NMB 1994) (Comanducci et al J. Exp. Med. 2002 195; 1445-1454), AspA (Infection and Immunity 2002, 70 (8); 4447-4461; NMB 1029), Aida-1 like protein, SSh-2 and Tsh. NadA (J. Exp. Med. (2002) 195: 1445) is another example of an autotransporter proteins, as well as being an adhesin. Immunogenic compositions of the disclosure may therefore include combinations of NadA and adhesins where NadA contributes in its capacity as an autotransporter protein. These proteins may be derived from Neisseria meningitidis or Neisseria gonorrhoeae or other Neiserial strians. The disclosure also includes other auto-transporter proteins from Neisseria.

3. Iron and zinc, and other metal acquisition proteins include TdfI (as mentioned above, see Done J et al Microbiology 2003, Turner P C et al Microbiology 2001—add full references), TbpA (NMB 0461) (WO92/03467, U.S. Pat. No. 5,912,336, WO93/06861 and EP586266), TbpB (NMB 0460) (WO93/06861 and EP586266), LbpA (NMB 1540) (Med Microbiol (1999) 32: 1117), LbpB (NMB 1541) (WO/99/09176), HpuA (U73112. 2) (Mol. Microbiol. 1997, 23; 737-749), HpuB (NC_003116. 1) (Mol. Microbiol. 1997, 23; 737-749), P2086 also known as XthA (NMB 0399) (13'''International Pathogenic Neisseria Conference 2002), FbpA (NMB 0634), FbpB, BfrA (NMB 1207), BfrB (NMB 1206), Lipo28 also known as GNA2132 (NMB 2132), Sibp (NMB 1882), HmbR, HemH, Bcp (NMB 0750), Iron (III) ABC transporter-permease protein (Tettelin et al Science 287; 1809-1815 2000), Iron (III) ABC transporter-periplasmic (Tettelin et al Science 287; 1809-1815 2000), TonB-dependent receptor (NMB 0964 and NMB 0293) (Tettelin et al Science 287; 1809-1815 2000) and transferrin binding protein related protein (Tettelin et al Science 287; 1809-1815 2000). These proteins may be derived from Neisseria meningitidis, Neisseria gonorrhoeae or other Neisserial strains. The disclosure also includes other iron aquisition proteins from Neisseria.

TbpA interacts with TbpB to form a protein complex on the outer membrane of Neisseria, which binds transferrin. Structurally, TbpA contains an intracellular N-terminal domain with a TonB box and plug domain, multiple transmembrane beta strands linked by short intracellular and longer extracellular loops.

Two families of TbpB have been distinguished, having a high molecular weight and a low molecular weight respectively. High and low molecular weight forms of TbpB associate with different families of TbpA which are distinguishable on the basis of homology. Despite being of similar molecular weight, they are known as the high molecular weight and low molecular weight families because of their association with the high or low molecular weight form of TbpB (Rokbi et al FEMS Microbiol. Lett. 100; 51, 1993). The terms TbpA (high) and TbpA (low) are used to refer to these two forms of TbpA, and similarly for TbpB. hnmunogenic compositions of the disclosure may comprise TbpA and TbpB from serogroups A, B, C, Y and W-135 of N. meningitidis as well as iron acquisition proteins from other bacteria including N. gonorrhoeae. Transferrin binding proteins TbpA and TbpB have also been referred to as Tbp1 and Tbp2 respectively (Cornelissen et al Infection and Immunity 65; 822, 1997).

TbpA contains several distinct regions. For example, in the case of TbpA from N. meningitidis strain H44/76, the amino terminal 186 amino acids form an internal globular domain, 22 beta strands span the membrane, forming a beta barrel structure.

These are linked by short intracellular loops and larger extracellular loops.

Extracellular loops 2, 3 and 5 have the highest degree of sequence variability and loop 5 is surface exposed. Loops 5 and 4 are involved in ligand binding.

In one aspect fragments of TbpA include the extracellular loops of TbpA. Using the sequence of TbpA from N. meningitidis strain H44/76, these loops correspond to amino acids 200-202 for loop1, amino acids 226-303 for loop 2, amino acids 348-395 for loop 3, amino acids 438-471 for loop 4, amino acids 512-576 for loop 5, amino acids 609-625 for loop 6, amino acids 661-671 for loop 7, amino acids 707-723 for loop 8, amino acids 769-790 for loop 9, amino acids 814-844 for loop 10 and amino acids 872-903 for loop 11. The corresponding sequences, after sequence alignment, in other Tbp proteins would also constitute suitable fragments. Other suitable fragments would include amino acid sequences constituting loop 2, loop 3, loop 4 or loop 5 of Tbp.

Where the immunogenic compositions of the disclosure comprise TbpA, it is suitable to include both TbpA (high) and TbpA (low).

Although TbpA is suitably presented in an outer membrane vesicle (OMV) vaccine, it may also be part of a subunit vaccine. For instance, isolated iron acquisition proteins which could be introduced into an immunogenic composition of the disclosure are well known in the art (WO00/25811). They may be expressed in a bacterial host, extracted using detergent (for instance 2% Elugent) and purified by affinity chromatography or using standard column chromatography techniques well known to the art (Oakhill et al Biochem J. 2002 364; 613-6).

Where TbpA is presented in an OMV vaccine, its expression can be upregulated by genetic techniques discussed herein, or may suitably be upregulated by growth of the parent strain under iron limitation conditions as described below. This process will also result in the upregulation of variable iron-regulated proteins, particularly FrpB which may become immunodominant and it is therefore advantageous to downregulate the expression of (and suitably delete the genes encoding) such proteins (particularly FrpB) as described below, to ensure that the immunogenic composition of the disclosure elicits an immune response against antigens present in a wide range of Neisserial strains. It is suitable to have both TbpA (high) and TbpA (low) present in the immunogenic composition and this is suitably achieved by combining OMVs derived from two strains, expressing the alternative forms of TbpA.

4. Toxins: Toxins include FrpA (NMB 0585; NMB 1405), FrpA/C (see below for definition), FrpC (NMB 1415; NMB 1405) (WO92/01460), NM-ADPRT (NMB 1343) (13' h International Pathogenic *Neisseria* Conference 2002 Masignani et al pI35), VapD (NMB 1753), lipopolysaccharide (LPS; also called lipooligosaccharide or LOS) immunotype L2 and LPS immunotype L3. FrpA and FrpC contain a region which is conserved between these two proteins and a suitable fragment of the proteins would be a polypeptide containing this conserved fragment, suitably comprising amino acids 227-1004 of the sequence of FrpA/C. These antigens may be derived from *Neisseria* fyzeningitidis or *Neisseria* gonorrlaoeae or other Neisserial strains. The disclosure also includes other toxins from *Neisseria*.

In an alternative embodiment, toxins may include antigens involved in the regulation of toxicity, for example OstA which functions in the synthesis of lipopolysaccharides.

FrpA and FrpC *Neisseria* 7nenngtds encodes two RTX proteins, referred to as FrpA & FrpC secreted upon iron limitation (Thompson et al., (1993) J. Bacteriol. 175: 811-818; Thompson et al., (1993) Infect. Immun. 61: 2906-2911). The RTX (Repeat ToXin) protein family have in common a series of 9 amino acid repeat near their C-termini with the consensus: Leu Xaa Gly Gly Xaa Gly (Asn/Asp) Asp Xaa (LXGGXGN/DDX). The repeats in *E. coli* HIyA are thought to be the site of Ca2+ binding. Meningococcal FrpA and FrpC proteins, as characterized in strain FAM20, share extensive amino-acid similarity in their central and C-terminal regions but very limited similarity (if any) at the N-terminus.

Moreover, the region conserved between FrpA and FrpC exhibit some polymorphism due to repetition (13 times in FrpA and 43 times in FrpC) of a 9 amino acid motif.

Immunogenic compositions of the disclosure may comprise the full length FrpA and/or FrpC or suitably, a fragment comprising the sequence conserved between FrpA and FrpC.

The conserved sequence is made up of repeat units of 9 amino acids.

Immunogenic compositions of the disclosure would suitably comprise more that three repeats, more than 10 repeats, more than 13 repeats, more than 20 repeats or more than 23 repeats.

Such truncates have advantageous properties over the full length molecules and vaccines comprising such antigens form an independent aspect of disclosure as sell as being incorporated in the immunogenic compositions of the disclosure.

Sequences conserved between FrpA and FrpC are designated FrpA/C and whereever FrpA or FrpC forms a constituent of immunogenic compositions of the disclosure, FrpA/C could be advantageously used. Amino acids 277-1004 of the FrpA sequence is the preferred conserved region. The above sequence can be extended or truncated by up to 1, 3, 5, 7, 10, 15, 20, 25, or 30 amino acids at either or both N or C termini.

LPS:

In one aspect of the disclosure L2 LOS is combined with fHbp.

LPS is suitably presented in an outer membrane vesicle (OMV) (suitably where the vesicle is extracted with a low percentage detergent, more suitably 0-0.5%, 0.02-0.4%, 0.04-0. 3%, 0.06-0.2%, 0.08-0.15% or 0.1%, most suitably deoxycholate [DOC]) but may also be part of a subunit vaccine. LPS may be isolated using well known precedure including the hot water-phenol procedure (Wesphal and Jann Meth. Carbo. Chem. 5; 83-91 1965). See also Galanos et al. 1969, Eur J Biochem 9: 245-249, and Wu et al. 1987, Anal Bio Chem 160: 281-289. LPS may be used plain or conjugated to a source of T-cell epitopes such as tetanus toxoid, Diphtheria toxoid, CRM-197 or OMV outer membrane proteins. Techniques for conjugating isolated LOS are also known (see for instance EP 941738 incorporated by reference herein).

Where LOS (in particular the LOS of the disclosure) is present in a bleb formulation the LOS is suitably conjugated in situ by methods allowing the conjugation of LOS to one or more outer membrane proteins also present on the bleb preparation (e.g. PorA or PorB in meningococcus).

This process can advantageously enhance the stability and/or immunogenicity (providing T-cell help) and/or antigenicity of the LOS antigen within the bleb formulation-thus giving T-cell help for the T-independent oligosaccharide immunogen in its most protective conformation—as LOS in its natural environment on the surface of meningococcal outer membrane. In addition, conjugation of the LOS within the bleb can result in a detoxification of the LOS (the Lipid A portion being stably buried in the outer membrane thus being less available to cause toxicity). Thus the detoxification methods mentioned herein of isolating blebs from htrB' or msbB' mutants, or by adding non toxic peptide functional equivalent of polymyxin B [a molecule with high affinity to Lipid A] to the composition (see WO 93/14115, WO 95/03327, Velucchi et al (1997) J Endotoxin Res 4: 1-12, and EP 976402 for further details of non-toxic peptide functional equivalents of polymyxin B-particularly the use of the peptide SAEP 2 (of sequence KTKCKFLKKC where the 2 cysteines form a disulphide bridge)) may not be required (but which may be added in combination for additional security). Thus the inventors have found that a composition comprising blebs wherein LOS present in the blebs has been conjugated in an intra-bleb fashion to outer membrane proteins also present in the bleb can form the basis of a vaccine for the treatment or prevention of diseases caused by the organism from which the blebs have been derived, wherein such vaccine is substantially non-toxic and is capable of inducing a T-dependent bactericidal response against LOS in its native environment.

This disclosure therefore further provides such an intra-bleb LOS conjugated meningococcal bleb preparation.

Such bleb preparations may be isolated from the bacterial in question (see WO 01/09350), and then subjected to known conjugation chemistries to link groups (e.g. NH2 or COOH) on the oligosaccharide portion of LOS to groups (e.g. NH2 or COOH) on bleb outer membrane proteins. Cross-linking techniques using glutaraldehyde, formaldehyde, or glutaraldehyde/formaldehyde mixes may be used, but it is preferred that more selective chemistries are used such as EDAC or EDAC/NHS (J. V. Staros, R. W. Wright and D. M. Swingle. Enhancement by N-hydroxysuccinimide of water-soluble carbodiimide-mediated coupling reactions. Analytical chemistry 156: 220-222 (1986); and Bioconjugates Techniques. Greg T. Hermanson (1996) pp 173-176). Other conjugation chemistries or treatments capable of creating covalent links between LOS and protein molecules that could be used are described in EP 941738.

In one aspect the bleb preparations are conjugated in the absence of capsular polysaccharide. The blebs may be isolated from a strain which does not produce capsular polysaccharide (naturally or via mutation as described below), or may be purified from most and suitably all contaminating capsular polysaccharide. In this way, the intra-bleb LOS conjugation reaction is much more efficient.

In one aspect more than 10, 20, 30, 40, 50, 60, 70, 80, 90, or 95% of the LOS present in the blebs is cross-linked/conjugated.

Intrableb conjugation should suitably incorporate 1, 2 or all 3 of the following process steps: conjugation pH should be greater than pH 7.0, suitably greater than or equal to pH 7.5 (most suitably under pH 9); conditions of 1-5% suitably 2-4% most suitably around 3% sucrose should be maintained during the reaction; NaCl should be minimised in the conjugation reaction, suitably under 0.1M, 0.05M, 0.01M, 0.005M, 0.001M, and most suitably not present at all. All these process features make sure that the blebs remain stable and in solution throughout the conjugation process.

The EDAC/NHS conjugation process is a suitable process for intra-bleb conjugation.

EDAC/NHS is preferred to formalydehyde which can cross-link to too high an extent thus adversely affecting filterability. EDAC reacts with carboxylic acids (such as KDO in LOS) to create an active-ester intermediate. In the presence of an amine nucleophile (such as lysines in outer membrane proteins such as PorB), an amide bond is formed with release of an isourea by-product. However, the efficiency of an EDAC-mediated reaction may be increased through the formation of a Sulfo-NHS ester intermediate. The Sulfo-NEIS ester survives in aqueous solution longer than the active ester formed from the reaction of EDAC alone with a carboxylate. Thus, higher yields of amide bond formation may be realized using this two-stage process.

EDAC/NHS conjugation is discussed in J. V. Staros, R. W. Wright and D. M. Swingle, Enhancement by N-hydroxysuccinimide of water-soluble carbodiimide-mediated coupling reactions. Analytical chemistry 156: 220-222 (1986); and Bioconjugates Techniques. Greg T. Hermanson (1996) pp 173-176. In one aspect 0.01-5 mg EDAC/mg bleb is used in the reaction, more suitably 0.05-1 mg EDAC/mg bleb. The amount of EDAC used depends on the amount of LOS present in the sample which in turn depends on the deoxycholate (DOC) used to extract the blebs. At low % DOC (e.g. 0.1%), high amounts of EDAC are used (1 mg/mg and beyond), however at higher % DOC (e.g. 0.5%), lower amounts of EDAC are used (0.025-0.1 mg/mg) to avoid too much inter-bleb crosslinking.

One process of the disclosure is therefore a process for producing intra-bleb conjugated LOS (suitably meningococcal) comprising the steps of conjugating blebs in the presence of EDAC/NHS at a pH between pH 7.0 and pH 9.0 (suitably around pH 7.5), in 1-5% (suitably around 3%) sucrose, and optionally in conditions substantially devoid of NaCl (as described above), and isolating the conjugated blebs from the reaction mix.

The reaction may be followed on Western separation gels of the reaction mixture using anti-LOS (e.g. anti-L2 or anti-L3) mAbs to show the increase of LOS molecular weight for a greater proportion of the LOS in the blebs as reaction time goes on.

Yields of 99% blebs can be recovered using such techniques.

EDAC was found to be an excellent intra-bleb cross-linking agent in that it cross-linked LOS to OMP sufficiently for improved LOS T-dependent immunogenicity, but did not cross link it to such a high degree that problems such as poor filterability, aggregation and inter-bleb cross-linking occurred. The morphology of the blebs generated is similar to that of unconjugated blebs (by electron microscope). In addition, the above protocol avoided an overly high cross-linking to take place (which can decrease the immunogenicity of protective OMPs naturally present on the surface of the bleb e.g. TbpA or Hsf).

It is suitable that the meningococcal strain from which the blebs are derived is a mutant strain that cannot produce capsular polysaccharide (e.g. one of the mutant strains described below, in particular siaD'). It is also suitable that immunogenic compositions effective against meningococcal disease comprise both an L2 and L3 bleb, wherein the L2 and L3 LOS are both conjugated to bleb outer membrane proteins. Furthermore, it is preferred that the LOS structure within the intra-bleb conjugated bleb is consistent with it having been derived from an IgtB-meningococcal strain (as described below). Most suitably immunogenic compositions comprise intrableb-conjugated blebs: derived from a mutant meningococcal strain that cannot produce capsular polysaccharide and is IgtB-; comprising L2 and L3 blebs derived from mutant meningococcal strains that cannot produce capsular polysaccharide; comprising L2 and L3 blebs derived from mutant meningococcal strains that are IgtB-; or most suitably comprising L2 and L3 blebs derived from mutant meningococcal strains that cannot produce capsular polysaccharide and are IgtB-.

Typical L3 meningococcal strain that can be used for the present disclosure is H44/76 menB strain. A typical L2 strain is the B16B6 menB strain or the 39E meningococcus type C strain.

As stated above, the blebs of the disclosure have been detoxified to a degree by the act of conjugation, and need not be detoxified any further, however further detoxification methods may be used for additional security, for instance using blebs derived from a meningococcal strain that is htrB' or msbB- or adding a non-toxic peptide functional equivalent of polymyxin B [a molecule with high affinity to Lipid A] (suitably SEAP 2) to the bleb composition (as described above).

In the above way meningococcal blebs and immunogenic compositions comprising blebs are provided which have as an important antigen LOS which is substantially non-toxic, devoid of autoimmunity problems, has a T-dependent character, is present in its natural environment, and is capable of inducing a bactericidal antibody response against more than 90% of meningococcal strains (in the case of L2+L3 compositions).

In one aspect intrableb LOS conjugation should incorporate 1, 2 or all 3 of the following process steps: conjugation pH should be greater than pH 7.0, suitably greater than or equal to pH 7.5 (most suitably under pH 9); conditions of 1-5% suitably 2-4% most suitably around 3% sucrose should be maintained during the reaction; NaCl should be minimised in the conjugation reaction, suitably under 0.1M, 0.05M, 0.01M, 0.005M, 0.001M, and most suitably not present at all. All these process features make sure that the blebs remain stable and in solution throughout the conjugation process.

Although LOS can be conjugated within blebs to outer membrane proteins by various techniques and chemistries, the EDAC/NHS conjugation process is a preferred process for intra-bleb conjugation. EDAC/NHS is preferred to formalydehyde which can cross-link to too high an extent thus adversely affecting filterability. EDAC reacts with carboxylic acids to create an active-ester intermediate.

In the presence of an amine nucleophile, an amide bond is formed with release of an isourea by-product. However, the efficiency of an EDAC-mediated reaction may be increased through the formation of a Sulfo-NHS ester intermediate. The Sulfo-NHS ester survives in aqueous solution longer than the active ester formed from the reaction of EDAC alone with a carboxylate. Thus, higher yields of amide bond formation may be realized using this two-stage process. EDAC/NHS conjugation is discussed in J. V. Staros, R. W. Wright and D. M. Swingle. Enhancement by N-hydroxysuccinimide of water-soluble carbodiimide-mediated coupling reactions. Analytical chemistry 156: 220-222 (1986); and Bioconjugates Techniques. Greg T. Hermanson (1996) pp 173-176.

5. Integral Outer Membrane Proteins

Other categories of Neisserial proteins may also be candidates for inclusion in the Neisserial vaccines of the disclosure and may be able to combine with other antigens in a surprisingly effective manner. Membrane associated proteins, particularly integral membrane proteins and most advantageously outer membrane proteins, especially integral outer membrane proteins may be used in the compositions of the present disclosure. An example of such a protein is PIDA also known as Omp IA (NMB 0464) (WO00/15801) which is a Neisserial phospholipase outer membrane protein. Further examples are TspA (NMB 0341) (Infect. Immun. 1999, 67; 3533-3541) and TspB (T-cell stimulating protein) (WO 00/03003; NMB 1548, NMB 1628 or NMB 1747).

Further examples include Tdfh, TdfI (as mentioned above) PiIQ (NMB 1812) (WO99/61620), OMP85—also known as D15—(NMB 0182) (WO00/23593), NspA (U52066) (WO96/29412), FhaC (NMB 0496 or NMB 1780), PorB (NMB 2039) (Mol. Biol. Evol. 12; 363-370, 1995), HpuB (NC_003116. 1), TdfH (NMB 1497) (Microbiology 2001, 147; 1277-1290), OstA (NMB 0280), MItA also known as GNA33 and Lipo30 (NMB0033), HtrA (NMB 0532; WO 99/55872), HimD (NMB 1302), H isD (NMB 1581), HIpA (NMB 1946), NMB 1124, NMB 1162, NMB 1220, NMB 1313, NMB 1953, HtrA, TbpA (NMB 0461) (WO92/03467) (see also above under iron acquisition proteins) and LbpA (NMB 1541).

OMP85 Immunogenic compositions of the disclosure may comprise the full length OMP85, suitably as part of an OMV preparation. Fragments of OMP85 may also be used in immunogenic compositions of the disclosure, in particularly, the surface exposed domain of OMP85 made up of amino acid residues 1-475 or 50-475 is suitably incorporated into a subunit component of the immunogenic compositions of the disclosure. The above sequence for the surface exposed domain of OMP85 can be extended or truncated by up to 1, 3, 5, 7, 10, 15, 20, 25, or 30 amino acids at either or both N or C termini. It is preferred that the signal sequence is omitted from the OMP85 fragment.

OstA OstA functions in the synthesis of lipopolysaccharides and may be considered to be a regulator of toxicity. OstA may alternatively be included in the toxin category where the toxin category is broadened to contain regulators of toxicity as well as toxins.

In another aspect the disclosure relates to a polynucleotide encoding a protein or combination of proteins present in the composition as claimed. For example, the fHbp may be provided in combination with a second antigen, either as a polynucleotide encoding a fusion protein or as a polynucleotide encoding polypeptides on the same nucleic acid construct (eg vector construct)

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells.

"Polynucleotide" also embraces relatively short polynucleotides, often referred to as oligonucleotides.

Another aspect of the disclosure relates to an immunological/vaccine formulation which comprises one or more polynucleotide (s). Such techniques are known in the art, see for example Wolff et al., Science, (1990) 247:1465-8.

Such vaccines comprise one or more polynucleotide (s) encoding a plurality of proteins corresponding to protein combinations of the disclosure described above.

The expression of proteins from such polynucleotides may be under the control of a eukaryotic promoter capable of driving expression within a mammalian cell. The polynucleotide may additionally comprise sequence encoding other antigens.

Examples of eukaryotic promoters that could drive the expression include viral promoters from viruses including adenoviral promoters, retroviral promoters.

Alternatively, mammalian promoters could be used to drive expression.

In a further aspect the disclosure relates to a method for manufacture of an improved fHbp based composition or vaccine for prevention or amelioration of *Neisseria meningitidis* infection or disease, the method comprising combining fHbp with a second antigen capable of generating an antibody response against Neisseria meningitidis ST269

The composition of the disclosure may be a subunit composition, a composition comprising antigens in the context of an outer membrance vesicle (bleb), or comprise a combination of subunit and outer membrane vesicle.

In one aspect the disclosure relates to culturing a Neisseria species bacterium producing a NMB0964 polypeptide, wherein the NMB0964 polypeptide is produced at a level sufficient to provide for production of outer membrane vesicles that, when administered to a subject, elicit anti-NMB0964 antibodies; preparing outer membrane vesicles from the cultured bacterium; and combining the outer membrane vesicles with a pharmaceutically acceptable excipient to produce an immunogenic composition suitable for administration to a subject in combination with an fHbp polypeptide as defined herein.

Certain aspects are described below.

The immunogenic composition or vaccine of the disclosure may be a subunit composition. Subunit compositions are compositions in which the component or components have been isolated and purified to at least 50%, suitably at least 60%, 70%, 80%, 90% purity.

Subunit compositions may be in aqueous solution. They may comprise detergent, suitably non-ionic, zwitterionic or ionic detergent in order to solubilise hydrophobic portions of the antigens. They may comprise lipids so that liposome structures could be formed, allowing presentation of antigens with a structure that spans a lipid membrane.

N. meningitidis serogroup B (menB) excretes outer membrane blebs in sufficient quantities to allow their manufacture on an industrial scale. An outer membrane vesicle may also be prepared via the process of detergent extraction of the bacterial cells (see for example EP 11243).

The immunogenic composition of the disclosure may also comprise an outer membrane vesicle preparation suitably having an antigen which has been been upregulated, either recombinantly or by other means including growth under metal depleted (eg zinc-depleted or iron-depleted) conditions. Examples of antigens which would be upregulated in such a outer membrane vesicle preparation include; TdfI, TdfH, NspA, Hsf, Hap, OMP85, TbpA (high), TbpA (low), LbpA, TbpB, LbpB, PilQ, AspA, TdfH, PorB, HpuB, P2086, NM-ADPRT, MafA, MafB and PldA. Such preparations may optionally also comprise either or both of LPS immunotype L2 and LPS immunotype L3.

In one aspect the OMV might comprise antigen which have been down-regulated.

The manufacture of bleb preparations from Neisserial strains may be achieved by any of the methods well known to a skilled person. In one aspect the methods disclosed in EP 301992, U.S. Pat. No. 5,597,572, EP 11243 or U.S. Pat. No. 4,271,147, Frederikson et al. (NIPH Annals [1991], 14: 67-80), Zollinger et al. (J. Clin. Invest. [1979], 63: 836-848), Saunders et al. (Infect. Immun. [1999], 67: 113-119), Drabick et al. (Vaccine [2000], 18: 160-172) or WO 01/09350 (Example 8) are used. In general, OMVs are extracted with a detergent, suitably deoxycholate, and nucleic acids are optionally removed enzymatically. Purification is achieved by ultracentrifugation optionally followed by size exclusion chromatography. If 2 or more different blebs of the disclosure are included, they may be combined in a single container to form a multivalent preparation of the disclosure (although a preparation is also considered multivalent if the different blebs of the disclosure are separate compositions in separate containers which are administered at the same time [the same visit to a practitioner] to a host).

OMV preparations are usually sterilised by filtration through a 0.2 Fm filter, and are suitably stored in a sucrose solution (e.g. 3%) which is known to stabilise the bleb preparations.

Upregulation of proteins within outer membrane vesicle preparations may be achieved by insertion of an extra copy of a gene into the Neisserial strain from which the OMV preparation is derived. Alternatively, the promoter of a gene can be exchanged for a stronger promoter in the Neisserial strain from which the OMV preparation is derived. Such techniques are described in WO01/09350. Upregulation of a protein will lead to a higher level of protein being present in OMV compared to the level of protein present in OMV derived from unmodified N. meningitidis (for instance strain H44/76). In one aspect the level will be 1.5, 2, 3, 4, 5, 7, 10 or 20 times higher.

Where LPS is intended to be an additional antigen in the OMV, a protocol using a low concentration of extracting detergent (for example deoxycholate or DOC) may suitably be used in the OMV preparation method so as to preserve high levels of bound LPS whilst removing particularly toxic, poorly bound LPS. The concentration of DOC used is suitably 0-0.5% DOC, 0.02-0.4% DOC, 0.04-0.3% DOC more suitably 0.06%-0.2% DOC or 0.08-0.15% DOC most suitably around or exactly 0.1% DOC.

In one aspect OMVs may include native OMVs obtained without detergent extraction, suitably over-expressing an antigen such as fHbp.

"Stronger promoter sequence" refers to a regulatory control element that increases transcription for a gene encoding antigen of interest.

"Upregulating expression" refers to any means to enhance the expression of an antigen of interest, relative to that of the non-modified (i.e., naturally occurring) bleb.

It is understood that the amount of upregulation will vary depending on the particular antigen of interest but will not exceed an amount that will disrupt the membrane integrity of the bleb. Upregulation of an antigen refers to expression that is at least 10% higher than that of the non-modified bleb. In one aspect it is at least 50% higher. More suitably it is at least 100% (2 fold) higher. Most suitably it is 3, 4, 5, 7, 10, 20 fold higher. Alternatively or additionally, upregulating expression may refer to rendering expression non-conditional on metabolic or nutritional changes, particularly in the case of TbpA, TbpB, LbpA and LbpB. In one aspect the level of expression is assessed when blebs have been derived from bacteria grown in iron limited conditions (for instance in the presence of an iron chelator), or in the presence of Again for the purpose of clarity, the term "engineering a bacterial strain to produce less of said antigen' or "down regulation" refers to any means to reduce the expression of an antigen (or the expression of a functional gene product) of interest, relative to that of the non-modified (i.e. naturally occurring bleb), suitably by deletion, such that expression is at least 10% lower than that of the non-modified bleb.

In one aspect it is at least 50% lower and most suitably completely absent. If the down regulated protein is an enzyme or a functional protein, the downregulation may be achieved by introducing one or more mutations resulting in a 10%, 20%, 50%, 80% or suitably a 100% reduction in enzymatic or functional activity.

The engineering steps required to modulate the expression of Neisserial proteins can be carried out in a variety of ways known to the skilled person. For instance, sequences (e.g. promoters or open reading frames) can be inserted, and promoters/genes can be disrupted by the technique of transposon insertion. For instance, for upregulating a gene's expression, a strong promoter could be inserted via a transposon up to 2 kb upstream of the gene's initiation codon (more suitably 200-600 bp upstream, most suitably approximately 400 bp upstream). Point mutation or deletion may also be used (particularly for down-regulating expression of a gene).

Such methods, however, may be quite unstable or uncertain, and therefore it is preferred that the engineering step is performed via a homologous recombination event. In one aspect, the event takes place between a sequence (a recombinogenic region) of at least 30 nucleotides on the bacterial chromosome, and a sequence (a second recombinogenic region) of at least 30 nucleotides on a vector transformed within the strain. In one aspect the regions are 40-1000 nucleotides, more suitably 100-800 nucleotides, most suitably 500 nucleotides). These recombinogenic regions should be sufficiently similar that they are capable of hybridising to one another under highly stringent conditions.

Methods used to carry out the genetic modification events herein described (such as the upregulation or downregulation of genes by recombination events and the introduction of further gene sequences into a Neisserial genome) are described in WO01/09350. Typical strong promoters that may be integrated in *Neisseria* are porA, porB, IgtF, Opa, p110, 1st, and hpuAB. PorA and PorB are preferred as constitutive, strong promoters. It has been established that the PorB promoter activity is contained in a fragment corresponding to nucleotides-1 to -250 upstream of the initation codon of porB.

Upregulation of Expression of Antigens by Growth in Iron Limitation Media.

The upregulation of some antigens in an outer membrane vesicle preparation of the disclosure is suitably achieved by isolating outer membrane vesicles from a parental strain of *Neisseria* grown under iron limitation conditions. A low concentration of iron in the medium will result in increased expression of proteins involved in iron acquisition including TbpA, TbpB, LbpA, LbpB, HpuA, HpuB and P2086. The expression of these proteins is thereby upregulated without the need for recombinantly modifying the gene involved, for instance by inserting a stronger promoter or inserting an additional copy of the gene. The disclosure would also encompass upregulation of iron acquisition proteins by growth in iron limitation medium where the gene has also been recombinantly modified.

Iron limitation is achieved by the addition of an iron chelator to the culture medium.

Suitable iron chelators include 2,2-Dipyridil, EDDHA (ethylenediamine-di (o-hydroxyphenylacetic acid) and Desferal (deferoxamine mesylate, Sigma). Desferal is the preferred iron chelator and is added to the culture medium at a concentration of between 10 and 100 pM, suitably 25-75 uM, more suitably 50-70 uM, most suitably at 60 11M. The iron content of medium comes primarily from the yeast extract and soy peptone constituents and the amount present may vary between batches. Therefore different concentrations of Desferal may be optimal to achieve upregulation of iron acquisition proteins in different batches of medium. The skilled artisan should easily be able to determine the optimal concentration. In basic terms, enough iron chelator should be added to the medium to upregulate the expression of the desired iron-regulated protein, but not so much so as to adversely affect the growth of the bacteria.

In one aspect zinc limitation may be used to increase expression of TdfI. This may be achieved for example, using a medium low in $Zn^{2+}$ concentration—i.e. under 5, 4, 3, 2, 1, 0.9, 0.8, 0.7, 0.6, 0.5, 0.4, 0.3, 0.2, 0.1, 0.05 or 0.01 μM free $Zn^{2+}$—(such as Roswell Park Memorial Institute medium 1640 (RPMI) which has around 1.69 μM $Zn^{2+}$ by ICP-MS), or by removing $Zn^{2+}$ in the medium, for instance using a known zinc chelator such as TPEN (N,N,N',N'-Tetrakis(2-pyridylmethyl)ethylenediamine)—enough should be added to the medium such that the expression of the NMB0964 is maximised. Synthetic media such a Catlin or Catlin adapted media may also be used (Nutritional profiles of *Neisseria gonorrhoeae*, *Neisseria meningitidis*, and *Neisseria lactamica* in chemically defined media and the use of growth requirements for gonococcal typing. Catlin B W J Infect Dis. 1973 August; 128(2):178-94.).

An OMV vaccine prepared either in specific culture conditions low in Zn2+, or from a mutant *N. meningitidis* strain engineered to either over-express NMB0964 or to remove the Zinc repression mechanism mediated through Zur, is enriched in NMB0964, and such OMVs may elicit good bactericidal antibody responses compared to OMVs which have not been prepared with these methods.

In one aspect, upregulation of iron or other metal acquisition proteins by growth under iron or other appropriate metal limited conditions is combined with recombinant upregulation of other antigens so that the outer membrane vesicle of the disclosure is achieved.

Down Regulation/Removal of Variable and Non-Protective Immunodominant Antigens.

Many surface antigens are variable among bacterial strains and as a consequence are protective only against a limited set of closely related strains. An aspect of this disclosure covers outer membrane vesicles of the disclosure in which the expression of other proteins is reduced, or, suitably, gene (s) encoding variable surface protein (s) are deleted. Such deletion results in a bacterial strain producing blebs which, when administered in a vaccine, have a stronger potential for cross-reactivity against various strains due to a higher influence exerted by conserved proteins (retained on the outer membranes) on the vaccinee's immune system. Examples of such variable antigens in *Neisseria* that may be downregulated in the bleb immunogenic compositions of the disclosure include PorA, PorB, Opa.

Other types of gene that could be down-regulated or switched off are genes which, in vivo, can easily be switched on (expressed) or off by the bacterium. As outer membrane proteins encoded by such genes are not always present on the bacteria, the presence of such proteins in the bleb preparations can also be detrimental to the effectiveness of the vaccine for the reasons stated above. A preferred example to down-regulate or delete is *Neisseria* Opc protein. Anti-Opc immunity induced by an Opc containing bleb vaccine would only have limited protective capacity as the infecting organism could easily become Opc.

For example, these variable or non-protective genes may be down-regulated in expression, or terminally switched off. This has the advantage of concentrating the immune system on better antigens that are present in low amounts on the outer surface of blebs. By down-regulation it is also meant that surface exposed, variable immunodominant loops of the above outer membrane proteins may be altered or deleted in order to make the resulting outer membrane protein less immunodominant.

Methods for downregulation of expression are disclosed in WO01/09350.

Preferred proteins to be downregulated in the bleb immunogenic compositions of the disclosure include PorA and OpA; PorA and OpC; OpA and OpC; PorA and OpA and OpC.

Four different Opa genes are known to exist in the meningococcal genome (Aho et al. 1991 Mol. Microbiol. 5: 1429-37), therefore where Opa is said to be downregulated in expression it is meant that suitably 1, 2, 3 or (suitably) all 4 genes present in meningococcus are so downregulated. Such downregulation may be performed genetically as described in WO 01/09350 or by seeking readily-found, natural, stable meningococcal strains that have no or low expression from the Opa loci. Such strains can be found using the technique described in Poolman et al (1985 J. Med. Micro. 19: 203-209) where cells that are Opa have a different phenotype to cells expressing Opa which can be seen looking at the appearance of the cells on plates or under a microscope. Once found, the strain can be shown to be stably Opa by performing a Western blot on cell contents after a fermentation run to establish the lack of Opa.

Where upregulation of some antigens in the outer membrane vesicle is achieved by growth under iron limitation conditions, the variable protein FrpB (Microbiology 142; 3269-3274, (1996); J. Bacteriol. 181; 2895-2901 (1999)) will also be upregulated. The inventors have found that it is advantageous to downregulate expression of FrpB under these circumstances by downregulating expression of the entire protein as described in WO01/09350 or by deleting variable region (s) of FrpB.

This will ensure that the immune response elicited by the immunogenic composition is directed towards antigens that are present in a wide range of strains. Down regulation of FrpB is suitably combined with down regulation of PorA and OpA; PorA and OpC; OpA and OpC; PorA and OpA and OpC in the bleb immunogenic compositions of the disclosure.

In an alternative embodiment of the disclosure, FrpB is downregulated in outer membrane vesicles which have been prepared from *Neisseria* strains not grown under iron limitation conditions.

The blebs in the immunogenic compositions of the disclosure may be detoxified via methods for detoxification of LPS which are disclosed in WO01/09350. In particular methods for detoxification of LPS of the disclosure involve the downregulation/deletion of htrB and/or msbB enzymes which are disclosed in WO01/09350. The msbB and htrB genes of *Neisseria* are also called IpxL1 and IpxL2, respectively (WO 00/26384) and deletion mutations of these genes are characterised pnenoltypically by the msbB-mutant LOS losing one secondary acyl chain), and the htrB-mutatn LOS losing both secondary acyl chains. WO93/14155 and WO 95/03327 describe nontoxic peptide functional equivalents of polymycin B that may be used in compositions of the disclosure.

Such methods are suitably combined with methods of bleb extraction involving low levels of DOC, suitably 0-0.3% DOC, more suitably 0.05%-0.2% DOC, most suitably around or exactly 0.1% DOC.

Further methods of LPS detoxification include adding to the bleb preparations a non-toxic peptide functional equivalent of polymyxin B (suitably SAEP 2) as described above.

Cross-reactive polysaccharides: the isolation of bacterial outer-membrane blebs from encapsulated Gram-negative bacteria often results in the co-purification of capsular polysaccharide. In some cases, this "contaminant" material may prove useful since polysaccharide may enhance the immune response conferred by other bleb components. In other cases however, the presence of contaminating polysaccharide material in bacterial bleb preparations may prove detrimental to the use of the blebs in a vaccine. For instance, it has been shown at least in the case of *N. meningitidis* that the serogroup B capsular polysaccharide does not confer protective immunity and is susceptible to induce an adverse auto-immune response in humans. Consequently, outer membrane vesicles of the disclosure may be isolated from a bacterial strain for bleb production, which has been engineered such that it is free of capsular polysaccharide. The blebs will then be suitable for use in humans. A particularly preferred example of such a bleb preparation is one from *N. meningitidis* serogroup B devoid of capsular polysaccharide.

This may be achieved by using modified bleb production strains in which the genes necessary for capsular biosynthesis and/or export have been impaired.

Inactivation of the gene coding for capsular polysaccharide biosynthesis or export can be achieved by mutating (point mutation, deletion or insertion) either the control region, the coding region or both (suitably using the homologous recombination techniques described above), or by any other way of decreasing the enzymatic function of such genes. Moreover, inactivation of capsular biosynthesis genes may also be achieved by antisense over-expression or transposon mutagenesis. A preferred method is the deletion of some or all of the *Neisseria meningitidis* cps genes required for polysaccharide biosynthesis and export. For this purpose, the replacement plasmid pMF121 (described in Frosh et al. 1990, Mol. Microbiol. 4: 1215-1218) can be used to deliver a mutation deleting the cpsCAD (+galE) gene cluster.

In WO 01/09350 plasmid pMF121 (Frosch et al., 1990) has been used to construct a *Neisseria meningitidis* B strain lacking the capsular polysaccharide. This plasmid contains the flanking regions of the gene locus coding for the biosynthesis pathway of the group B polysaccharide (B PS), and the erythromycin resistance gene. Deletion of the B PS resulted in loss of expression of the group B capsular polysaccharide as well as a deletion in the active copy of galE leading to the synthesis of galactose deficient LPS.

The safety of antibodies raised to L3 or L2 LPS has been questioned, due to the presence of a structure similar to the lacto-N-neotetraose oligosaccharide group (GalβI-4GlcNAcβI-3GalβI-4GlcβI-) present in human glycosphingolipids. Even if a large number of people has been safely vaccinated with deoxycholate extracted vesicle vaccines containing residual amount of L3 LPS (G. Bjune et al, Lancet (1991), 338, 1093-1096; GVG. Sierra et al, NIPH ann (1991), 14, 195-210), the deletion of the terminal part of the LOS saccharidic is advantageous in preventing any cross-reaction with structures present at the surface of human tissues. In a preferred embodiment, inactivation of the IgtB gene results in an intermediate LPS structure in which the terminal galactose residue and the sialic acid are absent (the mutation leaves a 4GlcNAcp1-3Galp1-4Glcpl-structure in L2 and L3 LOS). Such intermediates could be obtained in an L3 and an L2 LPS strain. An alternative and less preferred (short) version of the LPS can be obtained by turning off the IgtE gene. The gal E mutation may also be used.

A further alternative is use of the galE mutation (Cloning and molecular analysis of the galE gene of *Neisseria meningitidis* and its role in lipopolysaccharide biosynthesis. Jennings M P, van der Ley P, Wilks K E, Maskell D J, Poolman J T, Moxon E R. Mol. Microbiol. 1993 October; 10(2):361-9) to get both a capsule minus strain and a LOS with a short alpha-chain (as IgtE mutation).

A further alternative and less preferred version of the LPS can be obtained by turning off the IgtA gene. If such an IgtA-mutation is selected it is preferred to also turn off IgtC expression to prevent the non-immunogenic L1 immunotype being formed.

LgtB-mutants are most preferred as the inventors have found that this is the optimal troncation for resolving the safety issue whilst still retaining an LPS protective oligosaccharide epitope that can still induce a bactericidal antibody response.

Therefore, immunogenic compositions of the disclosure further comprising L2 or L3 preparations (whether purified or in an isolated bleb) or meningococcal bleb preparations in general are advantageously derived from a Neisserial strain (suitably meningococcal) that has been genetic engineered to permanently downregulate the expression of functional gene product from the IgtB, IgtA or IgtE gene, suitably by switching the gene off, most suitably by deleting all or part of the promoter and/or open-reading frame of the gene.

Where the above immunogenic compositions of the disclosure are derived from a meningococcus B strain, it is further preferred that the capsular polysaccharide (which also contains human-like saccharide structures) is also removed. Although many genes could be switched off to achieve this, the inventors have advantageously shown that it is preferred that the bleb production strain has been genetically engineered to permanently downregulate the expression of functional gene product from the siaD gene (i.e. downregulating a-2-8 polysialyltransferase activity), suitably by switching the gene off, most suitably by deleting all or part of the promoter and/or open-reading frame of the gene. Such an inactivation is described in WO 01/09350. The siaD (also known as synD) mutation is the most advantageous of many mutations that can result in removing the human-similar epitope from the capsular polysaccharide, because it one of the only mutations that has no effect on the biosynthesis of the protective epitopes of LOS, thus being advantageous in a process which aims at ultimately using LOS as a protective antigen, and has a minimal effect on the growth of the bacterium. A preferred aspect of the disclosure is therefore a bleb immunogenic preparation as described above which is derived from an IgtE'siaD', an IgtA-siaD' or, suitably, an IgtB-siaD-meningococcus B mutant strain. The strain itself is a further aspect of the disclosure.

Although siaD-mutation is preferable for the above reasons, other mutations which switch off meningococcus B capsular polysaccharide synthesis may be used.

Thus bleb production strain can be genetically engineered to permanently down-regulate the expression of functional gene product from one or more of the following genes: galE, ctrA, ctrB, ctrC, ctrD, synA (equivalent to synX and siaA), synB (equivalent to siaB) or synC (equivalent to siaC) genes, suitably by switching the gene off, most suitably by deleting all or part of the promoter and/or open-reading frame of the gene. The IgtE-mutation may be combined with one or more of these mutations. In one aspect the IgtB-mutation is combined with one or more of these mutations. A further aspect of the disclosure is therefore a bleb immunogenic preparation as described above which is derived from such a combined mutant strain of meningococcus B. The strain itself is a further aspect of the disclosure.

A Neisserial, locus containing various Igt genes, including IgtB and IgtE, and its sequence is known in the art (see M. P. Jennings et al, Microbiology 1999, 145, 3013-3021 and references cited therein, and J. Exp. Med. 180: 2181-2190 [1994]).

Where full-length (non-truncated) LOS is to be used in the final product, it is desirable for LOS not to be sialyated (as such LOS generates an immune response against the most dangerous, invasive meningococcal B strains which are also unsialylated). In such case using a capsule negative strain which has a deleted synA (equivalent to synX and siaA), synB (equivalent to siaB) or synC (equivalent to siaC) gene is advantageous, as such a mutation also renders menB LOS incapable of being sialylated.

In bleb preparations, particularly in preparations extracted with low DOC concentrations LPS may be used as an antigen in the immunogenic composition of the disclosure. It is however advantageous to downregulate/delete/inactivate enzymatic function of either the galE, IgtE, IgtA (particularly in combination with IgtC), or, suitably, IgtB genes/gene products in order to remove human like lacto-N-neotetraose structures. The Neisserial locus (and sequence thereof) comprising the Igt genes for the biosynthesis of LPS oligosaccharide structure is known in the art (Jennings et al Microbiology 1999 145; 3013-3021 and references cited therein, and J. Exp. Med. <BR> <BR> <BR> <BR> <P>180: 2181-2190 [1994]). Downregulation/deletion of IgtB (or functional gene product) is preferred since it leaves the LPS protective epitope intact.

In *N. meningitidis* serogroup B bleb preparations of the disclosure, the downregulation/deletion of both siaD and IgtB is preferred, (although a combination of IgtB—with any of ctrA-, ctrB-, ctrC-, ctrD', synA- (equivalent to synX- and siaA-), synB- (equivalent to siam-) or synC- (equivalent to siam-) in a meningococcus B bleb production strain may also be used) leading to a bleb preparation with optimal safety and LPS protective epitope retention.

A further aspect of the disclosure is therefore a bleb immunogenic preparation as described above which is derived from such a combined mutant strain of meningococcus B. The strain itself is a further aspect of the disclosure.

Immunogenic composition of the disclosure may comprise at least, one, two, three, four or five different outer membrane vesicle preparations. Where two or more OMV preparations are included, at least one antigen of the disclosure is upregulated in each OMV. Such OMV preparations may be derived from Neisserial strains of the same species and serogroup or suitably from Neisserial strains of different class, serogroup, serotype, subserotype or immunotype. For example, an immunogenic composition may comprise one or more outer membrane vesicle preparation (s) which contains LPS of immunotype L2 and one or more outer membrane vesicle preparation which contains LPS of immunotype L3. L2 or L3 OMV preparations are suitably derived from a stable strain which has minimal phase variability in the LPS oligosaccharide synthesis gene locus.

The immunogenic compositions of the disclosure may also comprise both a subunit composition and an outer membrane vesicle. There are several antigens that are particularly suitable for inclusion in a subunit composition due to their solubility.

Examples of such proteins include; TdfI, FhaB, NspA, passenger domain of Hsf, passenger domain of Hap, passenger domain of AspA, AspA, OMP85, FrpA, FrpC, TbpB, LbpB, PiIQ. The outer membrane vesicle preparation would have at least one different antigen selected from the following list which has been recombinantly upregulated in the outer membrane vesicle: NspA, Hsf, Hap, OMP85, TbpA (high), TbpA (low), LbpA, TbpB, LbpB, NadA, TspA, TspB, PiIC, PiIQ, TdfH, PorB, HpuB, P2086, NM-ADPRT, MafA, MafB and PIdA; and optionally comprise either or both of LPS immunotype L2 and LPS immunotype L3.

Another aspect of the disclosure is a genetically engineered Neisserial strain from which an outer membrane vesicle of the disclosures (optionally having at least two proteins of the disclosure recombinantly upregulated, as described above) may be derived. Such Neisserial strains may be *Neisseria meningitidis* or *Neisseria gonorrhoeae*.

The strain may also have been engineered (as described above) to downregulate the expression of other Neisserial proteins including the expression of one, two, three, four, five, six, seven or eight of galE, LgtB, LgtE, SiaD, OpC, OpA, PorA, FrpB, msbB and HtrB. Preferred combinations for downregulation include down regulation (suitably deletion) of at least LgtB and SiaD, downregulation of at least PorA and OpC, downregulation of at least PorA and OpA and downregulation of at least PorA, OpA and OpC.

In accordance with the above disclosure concerning bleb production, further aspects of the disclosure includes methods of making the immunogenic composition or vaccine of the disclosure. These include a method comprising a step of mixing together the chimaeric protein of the disclosure with an isolated antigens or proteins from *Neisseria*, which may be present in the form of blebs derived from the Neisserial strains of the disclosure, to make an immunogenic composition of the disclosure, and a method of making the vaccine of the disclosure comprising a step of combining the immunogenic composition of the disclosure with a pharmaceutically acceptable carrier.

Also included in the disclosure are methods of making the immunogenic composition of the disclosure comprising a step of isolating outer membrane vesicles comprising the chimaeric protein from a Neisserial culture. Such a method may involve a further step of combining at least two outer membrane vesicle preparations, in one aspect wherein at least one outer membrane vesicle preparation contains LPS of immunotype L2 and at least one outer membrane vesicle preparation contains LPS of immunotype L3. The disclosure also includes such methods wherein the outer membrane vesicles are isolated by extracting with a concentration of DOC of 0-0.5%. DOC concentrations of 0.3%-0.5% are used to minimise LPS content. In OMV preparations where LPS is to be conserved as an antigen, DOC concentrations of 0-0.3%, suitably 0.05%-0.2%, most suitably of about 0.1 are used for extraction.

The immunogenic composition of the disclosure may further comprise bacterial capsular polysaccharides or oligosaccharides. The capsular polysaccharides or oligosaccharides may be derived from one or more of: *Neisseria meningitidis* serogroup A, C, Y, and/or W-135, *Haemophilus influenzae* b, *Streptococcus pneumoniae*, Group A Streptococci, Group B Streptococci, *Staphylococcus aureus* and *Staphylococcus epidermidis*.

A further aspect of the disclosure are vaccine combinations comprising the antigenic composition of the disclosure with other antigens which are advantageously used against certain disease states including those associated with viral or Gram positive bacteria.

In one preferred combination, the antigenic compositions of the disclosure are formulated with 1, 2, 3 or suitably all 4 of the following meningococcal capsular polysaccharides or oligosaccharides which may be plain or conjugated to a protein carrier: A, C, Y or W-135. In one aspect the immunogenic compositions of the disclosure are formulated with A and C; or C; or C and Y. Such a vaccine containing proteins from *N. meningitidis*, suitably serogroup B may be advantageously used as a global meningococcus vaccine.

In a further preferred embodiment, the antigenic compositions of the disclosure, suitably formulated with 1, 2, 3 or all 4 of the plain or conjugated meningococcal capsular polysaccharides or oligosaccharides A, C, Y or W-135 (as described above), are formulated with a conjugated *H. influenzae* b capsular polysaccharide or oligosaccharides, and/or one or more plain or conjugated pneumococcal capsular polysaccharides or oligosaccharides. Optionally, the vaccine may also comprise one or more protein antigens that can protect a host against *Streptococcus pneumoniae* infection. Such a vaccine may be advantageously used as a global meningitis vaccine.

In a still further preferred embodiment, the immunogenic composition of the disclosure is formulated with capsular polysaccharides or oligosaccharides derived from one or more of *Neisseria meningitidis, Haemophilus influenzae b, Streptococcus pneumoniae*, Group A Streptococci, Group B Streptococci, *Staphylococcus aureus* or *Staphylococcus epidermidis*. The pneumococcal capsular polysaccharide antigens are suitably selected from serotypes 1, 2, 3, 4, 5, 6B, 7F, 8, 9N, 9V, 10A, 11A, 12F, 14, 15B, 17F, 18C, 19A, 19F, 20, 22F, 23F and 33F (most suitably from serotypes 1, 3, 4, 5, 6B, 7F, 9V, 14, 18C, 19F and 23F). A further preferred embodiment would contain the PRP capsular polysaccharides of *Haemophilus influenzae*. A further preferred embodiment would contain the Type 5, Type 8 or 336 capsular polysaccharides of *Staphylococcus aureus*. A further preferred embodiment would contain the Type I, Type II or Type III capsular polysaccharides of *Staphylococcus epidermidis*. A further preferred embodiment would contain the Type Ia, Type Ic, Type II or Type III capsular polysaccharides of Group B streptocoocus. A further preferred embodiment would contain the capsular polysaccharides of Group A *streptococcus*, suitably further comprising at least one M protein and more suitably multiple types of M protein.

Such capsular polysaccharides of the disclosure may be unconjugated or conjugated to a carrier protein such as tetatus toxoid, tetanus toxoid fragment C, diphtheria toxoid, CRM197, pneumolysin, Protein D (U.S. Pat. No. 6,342, 224). The polysaccharide conjugate may be prepared by any known coupling technique. For example the polysaccharide can be coupled via a thioether linkage. This conjugation method relies on activation of the polysaccharide with 1-cyano-4-dimethylamino pyridinium tetrafluoroborate (CDAP) to form a cyanate ester. The activated polysaccharide may thus be coupled directly or via a spacer group to an amino group on the carrier protein. In one aspect, the cyanate ester is coupled with hexane diamine and the amino-derivatised polysaccharide is conjugated to the carrier protein using heteroligation chemistry involving the formation of the thioether linkage. Such conjugates are described in PCT published application WO93/15760 Uniformed Services University.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508. A further method involves the coupling of a cyanogen bromide activated polysaccharide derivatised with adipic acid hydrazide (ADH) to the protein carrier by Carbodiimide condensation (Chu C. et al Infect. Immunity, 1983 245 256). Where oligosaccharides are included, it is preferred that they be conjugated.

Preferred pneumococcal proteins antigens are those pneumococcal proteins which are exposed on the outer surface of the pneumococcus (capable of being recognised by a host's immune system during at least part of the life cycle of the pneumococcus), or are proteins which are secreted or released by the pneumococcus.

Most suitably, the protein is a toxin, adhesin, 2-component signal tranducer, or lipoprotein of *Streptococcus pneumoniae*, or fragments thereof. Particularly preferred proteins include, but are not limited to: pneumolysin (suitably detoxified by chemical treatment or mutation) [Mitchell et al. Nucleic Acids Res. 1990 Jul. 11; 18 (13): 4010"Comparison of pneumolysin genes and proteins from *Streptococcus pneumoniae* types 1 and 2.", Mitchell et al. Biochim Biophys Acta 1989 Jan. 23; 1007 (1): 67-72"Expression of the pneumolysin gene in *Escherichia coli*: rapid purification and biological properties.", WO 96/05859 (A. Cyanamid), WO 90/06951 (Paton et al), WO 99/03884 (NAVA)]; PspA and transmembrane deletion variants thereof (U.S. Pat. No. 5,804,193-Briles et al.); PspC and transmembrane deletion variants thereof (WO 97/09994-Briles et al); PsaA and transmembrane deletion variants thereof (Berry & Paton, Infect Immun 1996 December; 64 (12): 5255-62 "Sequence heterogeneity of PsaA, a 37-kilodalton putative adhesin essential for virulence of *Streptococcus praeumoniae*"); pneumococcal choline binding proteins and transmembrane deletion variants thereof; CbpA and transmembrane deletion variants thereof (WO 97/41151; WO 99/51266); Glyceraldehyde-3-phosphate-dehydrogenase (Infect. Immun. 1996 64: 3544); HSP70 (WO 96/40928); PcpA (Sanchez-Beato et al. FEMS Microbiol Lett 1998, 164: 207-14); M like protein, (EP 0837130) and adhesin 18627, (EP 0834568). Further suitable pneumococcal protein antigens are those disclosed in WO 98/18931, particularly those selected in WO 98/18930 and PCT/US99/30390.

The immunogenic composition/vaccine of the disclosure may also optionally comprise outer membrane vesicle preparations made from other Gram negative bacteria, for example *Moraxella catarrhalis* or *Haemophilus influenzae*.

Immunogenic compositions of the disclosure may further comprise OMV preparations derived from *Moraxella catarrhalis*. Engineered OMV preparations can be derived from *Moraxella catarrhalis* as described in WO01/09350. One or more of the following genes (encoding protective antigens) are preferred for upregulation: OMP106 (WO 97/41731 & WO 96/34960), HasR (PCT/EP99/03824), PilQ (PCT/EP99/03823), OMP85 (PCT/EP00/01468), lipo06 (GB 9917977.2), lipo10 (GB 9918208.1), lipo11 (GB 9918302.2), lipo18 (GB 9918038.2), P6 (PCT/EP99/03038), ompCD, CopB (Helminen M E, et al (1993) Infect. Immun. 61: 2003-2010), D15 (PCT/EP99/03822), OmpIAl (PCT/EP99/06781), Hly3 (PCT/EP99/03257), LbpA and LbpB (WO 98/55606), TbpA and TbpB (WO 97/13785 & WO 97/32980), OmpE, UspA1 and UspA2 (WO 93/03761), and Omp21. They are also preferred as genes which may be heterologously introduced into other Gram-negative bacteria.

One or more of the following genes are preferred for downregulation: CopB, OMP106, OmpBl, TbpA, TbpB, LbpA, and LbpB.

One or more of the following genes are preferred for downregulation: htrB, msbB and IpxK.

One or more of the following genes are preferred for upregulation: pmrA, pmrB, pmrE, and pmrF.

Immunogenic compositions of the disclosure may further comprise OMV preparations derived from *Haemophilus influenzae*. Engineered OMV preparations can be derived from *Haemophilus influenzae* as described in WO01/09350. One or more of the following genes (encoding protective antigens) are preferred for upregulation: D15 (WO 94/12641), P6 (EP 281673), TbpA (WO96/40929; WO95/13370), TbpB (WO96/40929; WO95/13370), P2, P5 (WO 94/26304), OMP26 (WO 97/01638), HMW1, HMW2, HMW3, HMW4, Hia, Hsf, Hap, Hin47, and Hif (all genes in this operon should be upregulated in order to upregulate pilin). They are also preferred as genes which may be heterologously introduced into other Gram-negative bacteria.

One or more of the following genes are preferred for downregulation: P2, P5, Hif, IgA1-protease, HgpA, HgpB, HMW1, HMW2, Hxu, htrB, msbB and IpxK.

One or more of the following genes are preferred for upregulation: pmrA, pmrB, pmrE, and pmrF.

The immunogenic composition/vaccine of the disclosure may also optionally comprise antigens providing protection against one or more of Diphtheria, tetanus and *Bordetella pertussis* infections. The pertussis component may be killed whole cell *B. pertussis* (Pw) or acellular pertussis (Pa) which contains at least one antigen (suitably 2 or all 3) from PT, FHA and 69 kDa pertactin. Typically, the antigens providing protection against Diphtheria and tetanus would be Diphtheria toxoid and tetanus toxoid. The toxoids may chemically inactivated toxins or toxins inactivated by the introduction of point mutations.

The immunogenic composition/vaccine may also optionally comprise one or more antigens that can protect a host against non-typeable Haemophillus influenzae, RSV and/or one or more antigens that can protect a host against influenza virus. Such a vaccine may be advantageously used as a global otitis media vaccine.

Preferred non-typeable *H. influenzae* protein antigens include Fimbrin protein (U.S. Pat. No. 5,766,608) and fusions comprising peptides therefrom (eg LB1 Fusion) (U.S. Pat. No. 5,843,464-Ohio State Research Foundation), OMP26, P6, protein D, TbpA, TbpB, Hia, Hmw1, Hmw2, Hap, and D15.

Preferred influenza virus antigens include whole, live or inactivated virus, split influenza virus, grown in eggs or MDCK cells, or Vero cells or whole flu virosomes (as described by R. Gluck, Vaccine, 1992, 10, 915-920) or purified or recombinant proteins thereof, such as HA, NP, NA, or M proteins, or combinations thereof.

Preferred RSV (Respiratory Syncytial Virus) antigens include the F glycoprotein, the G glycoprotein, the HN protein, the M protein or derivatives thereof.

Immunogenic compositions of the disclosure may include proteins of *Moraxella catarrhalis* include TbpA (WO97/13785; WO99/52947), TbpB (WO97/13785; WO99/52947; Mathers et al FEMS Immunol Med Microbiol 1997 19; 231-236; Myers et al Infect Immun 1998 66; 4183-4192), LbpA, LbpB (Du et al Infect Immun 1998 66; 3656-3665), UspA1, UspA2 (Aebi et al Infect Immun. 1997 65; 4367-4377), OMP106 (U.S. Pat. No. 6,214,981), Ton-B dependent receptor (WO00/78968), CopB (Sethi et al Infect. Immun. 1997 65; 3666-3671), and HasR receptor (WO00/78968); proteins of *Haemophilus influenzae* include HMW (St Geme et al Infect Immun 1998 66; 364-368), Hia (St Geme et al J. Bacteriol. 2000 182; 6005-6013), Tbp1 (WO96/40929; WO95/13370), Tbp2 (WO96/40929; WO95/13370; Gray-Owen et al Infect Immun 1995 63; 1201-1210), LbpA, LbpB (Schryvers et al 1989, 29:121-130), HasR, TonB-dependent receptor (Fleishmann et al Science 1995 269; 496-512), hemoglobin-binding protein, HhuA (Cope et al Infect Immun 2000 68; 4092-4101), HgpA (Maciver et al Infect Immun 1996 64; 3703-3712), HgbA, HgbB and HgbC (Jin et al Infect Immun 1996 64; 3134-3141), HxuA (Cope et al Mol Microbic) 1994 13; 863-873), HxuC (Cope et al Infect Immun 2001 69; 2353-2363); proteins from *Neisseria* meni7 ngitidis include Tbp1, Tbp2, FbpA, FbpB, BfrA, BfrB (Tettelin et al Science 2000 287; 1809-1815), LbpA, LbpB and HmbR.

In one aspect the disclosure also relates to a pharmaceutical composition comprising antigens and immunogenic compositions of the disclosure in combination with a pharmaceutically acceptable excipient. Suitable excipients are well known in the art. Suitable excipients are well known in the art. Suitable excipients are typically large, slowly metabolised macromolecules such as proteins, saccharides, polylactic acids, polyglycolic acids, polymeric amino acids, amino acid copolymers, sucrose (Paoletti et al., 2001, Vaccine, 19:2118), trehalose (WO 00/56365), lactose and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate buffered physiologic saline is a typical carrier. A thorough discussion of pharmaceutically acceptable excipients is available in reference Gennaro, 2000, Remington: The Science and Practice of Pharmacy, 20.sup.th edition, ISBN: 0683306472.

Elements of the composition may be delivered simultaneously, substantially simultaneously or sequentially.

One embodiment of the disclosure is the formulation of the antigens and immunogenic compositions of the disclosure in a vaccine a pharmaceutically acceptable excipient.

Vaccine preparation is generally described in Vaccine Design ("The subunit and adjuvant approach" (eds Powell M. F. & Newman M. J.) (1995) Plenum Press New York).

The development of effective vaccines requires reliable tests for establishing whether an effective immune response has been elicited in vaccinated individuals. For *N. meningitides*, Serum Bactericidal Activity (SBA) assays may be used to determine suitable antigens for inclusion in any vaccine, and suitably a four-fold increase in SBA may be accepted as a surrogate for protection.

Thus, a dose that would induce a 4-fold increase in SBA may be accepted as a protective dose or an effective amount. In particular, the vaccines or immunogenic compositions of the invention may comprise a human dose of (or of more than) 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 or 10 µg of each of the recited (isolated and/or purified) antigens in the composition.

A pharmaceutical composition or vaccine of the disclosure may also comprise an adjuvant.

Suitable adjuvants include an aluminium salt such as aluminum hydroxide gel (alum) or aluminium phosphate, but may also be a salt of calcium (particularly calcium carbonate), iron or zinc, or may be an insoluble suspension of acylated tyrosine, or acylated sugars, cationically or anionically derivatised polysaccharides, or polyphosphazenes.

Suitable Th1 adjuvant systems that may be used include, Monophosphoryl lipid A, particularly 3-de-O-acylated monophosphoryl lipid A, and a combination of monophosphoryl lipid A, suitably 3-de-O-acylated monophosphoryl lipid A (3D-MPL) together with an aluminium salt (suitably aluminium phosphate). An enhanced system involves the combination of a monophosphoryl lipid A and a saponin derivative particularly the combination of QS21 and 3D-MPL as disclosed in WO 94/00153, or a less reactogenic composition where the QS21 is quenched with cholesterol as disclosed in WO96/33739. A particularly potent adjuvant formulation involving QS21 3D-MPL and tocopherol in an oil in water emulsion is described in WO95/17210 and is a preferred formulation.

The vaccine may comprise a saponin, more suitably QS21. It may also comprise an oil in water emulsion and tocopherol. Unmethylated CpG containing oligo nucleotides (WO 96/02555) are also preferential inducers of a TH1 response and are suitable for use in the present disclosure.

Another aspect of the disclosure is a method of preparing an immune globulin for use in prevention or treatment of Neisserial infection comprising the steps of immunising a recipient with the vaccine of the disclosure and isolating immune globulin from the recipient. An immune globulin prepared by this method is a further aspect of the disclosure. A pharmaceutical composition comprising the immune globulin of the disclosure and a pharmaceutically acceptable carrier is a further aspect of the disclosure which could be used in the manufacture of a medicament for the treatment or prevention of Neisserial disease. A method for treatment or prevention of Neisserial infection comprising a step of administering to a patient an effective amount of the pharmaceutical preparation of the disclosure is a further aspect of the disclosure.

Inocula for polyclonal antibody production are typically prepared by dispersing the antigenic composition in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies.

The antibodies can be isolated to the extent desired by well known techniques such as affinity chromatography (Harlow and Lane Antibodies; a laboratory manual 1988).

Antibodies can include antiserum preparations from a variety of commonly used animals e.g. goats, primates, donkeys, swine, horses, guinea pigs, rats or man. The animals are bled and serum recovered.

An immune globulin produced in accordance with the present disclosure can include whole antibodies, antibody fragments or subfragments. Antibodies can be whole immunoglobulins of any class e.g. IgG, IgM, IgA, IgD or IgE, chimeric antibodies or hybrid antibodies with dual specificity to two or more antigens of the disclosure. They may also be fragments e.g. F (ab') 2, Fab', Fab, Fv and the like including hybrid fragments. An immune globulin also includes natural, synthetic or genetically engineered proteins that act like an antibody by binding to specific antigens to form a complex.

A vaccine of the present disclosure can be administered to a recipient who then acts as a source of immune globulin, produced in response to challenge from the specific vaccine. A subject thus treated would donate plasma from which hyperimmune globulin would be obtained via conventional plasma fractionation methodology. The hyperimmune globulin would be administered to another subject in order to impart resistance against or treat Neisserial infection. Hyperimmune globulins of the disclosure are particularly useful for treatment or prevention of Neisserial disease in infants, immune compromised individuals or where treatment is required and there is no time for the individual to produce antibodies in response to vaccination.

An additional aspect of the disclosure is a pharmaceutical composition comprising two of more monoclonal antibodies (or fragments thereof; suitably human or humanised) reactive against at least two constituents of the immunogenic composition of the disclosure, which could be used to treat or prevent infection by Gram negative bacteria, suitably

*Neisseria*, more suitably *Neisseria meningitidis* or *Neisseria gonorrhoeae* and most suitably *Neisseria meningitidis* serogroup B.

Such pharmaceutical compositions comprise monoclonal antibodies that can be whole immunoglobulins of any class e.g. IgG, IgM, IgA, IgD or IgE, chimeric antibodies or hybrid antibodies with specificity to two or more antigens of the disclosure. They may also be fragments e.g. F (ab') 2, Fab', Fab, Fv and the like including hybrid fragments.

Methods of making monoclonal antibodies are well known in the art and can include the fusion of splenocytes with myeloma cells (Kohler and Milstein 1975 Nature 256; 495; Antibodies—a laboratory manual Harlow and Lane 1988). Alternatively, monoclonal Fv fragments can be obtained by screening a suitable phage display library (Vaughan T J et al 1998 Nature Biotechnology 16; 535). Monoclonal antibodies may be humanised or part humanised by known methods.

Another aspect of the disclosure involves a method for treatment or prevention of Neisserial disease comprising administering a protective dose (or effective amount) of the vaccine of the disclosure to a host in need thereof.

The disclosure also includes a use of the immunogenic composition of the disclosure in the preparation of a medicament for treatment or prevention of Neisserial infection or disease, and to an immunogenic composition as described herein for treatment or prevention of Neisserial meningitidis infection or disease.

In one aspect the prevention is prevention against menB infection and/or disease.

The host is suitably a human host.

The vaccine preparation of the present disclosure may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Thus one aspect of the present disclosure is a method of immunizing a human host against a disease caused by infection of a gram-negative bacteria, which method comprises administering to the host an immunoprotective dose of the preparation of the present disclosure.

The amount of antigen in each vaccine dose is selected as an amount which induces an immunoprotective response without significant, adverse side effects in typical vaccines. Such amount will vary depending upon which specific immunogen is employed and how it is presented. Generally, it is expected that each dose will comprise 1-100 pg of protein antigen or OMV preparation, suitably 5-50 pg, and most typically in the range 5-25 ut.

An optimal amount for a particular vaccine can be ascertained by standard studies involving observation of appropriate immune responses in subjects.

Following an initial vaccination, subjects may receive one or several booster immunisations adequately spaced.

The vaccines of the disclosure are suitably immunoprotective and non-toxic and suitable for paediatric or adolescent use.

By paediatric use it is meant use in infants less than 4 years old.

By immunoprotective it is meant that the SBA and/or animal protection model and/or adhesion blocking assay described above are satisfactorily met.

By non-toxic it is meant that there is no more than a satisfactory level of endotoxin activity in the vaccine as measured by the well-known LAL and pyrogenicity assays.

The efficacy of vaccines can be assessed through a variety of assays. Protection assays in animal models are well known in the art. Furthermore, serum bactericidal assay (SBA) is the most commonly agreed immunological marker to estimate the efficacy of a meningococcal vaccine (Perkins et al. J Infect Dis. 1998, 177:683-691).

Such a synergistic response may be characterised by the SBA elicited by the combination of antigens being at least 50%, two times, three times, suitably four times, five times, six times, seven times, eight times, nine times and most suitably ten times higher than the SBA elicited by each antigen separately. In one aspect SBA is measured against a homologous strain from which the antigens are derived and suitably also against a panel of heterologous strains. (See below for a representative panel for instance NZ124/98 (B:4:P1.7-2,4:L3 ST-44 complex), 760676 (B:2a:P1.5,2:L2 ST-11 complex), BZ10 (B: 2b: P1. 2) belonging to the A-4 cluster; B16B6 (B: 2a: P1. 2) belonging to the ET-37 complex; and H44/76 (B: 15: P1. 7, 16)). SBA is the most commonly agreed immunological marker to estimate the efficacy of a meningococcal vaccine (Perkins et al. J Infect Dis. 1998, 177: 683-691). Satisfactory SBA can be ascertained by any known method. SBA can be carried out using sera obtained from animal models or from human subjects.

A preferred method of conducting SBA with human sera is the following. A blood sample is taken prior to the first vaccination, two months after the second vaccination and one month after the third vaccination (three vaccinations in one year being a typical human primary vaccination schedule administered at, for instance, 0, 2 and 4 months, or 0, 1 and 6 months). Such human primary vaccination schedules can be carried out on infants under 1 year old (for instance at the same time as Hib vaccinations are carried out) or 2-4 year olds or adolescents may also be vaccinated to test SBA with such a primary vaccination schedule. A further blood sample may be taken 6 to 12 months after primary vaccination and one month after a booster dose, if applicable.

SBA will be satisfactory for an antigen or bleb preparation with homologous bactericidal activity if one month after the third vaccine dose (of the primary vaccination schedule) (in 2-4 year olds or adolescents, but suitably in infants in the first year of life) the percentage of subjects with a four-fold increase in terms of SBA (antibody dilution) titre (compared with pre-vaccination titre) against the strain of meningococcus from which the antigens of the disclosure were derived is greater than 30%, suitably greater than 40%, more suitably greater than 50%, and most suitably greater than 60% of the subjects.

Of course an antigen or bleb preparation with heterologous bactericidal activity can also constitute bleb preparation with homologous bactericidal activity if it can also elicit satisfactory SBA against the meningococcal strain from which it is derived.

SBA will be satisfactory for an antigen or bleb preparation with heterologous bactericidal activity if one month after the third vaccine dose (of the primary vaccination schedule) (in 2-4 year olds or adolescents, but suitably in infants in the first year of life) the percentage of subjects with a four-fold increase in terms of SBA (antibody dilution) titre (compared with pre-vaccination titre) against three heterologous strains of meningococcus is greater than 20%, suitably greater than 30%, more suitably greater than 35%, and most suitably greater than 40% of the subjects. Such a test is a good indication of whether the antigen or bleb preparation with heterologous bactericidal activity can induce cross-bactericidal antibodies against various meningococcal strains. The three heterologous strains should suitably have different electrophoretic type (ET)-complex or multilocus sequence typing (MLST) pattern (see Maiden et al. PNAS USA 1998, 95:3140-5) to each other and suitably to the strain from which the antigen or bleb preparation with heterologous bactericidal activity is made or derived. A skilled person will readily be able to determine three strains with different ET-complex which reflect the genetic diversity observed amongst meningococci, particularly amongst meningococcus type B strains that are recognised as being the cause of significant disease burden and/or that represent recognised MenB hyper-virulent lineages (see Maiden et al. supra). For instance three strains that could be used are the following: BZ10 (B: 2b: P1. 2) belonging to the A-4 cluster; B16B6 (B: 2a: P1. 2) belonging to the ET-37 complex; and H44/76 (B: 15: P1. 7, 16) belonging to the ET-5 complex, or any other strains belonging to the same ET/Cluster. Such strains may be used for testing an antigen or bleb preparation with heterologous bactericidal activity made or derived from, for instance, meningococcal strain CU385 (B: 4: P1. 15) which belongs to the ET-5 complex.

Another sample strain that could be used is from the Lineage 3 epidemic clone (e.g. NZ124 [B: 4: P1. 7, 4]). Another ET-37 strain is NGP165 (B: 2a: P1. 2).

Processes for measuring SBA activity are known in the art. For instance a method that might be used is described in WO 99/09176. In general terms, a culture of the strain to be tested is grown (suitably in conditions of iron depletion—by addition of an iron chelator such as EDDA to the growth medium) in the log phase of growth, or by addition of 1-30 µM of TPEN for zinc depletion. This can be suspended in a medium with BSA (such as Hanks medium with 0.3% BSA) in order to obtain a working cell suspension adjusted to approximately 20000 CFU/ml. A series of reaction mixes can be made mixing a series of two-fold dilutions of sera to be tested (suitably heat-inactivated at 56° C. for 30 min) [for example in a 50 well volume] and the 20000 CFU/ml meningococcal strain suspension to be tested [for example in a 25 well volume]. The reaction vials should be incubated (e.g. 37° C. for 15 minutes) and shaken (e.g. at 210 rpm). The final reaction mixture [for example in a 10 Oul volume] additionally contains a complement source [such as 25% final volume of pretested baby rabbit serum], and is incubated as above [e.g. 37° C. for 60 min]. A sterile polystyrene U-bottom 96-well microtiter plate can be used for this assay. A aliquot [e.g. 10 1l1] can be taken from each well using a multichannel pipette, and dropped onto Mueller-Hinton agar plates (suitably containing 1% Isovitalex and 1% heat-inactivated Horse Serum) and incubated (for example for 18 hours at 37° C. in 5% C02). In one aspect, individual colonies can be counted up to 80 CFU per aliquot. The following three test samples can be used as controls:buffer+ bacteria+complement; buffer+bacteria+inactivated complement; serum+bacteria+inactivated complement. SBA titers can be straightforwardly calculated using a program which processes the data to give a measurement of the dilution which corresponds to 50% of cell killing by a regression calculation.

Alternatively, the synergistic response may be characterised by the efficacy of the combination of antigens in an animal protection assay. For instance, the assays described in example 12 or 13 may be used. In one aspect the number of animals protected by the combination of antigens is significantly improved compared with using the antigens by themselves, particularly at suboptimal doses of antigen.

A successful vaccine for the prevention of infection by N. gono may require more than one of the following elements: generation of serum and/or mucosal antibodies to facilitate complement mediated killing of the gonococcus, and/or to enhance phagocytosis and microbial killing by leukocytes such as polymorphonuclear leukocytes, and/or to prevent attachment of the gonococci to the host tissues; induction of a cell mediated immune response may also participate to protection.

The improvement of efficacy of a bleb gono vaccine preparation of the disclosure can be evaluated by analyzing the induced immune response for serum and/or mucosal antibodies that have antiadherence, and/or opsonizing properties, and/or bactericidal activity, as described by others (McChesney D et al, Infect. Immun. 36: 1006, 1982; Boslego J et al: Efficacy trial of a purified gonococcl pilus vaccine, in Program and Abstracts of the 24th Interscience Conference on Antimicrobial Agents and Chemotherapy, Washington, American Society for Microbiology, 1984; Siegel M et al, J. Infect. Dis 145: 300, 1982; de la Pas, Microbiology, 141 (Pt4): 913-20, 1995).

A mouse model of genital infection by N. gono has recently been described (Plante M, J. Infect. Dis., 182:848-55, 2000). The improvement of efficiency of a bleb gono vaccine of the disclosure could also be evaluated by its ability to prevent or to reduce colonization by N. gono in this mouse model of infection.

Alternatively, the synergistic response may be characterised by the efficacy of the combination of anigens in an adhesion blocking assay. For instance, the assay described in example 11 may be used. In one aspect the extent of blocking induced by antisera raised against the combination of antigens is significantly improved compared with using antisera raised against the antigens by themselves, particularly at suboptimal doses of antibody.

The teaching of all references in the present application, including patent applications and granted patents, are herein fully incorporated by reference. Any patent application to which this application claims priority is incorporated by reference herein in its entirety in the manner described herein for publications and references.

For the avoidance of doubt the terms 'comprising', 'comprise' and 'comprises' herein is intended by the inventors to be optionally substitutable with the terms 'consisting of', 'consist of', and 'consists of', respectively, in every instance. As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Embodiments herein relating to "vaccine compositions" of the disclosure are also applicable to embodiments relating to "immunogenic compositions" of the disclosure, and vice versa. The term "about" (or "around") in all numerical values allows for a 5% variation, i.e. a value of about 1.25% would mean from between 1.19%-1.31%.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the measurement, the method being employed to determine the value, or the variation that exists among the study subjects.

The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, BBC, AAABCCCC, CBBAAA, CABABB, and so forth. The skilled artisan will understand that typically there is no limit on the number of items or terms in any combination, unless otherwise apparent from the context.

Reference to blebs, vesicles and outermembrane vesicles herein is also intended to be a reference to all isolated membrane-derived proteinaceous products known to persons of skill in the art such as blebs, microvesicles, OMVs, OMPC (outer membrane protein complex), or membrane ghosts, and the like.

Reference to "for protection" and "for treatment" in all instances herein can clearly alternatively be written "for use in the prevention" or "for use in the treatment", respectively.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine study, numerous equivalents to the specific procedures described herein. Such equivalents are considered to be within the scope of this disclosure and are covered by the claims. All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The disclosure will be further described by reference to the following, non-limiting, examples:

Example 1

Manufacture of Fusion Proteins

1. Different Fusion Proteins from FHbp were Expressed in *E. coli* Strains.

TABLE 1

| LVL ID | description | Concentration (mg/ml) | Volume (ml) | Buffer | Quantity (mg) |
|---|---|---|---|---|---|
| LVL489 | Fhbp from Family A (full-length - SEQ ID NOS. 9 and 10) | 0.30 | 15 | PBS 1X | 4.5 |
| LVL490 | Fhbp from Family B (full-length - SEQ ID NOS. 11 and 12) | 0.44 | 10 | PBS 1X | 4.4 |
| LVL491 | Fusion w/o mutation (wild type sequence-- SEQ ID NOS. 16 and 17) | 0.50 | 10 | PBS 1X | 5.0 |
| LVL511 | Fusion protein A - SEQ ID NOS. 18 and 19 | 0.59 | 10 | PBS 1X | 5.9 |
| LVL512 | Fusion protein B - SEQ ID NOS. 20 and 21 | 0.56 | 10 | PBS 1X | 5.6 |
| LVL513 | Fusion protein C - SEQ ID NOS. 22 and 23 | 0.25 | 15 | PBS 1X | 3.8 |
| LVL514 | Fusion protein E - - SEQ ID NOS. 24 and 25 | 0.44 | 10 | PBS 1X | 4.4 |

2. Host Strain:

T7 Express competent *E. coli* (NEB catalogue number C2566H): Enhanced BL21 derivative. T7 RNA Polymerase in the lac operon—no λ prophage. Deficient in proteases Lon and OmpT. Resistant to phage T1 (fhuA2). Does not restrict methylated DNA (McrA$^-$, McrBC$^-$, EcoBr$^-$m$^-$, Mrr$^-$). B Strain. Free of animal products. Genotype: fhuA2 lacZ::T7 gene1 [Ion] ompT gal sulA11 R(mcr-73::miniTn10—Tet$^S$)2 [dcm] R(zgb-210::Tn10—Tet$^S$) endA1 Δ(mcrC-nmr)114::IS10:

3. Recombinant Proteins: (Numbering Given in Respect of Full Length Sequence)

The Family B part of the fusion exemplified herein starts from amino acid position 73 of the full length MC58 sequence, which full length sequence itself comprises a mature sequence starting at amino acid 66. (The 7 N-ter aa (CSSGGGG—SEQ ID NO. 11) are replaced by MHHH-HHH (SEQ ID NO. 12) to allow purification).

MC58 part of the fusion finishes at residue 200 ( . . . DIA) if we take account the numbering of the full length MC58 protein sequence, with residue 200 of the full length sequence corresponds to the residue 135 of the mature MC58 sequence.

The 8047 part of the fusion exemplified herein begins at residue 155 of the full length (273 amino acid) 8047 protein sequence (GEH . . . ). The peptide GENT (SEQ ID NO. 13) is identical in family A and B, the junction between the 2 parts is the Gly residue. Residue 155 of the full length sequence corresponds to the residue 136 of the mature sequence.

TABLE 2

| Recombinant plasmids ID | N-terminal | | | C-Terminal* |
|---|---|---|---|---|
| LVL489 | M HH HH HH | FamA (Strain 8047/A.A.: 27 to 273) | | |
| | 1 7 8 | | | 254 |
| LVL490 | M HH HH HH | FamB (Strain MC58/A.A.: 73 to 320) | | |
| | 1 7 8 | | | 255 |
| LVL491 | M HH HH HH | FamB (Strain MC58/A.A.; 73 to 200) | FamA (Strain 8047/ A.A.: 155 to 273) | |
| | 1 7 8 | | 135  136 | 254 |
| LVL511 | M HH HH HH | FamB (Strain MC58/A.A.: 73 to 200) | FamA (Strain 8047/ A.A, = 155 to 273) E217A, T238A**: Disruption of factor H-binding | |
| | 1 7 8 | | 135  136 | 254 |
| LVL512 | M HH HH HH | FamB (Strain MC58/A.A.; 73 to 200) | FamA (Strain 8047/ A.A.: 155 to 273) E217A**: Disruption of factor H-binding | |
| | 1 7 8 | | 135  136 | 254 |
| LVL513 | M HH HH HH | FamB (Strain MC58/A.A.: 73 to 200) | FamA (Strain 8047/A.A.: 155 to 273) E217A, T238A**: Disruption of factor H-binding D146E, K148GR and S203R**: To restore the family B MAb502 | |
| | 1 7 8 | | 135  136 | 254 |
| LVL514 | M HH HH HH | FamB (Strain MC58/A.A.: 73 to 200) | FamA (Strain 8047/A.A.: 155 to 273) E217A, T238A**: Disruption of factor H-binding D146E, K148GR and S203R**: To restore the family B MAb502 R229K**: Could help to restore the Mab502 | |
| | 1 7 8 | | 135  136 | 255 |

4. Expression of the Recombinant Proteins:

4.1—Transformation

Transformation of *Escherichia coli* T7 Express with plasmid DNA was carried out by standard methods with $CaCl_2$-treated cells (Hanahan D. <<Plasmid transformation by Simanis.>> In Glover, D. M. (Ed), DNA cloning. IRL Press London. (1985): p. 109-135.).

| Recombinant plasmids ID | Host strain | Plate agar |
|---|---|---|
| LVL489, LVL490, LVL491, LVL511, LVL512, LVL513 and LVL514 | T7 Express[A] | LB + agar-1.5%[B] 40 µg/ml kanamycin[C] |

[A]NEB (catalogue number C2566H)
[B]BBL ™ Select APS ™ LB broth base, BD, MD, USA (catalogue number: 292438); Agar, Laboratoire MAT, QC, Canada (catalogue number: AP-0108)
[C]Sigma, ON, Canada (catalogue number: K-4000)

4.2—Culture

Confluent agar plate inoculated with *Escherichia coli* T7 Express+plasmid from transformation (section 5.1) was stripped, ressuspended in culture media and used to inoculate 800 ml of LB broth (BD)±1% (w/v) glucose (Laboratoire MAT, catalogue number: GR-0101)+antibiotic (as described in section 5.1) to obtain $O.D._{600\ nm}$ between 0.1 and 0.2.

Cultures were incubated at 37° C., 250 RPM until an $O.D._{600\ nm}$ around 0.8. At this time, 1 ml of each culture was collected, centrifuged at 14 000 RPM for 5 minutes and supernatants/pellets were frozen at −20° C. separately.

4.3—Induction

At $O.D._{600\ nm}$ around 0.8, the cultures T7 Express were cooled down (−20° C., 20 minutes) before inducing the expression of the recombinant protein by addition of 1 mM isopropyl 6-D-1-thiogalactopyranoside (IPTG; EMD Chemicals Inc., catalogue number: 5815) and incubated overnight at 22° C., 250 RPM.

4.4—Preparation of Samples after Induction

After the overnight induction (around 16 hours), $O.D._{600\ nm}$ was evaluated after induction and culture was centrifuged at 14 000 RPM for 5 minutes and supernatant/pellets were frozen at −20° C. separately.

5. Purification:

Bacterial pellet was resuspended in 20 mM bicine buffer (pH 8.0) containing 500 mM NaCl and a mixture of protease inhibitor (Complete, Roche). Bacteria were lysed using a Constant System 1.1 KW 2×30 000 PSI. Soluble (supernatant) and insoluble (pellet) components were separated by centrifugation at 20 000 g for 20 min at 4° C.

The 6-His tagged-protein was purified under native conditions on IMAC using Profinia standard protocol (flow rate: 2 ml/min). The soluble components were loaded on a 5 ml His Trap column (BioRad) preequilibrated with the same buffer used to bacterial resuspension. After loading on the column, the column was washed with the same buffer. We used 20 mM bicine buffer (pH 8.0) containing 500 mM NaCl, 10 mM imidazole for the second wash. Elution was performed using a 20 mM bicine buffer (pH 8.0) containing 500 mM NaCl and 250 mM imidazole. Proteins were dialysed using PBS 1× pH 7.4 and dosing was determined using DC Protein Assay of BioRad.

SDS-Paqe:
Gel: NuPAGE 4-12% Bis-Tris Gel 1.0 mm×15 wells (Invitrogen catalog number: NP0323BOX)

Preparations of samples, buffers and migration conditions were done under conditions recommended by the suppliers (Invitrogen).

Western Blot:
Preparations of buffer and migration conditions were done under conditions recommended by the suppliers (Invitrogen).

Membranes were blocked for 30 minutes at 37° C., 60 RPM using 3% milk/PBS 1× fresh solution. After the blocking incubation, Primary Antibodies were added consisting to α-6×His Tag (AbCam, catalogue number: ab9108-100) or α-fHbpA (200802032 pool g2, 18/06/08 D42) at dilution: 1:1000 or 1:400 respectively in 3% milk/PBS 1× fresh solution for 1 hour at 37° C., 60 RPM. After that, membranes were washed three times 5 minutes at room temperature using 0.02% Tween 20/PBS 1×. Secondary Antibodies were added using a goat anti-rabbit alkaline phosphatase (Jackson laboratory, catalogue number: 111-055-144) at dilution 1:14 000 or a Goat alkaline phoaphatase anti-IgG+IgM (H+L) mouse (Jackson laboratory, catalogue number: 115-055-068)) at dilution 1:6 000 in 3% milk/PBS 1× fresh solution. Membranes were incubated for 1 hour at 37° C., 60 RPM. After that, membranes were washed three times 5 minutes at room temperature using 0.02% Tween20/PBS 1× before the membrane expositions to Alkaline Phosphatase substrate (Sigma Fast NBT/BCIP, catalogue number:B5655-25TAB) under conditions recommended by the suppliers.

Example 2

Fusion Protein A

This fusion comprises a part of the family B MC58 mature protein sequence (from residue 1 to residue 135) and a part of the family A 8047 mature protein sequence (from residue 136 to residue 254). In this fusion, 2 residues (Glu217 and Thr238), identified by M. C. Schneider et al. as involved in the factor H-binding function of the protein, are mutated in Alanine.

These mutations in the nucleic sequence:
Codon GAA (nT 649, Glu217) is mutated in codon GCA (Ala217, *)

Codon ACC (nT 712, Thr238) is mutated in codon GCC (Ala238; *)

Sequence of this fusion—SEQ ID No.18 (length: 254 aa):

```
  1  MHHHHHHVAA DIGAGLADAL TAPLDHKDKG LQSLTLDQSV RKNEKLKLAA

51  QGAEKTYGNG DSLNTGKLKN DKVSRFDFIR QIEVDGQLIT LESGEFQVYK

101  QSHSALTAFQ TEQIQDSEHS GKMVAKRQFR IGDIAGEHTA FNQLPDGKAE

151  YHGKAFSSDD AGGKLTYTID FAAKQGHGKI EHLKTPEQNV ELAAAELKAD

*                       *

201  EKSHAVILGD TRYGSEAKGT YHLALFGDRA QEIAGSAAVK IGEKVHEIGI

251  AGKQ
```

The underlined sequence is the family B sequence coming from strain MC58. The other part of the fusion is the family A sequence coming from strain 8047.

Corresponding nucleic sequence (SEQ ID No. 19):

```
ATGCATCATCATCACCATCATGTTGCAGCAGATATTGGCGCAGGTCTGGCAGATGCACTGACCGCTCCGCTGGATCA

TAAAGATAAAGGTCTGCAGAGCCTGACCCTGGATCAGAGCGTTCGCAAAAATGAAAAACTGAAACTGGCAGCACAGG

GTGCAGAAAAAACCTATGGTAATGGCGATAGCCTGAATACCGGCAAACTGAAAAATGATAAAGTGAGCCGCTTTGATT

TTATTCGCCAGATTGAAGTTGATGGTCAGCTGATTACCCTGGAAAGCGGTGAATTTCAGGTGTATAAACAGAGCCATA

GCGCACTGACCGCCTTTCAGACCGAACAAATTCAGGATAGCGAACATAGCGGTAAAATGGTTGCCAAACGCCAGTTT

CGTATTGGTGATATTGCCGGTGAACATACCGCATTTAATCAGCTGCCGGATGGTAAAGCAGAATATCATGGCAAAGC

CTTTAGCTCTGATGATGCCGGTGGTAAACTGACCTATACCATTGATTTTGCAGCCAAACAGGGTCATGGCAAAATTGA

ACATCTGAAAACACCGGAACAGAATGTTGAACTGGCAGCAGCAGAACTGAAAGCAGATGAAAAAAGCCATGCCGTTA
```

```
TTCTGGGTGATACCCGTTATGGTAGCGAAGCAAAAGGCACCTATCATCTGGCACTGTTTGGTGATCGTGCACAGGAA

ATTGCAGGTAGCGCAGCAGTTAAAATTGGCGAAAAAGTGCATGAAATTGGCATTGCCGGTAAACAG
```

Example 3

Fusion Protein B (SEQ ID NOS. 20 and 21)

Given that the Glu238 is not conserved in all strains that can bind the factor H, this residue is potentially not critical for this binding. Thus a fusion protein B is proposed.

This fusion is based on fusion A in which only the amino acid Glu217 (conserved in all analysed strains and very probably involved in the factor H-binding) is mutated in Ala217.

Example 4

Fusion Protein C

This fusion based on fusion A, further including some mutations were introduced to restore the family B MAb502 epitope that is lost in fusions A and B.

The residues Glu146→Arg149 and Arg204 of family B mature protein sequence were identified as key residues for MAb502 recognition.

The residue Gly147 is already present in the fHbp family A mature protein sequence. The amino acids Asp146, Lys148 and Ser203 of fHbp family A protein sequence are replaced by Glu146, Arg149 and Arg204, respectively. Moreover, a Glycine is introduced at position 147.

The mutations in the nucleic sequence:
Asp146→Glu146: GAC→GAA (nT 436)
Addition of Gly147: GGC (nT 439)
Lys148→Arg149: AAA→AGG (nT 445)
Ser203→Arg204: TCA→CGT (nT 610)

Sequence of the fusion (length: 255 aa) (SEQ ID No. 22):

```
  1 MHHHHHHVAA DIGAGLADAL TAPLDHKDKG LQSLTLDQSV RKNEKLKLAA
 51 QGAEKTYGNG DSLNTGKLKN DKVSRFDFIR QIEVDGQLIT LESGEFQVYK
101 QSHSALTAFQ TEQIQDSEHS GKMVAKRQFR IGDIAGEHTA FNQLPEGGRA
151 EYHGKAFSSD DAGGKLTYTI DFAAKQGHGK IEHLKTPEQN VELAAAELKA
201 DEKRHAVILG DTRYGSEAKG TYHLALFGDR AQEIAGSAAV KIGEKVHEIG
251 IAGKQ
```

Corresponding nucleic sequence (SEQ ID No. 23):

```
ATGCATCATCATCACCATCATGTTGCAGCAGATATTGGCGCAGGTCTGGCAGATGCACTGAC

CGCTCCGCTGGATCATAAAGATAAAGGTCTGCAGAGCCTGACCCTGGATCAGAGCGTTCGC

AAAAATGAAAAACTGAAACTGGCAGCACAGGGTGCAGAAAAAACCTATGGTAATGGCGATAG

CCTGAATACCGGCAAACTGAAAAATGATAAAGTGAGCCGCTTTGATTTTATTCGCCAGATTGA

AGTTGATGGTCAGCTGATTACCCTGGAAAGCGGTGAATTTCAGGTGTATAAACAGAGCCATA

GCGCACTGACCGCCTTTCAGACCGAACAAATTCAGGATAGCGAACATAGCGGTAAAATGGTT

GCCAAACGCCAGTTTCGTATTGGTGATATTGCCGGTGAACATACCGCATTTAATCAGCTGCC

GGAAGGTGGTCGTGCAGAATATCATGGCAAAGCCTTTAGCTCTGATGATGCCGGTGGTAAA

CTGACCTATACCATTGATTTTGCAGCCAAACAGGGTCATGGCAAAATTGAACATCTGAAAACA

CCCGGAACAGAATGTTGAACTGGCAGCAGCAGAACTGAAAGCAGATGAAAAACGTCATGCCG

TTATTCTGGGTGATACCCGTTATGGTAGCGAAGCAAAAGGCACCTATCATCTGGCACTGTTT

GGTGATCGCGCACAGGAAATTGCAGGTAGCGCAGCAGTTAAAATTGGCGAAAAAGTGCATG

AAATTGGCATTGCCGGTAAACAG
```

Example 5

Proposed Fusion Protein D

Fusion protein D Is based on fusion C in which only the amino acid Glu218, involved in the factor H-binding, is mutated in Ala218.

Example 6

Fusion Protein E

This fusion is based in fusion protein C. Some additional residues were identified as potentially involved in the MAb502 recognition. There are Pro145, Phe227, Gly228, Lys230 and Glu233 in the family B mature protein sequence.

To test the role of these residues, the fusion E was proposed, it is the fusion C in which these residues were inserted.

To restore all these potentially interesting residues in the fusion, only one codon mutation must be done on the fusion protein C construct: Arg230 in the family A mature protein sequence (strain 8047) must be mutated in Lys230.

Sequence of the fusion—SEQ ID NO. 24 (length: 255 aa):

```
  1  MHHHHHHVAA DIGAGLADAL TAPLDHKDKG LQSLTLDQSV RKNEKLKLAA
 51  QGAEKTYGNG DSLNTGKLKN DKVSRFDFIR QIEVDGQLIT LESGEFQVYK
101  QSHSALTAFQ TEQIQDSEHS GKMVAKRQFR IGDIAGEHTA FNQLPEGGRA
151  EYHGKAFSSD DAGGKLTYTI DFAAKQGHGK IEHLKTPEQN VELAAAELKA
201  DEKRHAVILG DTRYGSEAKG TYHLALFGDK AQEIAGSAAV KIGEKVHEIG
251  IAGKQ
```

The mutations in the nucleic sequence:
Arg230→Lys230: CGC→AAA (nT 688)
Corresponding nucleic sequence (SEQ ID No. 25):

```
ATGCATCATCATCACCATCATGTTGCAGCAGATATTGGCGCAGGTCTGGCAGATGCACTGAC

CGCTCCGCTGGATCATAAAGATAAAGGTCTGCAGAGCCTGACCCTGGATCAGAGCGTTCGC

AAAAATGAAAAACTGAAACTGGCAGCACAGGGTGCAGAAAAAACCTATGGTAATGGCGATAG

CCTGAATACCGGCAAACTGAAAAATGATAAAGTGAGCCGCTTTGATTTTATTCGCCAGATTGA

AGTTGATGGTCAGCTGATTACCCTGGAAAGCGGTGAATTTCAGGTGTATAAACAGAGCCATA

GCGCACTGACCGCCTTTCAGACCGAACAAATTCAGGATAGCGAACATAGCGGTAAAATGGTT

GCCAAACGCCAGTTTCGTATTGGTGATATTGCCGGTGAACATACCGCATTTAATCAGCTGCC

GGAAGGTGGTCGTGCAGAATATCATGGCAAAGCCTTTAGCTCTGATGATGCCGGTGGTAAA

CTGACCTATACCATTGATTTTGCAGCCAAACAGGGTCATGGCAAAATTGAACATCTGAAAACA

CCGGAACAGAATGTTGAACTGGCAGCAGCAGAACTGAAAGCAGATGAAAAACGTCATGCCG

TTATTCTGGGTGATACCCGTTATGGTAGCGAAGCAAAAGGCACCTATCATCTGGCACTGTTT

GGTGATAAAGCACAGGAAATTGCAGGTAGCGCAGCAGTTAAAATTGGCGAAAAAGTGCATG

AAATTGGCATTGCCGGTAAACAG
```

Example 7

Proposed Fusion Protein F

It is based on fusion E in which only the amino acid Glu218, involved in the factor H-binding, is mutated in Ala218.

Example 8

Effect of Antibodies Against fHbp on ST269 Clonal Complex Methods

Antigen Preparations

Recombinant fHBPs variants (v) A and B were produced in BL21 (DE3) *E. coli* after IPTG induction and purification using IMAC column. The fhbp sequences were derived from strains MC58 (fHBP B) and 2996 (fHBP A). Genes were cloned in pET24b plasmid without the nucleotide sequence corresponding to the leader sequence and with a His-Tag in C-ter.

Animal Procedures:

Groups of 10-30 mice were immunized three times by the intramuscular (IM) route on day 0, 21 and 28. Each injection contained 5 μg of monovalent fHBP vaccine (fHBP A or fHBP B) adsorbed onto $Al(OH)_3$. On day 42, blood samples were taken for serum. Mice sera were from experiments 20080790 and 20090265.

Groups of 10 guinea-pigs were immunized three times by the intramuscular (IM) route on day 0, 14 and 28. Each injection contained either OMV antigen normalized to 10 μg of protein and formulated with $AlPO_4$. On day 42, blood samples were taken for serum. Guinea pig sera were from experiments 20090266.

SBA

*N. meningitidis* strains were cultivated overnight on Petri Dishes at 37° C.+5% $CO_2$. They were sub-cultured for 4 hours on Petri Dishes without or with 20 μM TPEN (zinc chelator) 37° C.+5% $CO_2$. Serum samples (pooled sera) were inactivated for 40 min at 56° C. and then diluted 1/10 or 1/50 in PBS-glucose 0.1% and then twofold diluted in a volume of 25 μl in flat bottom microplates. Then 25 μl of a mix of bacteria, from agar-plate culture or after cell contact (diluted in PBS-glucose 0.1% to yield ~100-150 CFU per well) and baby rabbit complement (final concentration in microwell: 12.5% v/v) was added to the serum dilution. After 75 min of incubation at 37° C. under shaking, 2 layers of agar (0.9%) were added to the wells. The microplates were incubated overnight at 35 or 37° C.+$CO_2$. The CFU's were counted and the percentage of killing was calculated. The SBA titer is the dilution giving 50% of killing.

Two strains from the clonal complex ST269 were used: M01-240013 and M01-240101. Both strains were isolated in UK in 2001.

Results

Anti-fHbpB sera were tested in SBA with strain expressing the fHbp family B (M01-240101), while anti-fHbpA sera were used in SBA against strain expressing the fHbp from family A (M01-240013). SBA were performed in absence or presence of TPEN.

Only one strain was killed by anti-fHbp antibodies (strain M01-240101) in presence of complement. The second strain, M01-240013 is not killed by anti-fHbp antibodies. As observed, bactericidal culture condition (absence or presence of TPEN) has no impact on SBA titers.

TABLE 1 bactericidal titer of anti-fHbp antibodies in presence of baby rabbit complement

| Strain | M01-240101 | M01-240013 |
|---|---|---|
| fHbp family | B | A |
| fHbp expression | + | + |
| SBA titer without TPEN | | |
| Anti-fHbp B | 494 | Not tested |
| Anti-fHbpA | Not tested | 50 |
| SBA titer with TPEN | | |
| Anti-fHbp B | 509 | Not tested |
| Anti-fHbpA | Not tested | 50 |

Conclusion

Anti-fHbp antibodies were not able, alone, to provide effective killing of M01-240013 strain (from clonal complex ST269)

Example 9

L2 *N. meningitidis* Strains Express Lower Level of FHbp than Strains Producing a LOS Containing a L3-Like Inner Core Methods Antigen Preparations Recombinant fHBPs variants (v) A and B were produced in BL21 (DE3) *E. coli* after IPTG induction and purification using IMAC column. The fhbp sequences were derived from strains MC58 (fHBP B) and 2996 (fHBP A). Genes were cloned in pET24b plasmid without the nucleotide sequence corresponding to the leader sequence and with a His-Tag in C-ter. Recombinant nadA was also produced in BL21 *E. coli* and the sequence was derived from strain 2996.

Animal Procedures:

Groups of 30 OF1 mice were immunized three times by the intramuscular (IM) route on day 0, 21 and 28 with purified recombinant proteins adsorbed onto $Al(OH)_3$. On day 42, blood samples were taken for serum. Mice sera were from experiments 20080232.

Western Blot with Whole Cell Preparations

*N. meningitidis* strains were cultivated overnight on MH agar plates at 37° C.+5% $CO_2$. They were sub-cultured for 4 hours on MH agar plates with 20 μM TPEN (zinc chelator) 37° C.+5% $CO_2$. Inactivation was performed by incubating the cells harvested from agar plates in PBS-PMSF (200 μM)-azide (0.2%) ON at 37° C. Inactivated cells were then washed in PBS and frozen at −20° C.

Ten microgram of cell preparations were loaded per wells and proteins were separated under reducing condition using 12% gels (Novex), and then the proteins were transferred onto nitrocellulose membranes. After blocking non-specific binding sites, the membranes were incubated 2 h with a mix of sera from mice immunized with either fHBP A, fHBP B or NadA. For TdfI detection, the membranes were incubated either with anti-TdfI rabbit serum or a mix of 4 anti-TdfI Mabs. After washing, membranes were incubated with anti-mouse Ig biotinylated antibodies (Amersham). Binding of antibodies was detected using streptavidine-peroxidase conjugate (Amersham).

For each strain the level of expression of fHBP, TdfI and NadA was assessed by Western-Blot. Expression level was scored as followed: high level of expression, ++; intermediate expression level, +; low expression level, +/− and non-detectable expression, − as exemplified in FIG. 3.

Identification of fhbp Alleles:

For most strains, fHbp allele was determined by PCR typing as described by Beerninck and collaborators in 2006. For some strains, the complete fhbp locus was amplified from crude MenB lysate by PCR with primers. The PCR fragment was then purified with High Pure PCR Purification Kit (Roche) and sequenced by the Sanger method. The sequence type (family A or B) was deduced after comparison with family A and B reference sequences (2996 and MC58 respectively) using Lasergene MegAlign-ClustalX software as described in Fletcher et al, 2004.

LOS Inner-Core Compositions

LOS inner-core compositions were deduced after analysis of presence/functionality of Ipt3, Ipt6, lot3/oac1 and IgtG genes with the following rules:

if lot3/oac1 is present and IN phase, GlcNAc is O-acetylated if IgtG is present and IN phase, glucose linked on position 3 of HepII.

if Ipt6 is present, PEA linked on position 6 of HepII if Ipt3 is present and IgtG absent or OUT phase ▶ PEA linked on position 3 of HepII if Ipt3 is present and IgtG IN phase ▶ no PEA linked on position 3 of HepII if Ipt3 is absent ▶ no PEA linked on position 3 of HepII The following nomenclature was used to characterized the different inner-core structure:

L3=one PEA on position 3 of HepII with or without additional Acetyl on inner core GlcNAc. Such inner-core is associated with the following LOS immunotypes: L1, L3, L7, L8

L2=one PEA on position 6 and one glucose on position 3 of HepII and one additional Acetyl on inner core GlcNAc L3v=two PEA's on HepII (on positions 3 and 6) and in general one additional Acetyl on inner core GlcNAc L5=one glucose on position 3 of HepII and one additional Acetyl on inner core GlcNAc LX=no PEA or Glucose on position 3 and 6 of HepII and one additional Acetyl on inner core GlcNAc Results The LOS inner core of 155 strains was typed by molecular method (Table 1 below). These strains were either selected randomly amongst disease isolates recently isolated (after 2004) in UK (n=53), Germany (n=40) and Spain (n=47).

or isolated before 2002 from patients in 5 different countries (n=15).

Among the 140 recently isolates, the majority of strains produce an L3 inner-core (from 66 to 94%). A L2 inner-core is observed in 2 and 2.5% of English and German strains respectively while it is found in more than 17% of Spanish strains.

Among the 155 clinical isolates, 52 strains were analysed for fHBP and NadA gene occurrence, allele and fHBP, NadA, TdfI expression. These 52 were selected as followed: the 15 strains isolated before 2002, 10 randomly selected recent isolates per country (UK, Germany and Spain), and all recent L2 (Table 2 below).

The fhbp gene is present in all the 52 strains, 62% (32/52) of strains possess the allele B and 38% (20/52) the allele A.

There are no apparent association between the inner-core LOS type and fhbp allele as the fhbp B allele is detected in 68% (21/31) and 60% (9/15) of L3 and L2 strains, respectively There are no apparent association between the fHBP allele and the fHBP expression since fHBP is well expressed (+ or ++) in 50% and 62% of strains possessing the fhbp A allele and the fhbp B allele, respectively.

However, while only 19% (6/31) of L3 strains produce low or undetectable level of fHBP, low/null expression of fHBP was observed for 93% (14/15) of L2 strains.

Further it was found that many of the strains of L2 immunotype were also of ST11 clonal complex.

The nadA gene is present in 44% of analyzed strains (23/52) but only 25% of strains express detectable amount of NadA by Western Blot (13/52).

In contrast to fHBP expression, there are no relation between the LOS inner-core and the expression of NadA. Indeed, only 16% of L3 and 27% of L2 strains produce detectable amount of NadA.

Among the 22 of the 52 strains that express no or low level of fHBP, only 4 express detectable level of NadA.

The expression of TdfI was analyzed using a mix of four monoclonal antibodies directed against TdfI and/or a polyclonal serum from rabbit immunized with recombinant TdfI. Among the 51 strains tested, 94% express detectable amount of TdfI (48/51).

Among the 22 strains expressing low or undectable level of fHBP, all but one produces TdfI. This strain does not possess the nadA gene.

Conclusion

The results suggest that L2 strains tend to produce significantly lower level of fHBP than strain expressing a L3 inner-core LOS. This observation argues against a MenB vaccine based only on fHBP, especially in countries such as Spain where L2 strains represent 17% of recent clinical isolates. In addition, all the Spanish L2 strains tested do not express detectable amount of NadA.

Among the 22 strains that express no or low level of fHBP, only 4 express detectable level of NadA while all but one express TdfI.

TABLE 1

Inner-core typing of the 155 invasive menB strains (including 140 recently isolated)

| | L3 (%) | L2 (%) | L3V (%) | other (%) |
|---|---|---|---|---|
| Germany (n = 40) | 85 | 2.5 | 5 | 7.5 |
| UK (n = 53) | 94 | 2 | 0 | 4 |
| Spain (n = 47) | 66 | 17 | 13 | 4 |
| All (n = 140) | 82 | 7 | 6 | 5 |
| Others (n = 15) | 60 | 33 | 7 | 0 |

TABLE 2

Characteristics of the 52 strains analyzed: LOS inner-core type, fhpb allele (gene), level of expression of fHBP, Presence of nadA gene, level of expression of NadA, expression of TdfI (using MAbs and/or rabbit serum).

| Strains | Country | LOS (inner-core typing) | fHBP (gene) | fHBP WB | NadA (gene) | NadA WB | TdfI WB (MAbs/rabbit PAb) |
|---|---|---|---|---|---|---|---|
| M97-250687 | UK | L3 | B | ++ | + | + | + |
| M01-240013 | UK | L3 | A | + | − | − | + |
| M01-240101 | UK | L3 | B | + | − | − | + |
| M01-240149 | UK | L3 | B | + | − | − | + |
| M01-240185 | UK | L3 | B | + | + | − | NT |
| M01-240355 | UK | L3 | A | + | − | − | + |
| M05-0240072 | UK | L2 | B | − | + | − | + |
| M05-0240210 | UK | L3 | B | + | − | − | + |
| M05-0240471 | UK | L3 | B | +/− | − | − | + |
| M05-0240697 | UK | L3 | B | + | − | − | + |
| M05-0241043 | UK | L3 | B | + | − | − | + |
| M05-0241255 | UK | L3 | A | + | − | − | + |
| M06-0240116 | UK | L3 | B | + | − | − | + |
| M06-0240359 | UK | L3 | A | − | − | − | + |
| M06-0240707 | UK | L3 | A | − | − | − | − |
| M06-0240928 | UK | L3 | A | + | − | − | + |
| DE10038_05 | Germany | L3 | B | + | − | − | + |
| DE10250_05 | Germany | L3 | B | + | − | − | + |
| DE10302_05 | Germany | L3v | A | + | + | +/− | − |
| DE10410_05 | Germany | LX | A | − | + | − | + |
| DE10427_05 | Germany | L2 | A | + | + | +++ | − |
| DE10461_06 | Germany | L5 | B | ++ | + | + | + |
| DE10523_06 | Germany | L3 | B | + | − | − | + |
| DE10561_06 | Germany | L3 | B | + | − | − | + |
| DE10620_06 | Germany | L3 | A | +/− | − | − | + |
| DE10674_06 | Germany | L3 | A | + | − | − | + |
| DE10690_06 | Germany | L3 | B | +/− | − | − | + |
| DE10772_06 | Germany | L3 | B | + | + | + | + |
| 17540 | Spain | L2 | B | − | + | − | + |
| 17607 | Spain | L3 | B | ++ | + | ++ | + |
| 17639 | Spain | L2 | B | +/− | + | − | + |
| 17662 | Spain | L3v | A | + | − | − | + |
| 17710 | Spain | L3 | A | ++ | − | − | + |
| 17763 | Spain | L2 | B | +/− | + | − | + |
| 17787 | Spain | L2 | B | +/− | + | − | + |
| 17810 | Spain | L3 | A | + | − | − | + |
| 17908 | Spain | L2 | B | +/− | + | − | + |
| 17938 | Spain | L3 | B | ++ | + | ++ | + |
| 17981 | Spain | L2 | B | +/− | − | − | + |
| 18025 | Spain | L5 | B | ++ | + | +/− | + |
| 18064 | Spain | L3 | B | ++ | + | + | + |
| 18082 | Spain | L2 | B | +/− | + | − | + |
| 18116 | Spain | L2 | B | +/− | + | − | + |
| BZ232 | The Netherlands | L2 | A | +/− | − | − | + |
| 760676 | The Netherlands | L2 | A | − | + | + | + |
| H44/76 | Norway | L3 | B | ++ | − | − | + |
| N98/254 | NZ | L3 | B | + | − | − | + |
| NZ124 | NZ | L3 | B | +/− | − | − | + |
| 2986 | US? | L2 | A | − | + | ++ | + |
| 3356 | US? | L2 | A | − | − | − | + |
| 6275 | US | L3v | A | − or +/− | + | ++ | + |
| B16B6 | US | L2 | A | − | + | +/− | + |

Example 10

Improvement of the Efficacy of fHBP Based Vaccine by Addition of TdfI

Methods
Antigen Preparations

Recombinant fHBPs variants (v) A and B were produced in BL21 (DE3) E. coli after IPTG induction and purification using IMAC column. The fHbp sequences were derived from strains MC58 (fHBP B) and 2996 (fHBP A). Genes were cloned in pET24b plasmid without the nucleotide sequence corresponding to the leader sequence and with a His-Tag in C-ter.

Animal Procedures:

Groups of 10-30 mice were immunized three times by the intramuscular (1M) route on day 0, 21 and 28. Each injection contained either OMV antigen normalized to 5 ug of protein and formulated with AS04 Adjuvant System (AIPO4 plus 3-O-desacyl-4' monophosphoryl lipid A) or with monovalent fHBP vaccine (fHBP A or fHBP B) adsorbed onto Al(OH) or bivalent fHbpA+B vaccine. On day 42, blood samples were taken for serum. Mice sera were from experiments 20040652, 20070371 and 20080083.

Western Blot with Whole Cell Preparations

N. meningitidis strains were cultivated overnight on MH agar plates at 37° C.+5% CO2. They were subcultured for 4 hours on MH agar plates with 20 μM TPEN (zinc chelator) 37° C.+5% CO2. Inactivation was performed by incubating the cells harvested from agar plates in PBS-PM SF (200 μM)-azide (0.2%) ON at 37° C. Inactivated cells were then washed in PBS and frozen at −20° C.

Ten microgram of cell preparations were loaded per wells and proteins were separated under reducing condition using 12% gels (Novex), and then the proteins were transferred onto nitrocellulose membranes. After blocking non-specific binding sites, the membranes were incubated 2 h with a monoclonal antibody directed against TdfI or with a mix of sera from mice immunized with either fHBP A or fHBP B sera. After washing, membranes were incubated with anti-mouse Ig biotinylated antibodies (Amersham). Binding of antibodies was detected using streptavidine-peroxidase conjugate (Amersham).

For each strain the level of expression of fHBP was assessed by Western-Blot. Expression level was scored as followed: high level of expression, ++; intermediate expression level, +; low expression level, +/−; non-detectable expression, −.

SBA

N. meninigitidis strains were cultivated overnight on Petri Dishes at 37° C.+5% CO. They were sub-cultured for 4 hours on Petri Dishes without or with 20 μM TPEN (zinc chelator) 37° C.+5% CO2. Serum samples (pooled sera) were inactivated for 40 min at 56° C. and then diluted 1110 or 1150 in PBS-glucose 0.1% and then twofold diluted in a volume of 25 μL in flat bottom microplates. Then 25 μL of a mix of bacteria (diluted in PBS-glucose 0.1% to yield ~100-150 CFU per well) and baby rabbit complement (final concentration in microwell: 12.5% v/v) was added to the serum dilution. After 75 min of incubation at 37° C. under shaking, 2 layers of agar (0.9%) were added to the wells. The microplates were incubated overnight at 35 or 37° C.+CO2. The CFU's were counted and the percentage of killing was calculated. The SBA titer is the dilution giving 50% of killing.

Identification of fhbp Alleles:

The complete fhbp locus was amplified from crude MenB lysate by PCR with primers. The PCR fragment was then purified with High Pure PCR Purification Kit (Roche) and sequenced by the Sanger method. The sequence type (variant 1, 2 or 3) was deduced after comparison with variant 1, 2 and 3 references sequences using Lasergene MegAlign-ClustaiX software.

Results

Different N. meninigitidis strains were tested in SBA using sera from mice immunized with monovalent fHbp vaccine (fHbp A or fHbp B) or a bivalent fHbp vaccine (fHbp A+B). These strains were selected based on the expression level of fHbp determined by Western blot and by their fHbp allele. The results (Table 3 below) clearly indicate that fHbp is not able to induce a cross-protective fHbp response since sera from mice immunized with fHbp B are not bactericidal against strains producing a fHbp A proteins (and the reverse was also observed). Sera from mice immunized with fHBPA and fHBP B elicited the production of bactericidal antibodies capable to mediate the complement killing of strains expressing either the fHbp A or the fHbp B protein. In addition, the level of expression of fHbp by the targeted SBA strain impact also on the bactericidal titers: lower is the fHbp expression level lower are the bactericidal titers. These results illustrate the need to improve a vaccine based on fHbp by adding other antigens in order to protect against strains producing low or non-detectable level of fHbp.

TABLE 3

Serum bactericidal titers of anti-fHBP mice sera against a panel of N meningitidis strains expressing different fHBP proteins at different level.

| | H44/76 fHbp B (++) | NZ98/124 fHbp B (+/−) | 608B fHbpB (−) | S3446 fHbp A (+/−) | 760676 fHbpA (−) |
|---|---|---|---|---|---|
| Ctrl sera | <50 | <50 | <50 | <50 | <50 |
| anti-fHbp (B) sera | >2560 | 309 | <50 | <50 | <50 |
| anti-fHbp (A) sera | 125 | 60 | <50 | 396 | <50 |
| anti-fHbp (A&B) sera | >2560 | 221 | <50 | 1104 | <50 |

Mice were immunized with different OMV preparations obtained from recombinant H44/76 strains having a common background: porA KO, galE LOS and capsule minus. The different preparations are differentiated by the level of TdfI and fHbp. Control OMVs (Ctrl OMVs) had no detectable amount of TdfI and fHbp. TdfI OMVs were produced from a strain that overexpressed TdfI and TdfI-fHBPOMVs displayed both TdfI and fHbp. The sera were analysed in SBA using a panel of H44/76 strains expressing different level of TdfI. The wild type (WT) strain did not express any detectable amount of TdfI while a recombinant H44/76 strain transformed with the pfP10 plasmid containing the TdfI gene under the pTac promoter produced high level of TdfI in presence of ITPG (IPTG) (Table 4 below).

The sera from mice immunized with the control preparation (Ctrl-OMVs) were not bactericidal. Only the strain expressing high amount of TdfI (IPTG) was killed by anti-TdfI antibodies in presence of complement. By contrast, sera from mice immunized with TdfI-fHbp OMV preparation mediated the complement killing of the two H44/76 strains, via the presence of anti-fHbp antibodies and as observed there was a correlation between the bactericidal titer and the level of TdfI produced by the targeted strains (Table 4 below).

TABLE 4

Serum bactericidal titers on different H44176 strains producing different level of TdfI (wild type, WT; or overproducing TdfI via IPTG induction; IPTG).

| SBA titers | WT | IPTG |
|---|---|---|
| anti-Ctrl OMV sera | 50 | 50 |
| anti-TdfI OMV sera | 50 | 679 |
| anti-TdfI-fHbp OMV sera | 592 | 1146 |

Example 11

Improvement of the Efficacy of fHBP Based Vaccine by Addition of TdfI

Methods

Antigen Preparations

Outer membranes vesicles (OMVs) were produced using classical 0.5% DOC extraction from different recombinant H44/76 strains (porA KO, capsule minus, galE LOS and over-producing different outer-membrane proteins).

Recombinant fHBPs variants (v) A and B were produced in BL21 (DE3) *E. coli* after IPTG induction and purification using IMAC column. The fhbp sequences were derived from strains MC58 (fHBP B) and 2996 (fHBP A). Genes were cloned in pET24b plasmid without the nucleotide sequence corresponding to the leader sequence and with a His-Tag in C-ter.

Animal Procedures:

Groups of 10-30 mice were immunized three times by the intramuscular (IM) route on day 0, 21 and 28. Each injection contained 5 μg of monovalent fHBP vaccine (fHBP A or fHBP B) adsorbed onto Al(OH)$_3$. On day 42, blood samples were taken for serum. Mice sera were from experiments 20080790 and 20090265.

Groups of 10 guinea-pigs were immunized three times by the intramuscular (IM) route on day 0, 14 and 28. Each injection contained either OMV antigen normalized to 10 μg of protein and formulated with AlPO$_4$. On day 42, blood samples were taken for serum. Guinea pig sera were from experiments 20090266.

SBA

N. meningitidis strains were cultivated overnight on Petri Dishes at 37° C.+5% CO$_2$. They were sub-cultured for 4 hours on Petri Dishes without or with 20 μM TPEN (zinc chelator) 37° C.+5% CO$_2$. Serum samples (pooled sera) were inactivated for 40 min at 56° C. and then diluted 1/10 or 1/50 in PBS-glucose 0.1% and then twofold diluted in a volume of 25 μl in flat bottom microplates. Then 25 μl of a mix of bacteria, from agar-plate culture or after cell contact (diluted in PBS-glucose 0.1% to yield −100-150 CFU per well) and baby rabbit complement (final concentration in microwell: 12.5% v/v) was added to the serum dilution. After 75 min of incubation at 37° C. under shaking, 2 layers of agar (0.9%) were added to the wells. The microplates were incubated overnight at 35 or 37° C.+CO$_2$. The CFU's were counted and the percentage of killing was calculated. The SBA titer is the dilution giving 50% of killing.

Results

Anti-fHbpB sera were tested in SBA with strains expressing the fHbp family B, while anti-fHbpA sera were used in SBA against strains expressing the fHbp from family A. Sera from guinea-pigs immunized with OMVs (blebs) produced from a strain over-expressing TdfI were tested against both fHbpB and fHbpA strains.

Anti-TdfI and anti-fHbp sera were tested alone or were mixed before to perform SBA in presence or absence of TPEN.

A panel of 16 strains was used in SBA. Among those, 5 to 7 were killed by anti-fHbp antibodies (pending the absence or presence of TPEN in SBA culture condition) (SBA titer >128). In absence of TPEN, only 3 strains were killed by sera from guinea-pig immunized with TdfI-blebs while in presence of TPEN, 12 strains were killed.

When anti-fHbp and anti-TdfI blebs sera are mixed, there is a general trend to improve the SBA titers, showing at least an additive impact of anti-fHBp and anti-TdfI blebs serum bactericidal activity.

TABLE 5

| | | | | | | | Strain | | | | | | | | |
|---|---|---|---|---|---|---|---|---|---|---|---|---|---|---|---|
| | H44/76 | MC58 | NZ98/ 294 | M01-240101 | DE 10690-06 | M01-240149 | 18025 | M01-240013 | M01-240395 | M05-0240471 | 760675 | 17540 | M05-0240072 | M98-250771 | |
| serogroup | B | B | B | B | B | B | B | B | B | B | B | B | B | B | |
| immuntype | L3 | L3 | L3 | L3 | L3 | L2 | L3 | L3 | L3 | L3 | L2 | L2 | L2 | L2 | |
| fHbp family | B | B | B | B | B | B | B | A | A | B | A | B | B | A | |
| fHbp expression | ++ | ?? | + | + | +/− | ?? | +/− | + | + | +/− | − | − | − | ?? | |
| | | | | | | | SBA with TPEN | | | | | | | | |
| anti-TdfI blebs sera | 599 | 1460 | 1367 | 1449 | 656 | 2049 | 585 | 1650 | 1577 | 1200 | 50 | 504 | 60 | 1215 | |
| anti-fHbp sera | 3539 | 5786 | 388 | 509 | 169 | 2104 | 4373 | 50 | 50 | 50 | 50 | 50 | 50 | 50 | |
| mix of both sera | 5941 | 7264 | 1284 | 1690 | 1127 | 4782 | 8305 | 2741 | 2540 | 308 | 50 | 505 | 50 | 1292 | |
| | | | | | | | SBA without TPEN | | | | | | | | |
| anti-TdfI blebs sera | 220 | 160 | 50 | 50 | 50 | 50 | 161 | 50 | 50 | 50 | 50 | 50 | 118 | 50 | |
| anti-fHbp sera | 3383 | 3993 | 110 | 494 | 50 | 2293 | 3804 | 50 | 50 | 50 | 50 | 50 | 50 | 50 | |
| mix of both sera | 3104 | 5144 | 50 | 486 | 50 | 3645 | 5432 | 50 | 50 | 50 | 50 | 50 | 50 | 50 | |

Example 12

Protective effects of different vaccine compositions in SBA against 19 *N. meningitidis* strains using baby rabbit serum as complement source. Results are expressed as the percentage of strains killed (titers ≥1/128). Comparison of strain coverage induced by the bivalent 15% LOS OMV vaccine, the bivalent fHBP and the pentavalent subunit vaccine comprising-fHbp (GNA1870) NadA, GNA2132 (Lipo28), GNA1030, GNA2091.

TABLE 6

|  |  |  | Number (%) of strains killed (SBA ≥ $1/128$) | | |
|---|---|---|---|---|---|
| LOS type | $N^a$ | Serogroup$^b$ | Bivalent OMVs | Bivalent fHBP | Pentavalent vaccine |
| L2 | 6 | B, W | 4 (67%) | 0 | 1 (17%) |
| L3, 7 | 4 | B | 3 (75%) | 4 (100%) | 3 (75%) |
| L3v | 6 | B, C, W, Y | 6 (100%) | 2 (33%) | 6 (100%) |
| L4 | 1 | C | 0 | 1 (100%) | 0 |
| L10 | 1 | A | 0 | 0 | 0 |
| L11 | 1 | A | 1 (100%) | 0 | 1 (100%) |
| All | 19 |  | 14 (74%) | 7 (37%) | 11 (58%) |

$^a$Number of strains tested expressing the respective LOS type
$^b$Serogroup represented by the strains tested in SBA for respective LOS type Same results but presented in more detail:

TABLE 7

|  | L3 | | | | L3V | | | L3V and L3 or L4 | | |
|---|---|---|---|---|---|---|---|---|---|---|
|  | B | B | B | B | B | W | Y | B | B | C |
|  | H44/76 | M687 | NZ124 | S3446 | 6275 | 3193 | S1975 | 2991 | 608B | C11 |
| fHbp expression (WB) | ++ | ++ | + | + | − | NT | NT | + | − | NT |
| L7 + L2 non-ads | 3232 | 1611 | 132 | 54 | 7122 | 12734 | 25600 | 1023 | 25600 | 1023 |
| L7 + L2 ads | 1164 | 747 | 158 | 10 | 3327 | 13054 | 9840 | 25600 | 6326 | 566 |
| TiL3 + TiL2 non-ads | 40950 | 2542 | 504 | 112 | 5935 | 18153 | 25600 | 25600 | 9371 | 1105 |
| TiL3 + TiL2 ads | 2705 | 1517 | 343 | 61 | 747 | 4879 | 9728 | 25600 | 3460 | 463 |
| Protein956 | 15 | 11 | 10 | 10 | 10 | 10 | 545 | 10 | 10 | 50 |
| Protein956 | 15 | 10 | 10 | 10 | 10 | 10 | 567 | 10 | 10 | 50 |
| GNA2132 | 15 | 10 | 57 | 102 | 10 | 10 | 477 | 113 | 10 | 50 |
| GNA1870 | 1942 | 416 | 33 | 10 | 10 | 10 | 10 | 55 | 10 | 50 |
| NadA | 13 | 50 | 10 | 10 | 118 | 5144 | 7455 | >20480 | 906 | 840 |
| 5CVMB | 3759 | 3737 | 104 | 319 | 901 | 4607 | 12780 | >20480 | 635 | 506 |
| fHbpB | 5653 | 11354 | 604 | 36 | <50 | <50 | <50 | <50 | <50 | <50 |
| fHbpA | 125 | 120 | 232 | 396 | <50 | <50 | <50 | 158 | <50 | <50 |
| fHpA + B | 8991 | 5119 | 741 | 1104 | <50 | <50 | 123 | 1466 | <50 | 159 |
| GNA1870 Western Blot | ++ | ++ | + | + | − | NT | NT | + | − | NT |

|  | L4? | L2 | | | | | | L10 | L11 |
|---|---|---|---|---|---|---|---|---|---|
|  | C | B | B | B | B | B | W | A | A |
|  | C19 | 760676 | B16B6 | 2986 | 3356 | BZ232 | S4383 | 3125 | F8238 |
| fHbp expression (WB) | NT | − | − | − | − | − | NT | NT | NT |
| L7 + L2 non-ads | 10 | 3060 | 1148 | 7328 | 22 | 10 | 1041 | 10 | 4240 |
| L7 + L2 ads | 10 | 1192 | 715 | 4542 | 87 | 10 | 935 | 10 | 3221 |
| TiL3 + TiL2 non-ads | 10 | 2450 | 415 | 3929 | 34 | 10 | 2164 | 22 | 4348 |
| TiL3 + TiL2 ads | 10 | 406 | 281 | 2068 | 73 | 10 | 369 | 10 | 4073 |
| Protein956 | 10 | 10 | 10 | 10 | 10 | 10 | 23 | 10 | 10 |
| Protein956 | 10 | 10 | 10 | 10 | 10 | 10 | 10 | 10 | 10 |
| GNA2132 | 266 | 10 | 10 | 10 | 29 | 10 | 10 | 10 | 10 |
| GNA1870 | 10 | 10 | 10 | 10 | 10 | 10 | 23 | 10 | 10 |
| NadA | 10 | 13 | 251 | 997 | 10 | 10 | 10 | 10 | 3137 |
| 5CVMB | 53 | 11 | 108 | 1013 | 59 | 10 | 10 | 10 | 4286 |
| fHbpB | <10 | <50 | <50 | <50 | <10 | <10 | <50 | <10 | <50 |
| fHbpA | 64 | <50 | <50 | <50 | <10 | <10 | <50 | <10 | <50 |
| fHpA + B | 513 | <50 | <50 | <50 | <10 | 101 | <50 | <10 | <50 |
| GNA1870 Western Blot | NT | − | − | − | − | − | NT | NT | NT |

Example 13

Immunogenicity of chimeric fHbp proteins

Methods
Antigen Preparations
Chimeric fHbp proteins with/without mutation of fH binding site were prepared as described in the above examples (Examples 1-7).

Animal Procedures:
Groups of 20 mice were immunized three times by the intramuscular (IM) route on day 0, 21 and 35. Each injection contained 5 µg of chimeric fHbp proteins adsorbed onto $Al(OH)_3$. On day 49, blood samples were taken for serum. Mice sera were from experiment 20090833.

rSBA
N. meningitidis strains were cultivated overnight on Petri Dishes at 37° C.+5% $CO_2$. They were sub-cultured for 4 hours on Petri Dishes at 37° C.+5% $CO_2$. Serum samples (individual sera) were inactivated for 40 min at 56° C. and then diluted 1/50 in PBS-glucose 0.1% and then twofold diluted (8×) in a volume of 25 µl in flat bottom microplates. Then 25 µl of a mix of bacteria, from agar-plate culture (diluted in PBS-glucose 0.1% to yield ~50-250 CFU per well) and baby rabbit complement (final concentration in microwell: 12.5% v/v) was added to the serum dilution. After 75 min of incubation at 37° C. under shaking, 2 layers of agar (0.9%) were added to the wells. The microplates were incubated overnight at 33° C.+$CO_2$. The CFU's were counted and the percentage of killing was calculated. The SBA titer is the dilution giving 50% of killing.

Individual sera were analysed and geometric mean titer was calculated. For geometric mean calculation, titer was set at 50 when killing for first dilution was below 50% killing or titer was set at 25600 if killing was higher than 50% at last dilution.

Results
Sera were tested in rSBA with strain expressing the fHbp family B (H44/76) or the fHbp family A (S3446) (table 1 below).

Immunisation with recombinant fHbpB induced the production of bactericidal antibodies able to mediate the complement killing of H44/76 strain (fHbp family B) but not S3446 strain (fHbp family A) (percentage of responders 100% and 10%, respectively). The recombinant fHbpA induced a low bactericidal antibody response agaitst the S3446 strain and a very low response against the H44/76 strain.

Animals immunized with a chimeric fHbp (with or without fH binding site mutation) were able to elicit a bactericidal response against both H44/76 and S3446 strains (up to 100% and 90% responders against H44/76 and S3446 respectively). The best response was achieved with the construction LVL-511 (two amino acid mutations).

TABLE 1 bactericidal titer of anti-chimeric fHbp antibodies in presence of baby rabbit complement

|  |  | Chimaeric fHbp LVL-491 | Chimaeric fHbp fH binding mutation A LVL-511 | Chimaeric fHbp fH binding mutation B LVL-512 | Chimaeric fHbp fH binding mutation C LVL-513 | Chimaeric fHbp fH binding mutation E LVL-514 | Wild type fhbp A LVL-489 | Wild type fhbp B LVL-490 | ctrl (—) |
|---|---|---|---|---|---|---|---|---|---|
| H44/76 (fHbp family B) | GMT (50% killing) | 846 | 2291 | 1017 | 762 | 1187 | 60 | 10121 | 58 |
|  | Responders (titer ≥100) | 95% | 100% | 100%* | 100%* | 100%* | 25%* | 100%* | 18%* |
| S3446 (fHbp family A) | GMT (50% killing) | 301 | 466 | 190 | 114 | 112 | 93 | 60 | 50 |
|  | Responders (titer ≥100) | 85% | 90% | 85% | 55% | 45% | 45% | 10% | 0% |

*n = 6 to 19 due to invalid results (low CFU)

Conclusion
Anti-chimeric fHbp antibodies were able to provide effective killing of strains from both fHbp family (A and B). This ability is not altered by mutation of the fH binding site.

Example 14

Immunogenicity of Hap (also called Map herein)

Methods
Antigen Preparations
Map
Native cleaved Map was purified from supernatant obtained after fermentation of H44/76 cps-strain. Two lots were produced, the second lot being obtained from H44/76 cps-overexpressing Map [achieved by amplifying the entire map gene from H44/76 by PCR and cloning in a Neisserial replicative plasmid derived from pFP10 (Pagotto et al, Plasmid 43, 24-34, 2000), containing a lacI$^Q$ gene and a tandem lac/tac promoter for controlled expression of Map]. Map was purified by concentration and chromatography steps.

Recombinant Map N-ter (aa 43-1178) was produced by cytoplasmic expression in E. coli.

fHbp
Recombinant fHbps variants (v) A and B were produced in BL21 (DE3) E. coli after IPTG induction and purification using IMAC column. The fHbp sequences were derived from strains MC58 (fHbp B) and 2996 (fHbp A). Genes were cloned in pET24b plasmid without the nucleotide sequence corresponding to the leader sequence and with a His-Tag in C-ter.

Animal Procedures
Map
Groups of 10-25 mice were immunized three times by the intramuscular (IM) route on day 0, 14 and 28. Each injection contained 10 µg of native cleaved Hap or 5 µg of rec N-ter Hap formulated with specol. On day 42, blood samples were taken for serum. Mice sera were from experiments 20090608, 20100463, 20100708.

Groups of 6-10 guinea-pigs were immunised three times by the intramuscular (IM) route on day 0, 14 and 28. Each injection contained 10 μg of protein formulated with specol. On day 42, blood samples were taken for serum. Guinea pig sera were from experiments 20090619, 20100464, 20100711.

fHbp

Groups of 10-30 mice were immunized three times by the intramuscular (IM) route on day 0, 21 and 28. Each injection contained 5 μg of monovalent fHbp vaccine (fHbp A or fHbp B) adsorbed onto $Al(OH)_3$. On day 42, blood samples were taken for serum. Mice sera were from experiments 20080790 and 20090265.

Groups of 6-10 guinea pigs were immunized three times by the intramuscular (IM) route on day 0, 14 and 28. Each injection contained 10 μg of monovalent fHbp vaccine (fHbp A or fHbp B) adsorbed onto $Al(OH)_3$. On day 42, blood samples were taken for serum. Sera were from experiments 20090200g3 or 20100464g10.

SBA

N. meningitidis strains were cultivated overnight on Petri Dishes at 37° C.+5% $CO_2$. They were sub-cultured for 4 hours on Petri Dishes with 20 μM TPEN (zinc chelator) at 37° C.+5% $CO_2$. Serum samples (pooled sera) were inactivated for 40 min at 56° C. and then diluted 1/50 in PBS-glucose 0.1% and then twofold diluted in a volume of 25 μl in flat bottom microplates. Then 25 μl of a mix of bacteria, from agar-plate culture or after cell contact (diluted in PBS-glucose 0.1% to yield ~50-250 CFU per well) and baby rabbit complement (final concentration in microwell: 12.5% v/v) was added to the serum dilution. After 75 min of incubation at 37° C. under shaking, 2 layers of agar (0.9%) were added to the wells. The microplates were incubated overnight at 33° C.+$CO_2$. The CFU's were counted and the percentage of killing was calculated. The SBA titer is the dilution giving 50% of killing.

Map KO Strain Construction

N. meningitidis strains growth and transformation procedure were performed as described previously (Weynants et al, 2009).

Strain 17540 was a gift from Julio Vasquez (CNM, Madrid, Spain), strain M01-240355 and NZ98/254 from R. Borrow (HPA, Manchester, UK).

The map/hap:: kanR plasmid, consisting in a kanamycine resistance cassette inserted into the unique PstI site of the H44/76 hap gene (van Ulsen et al, 2003) was a kind gift of Prof. Tommassen. Kanamycin-resistant colonies were screened for the inactivation of the hap gene by PCR on boiled bacterial lysate. Integrity of LOS was checked by Tricine gel and Silver staining for all clones to avoid changes in complement sensitivity.

Genetically modified L3,7 and L2 lipooligosaccharides from Neisseria meningitidis serogroup B confer a broad cross-bactericidal response. Weynants V, Denoël P, Devos N, Janssens D, Feron C, Goraj K, Momin P, Monnom D, Tans C, Vandercammen A, Wauters F, Poolman J T. Infect Immun. 2009 May; 77(5):2084-93.

A Neisserial autotransporter NaIP modulating the processing of other autotransporters. van Ulsen P, van Alphen L, ten Hove J, Fransen F, van der Ley P, Tommassen J. Mol. Microbiol. 2003 November; 50(3)

Results

Different *N. meningitidis* strains selected based on their homology for Map were tested in SBA using sera from mice and guinea pigs immunized with native cleaved Map or recombinant N-ter Map formulated with specol. As shown by the results (table 1 below), Map induces a cross protective bactericidal response as strain M06-240336 with the lowest homology with H44/76 is killed. 17/22 strains are killed with anti-native cleaved Map antibodies obtained from guinea pigs. Six of these 17 strains are not killed by anti-fHbp antibodies. Difference of expression level of Map could be an explanation for absence of killing some strains as suggested by the facts that strains sharing similar Map sequences are killed (M06-240336) or not killed (M06-240877).

To confirm that Map is the target of bactericidal antibodies, ΔMap strains (NZ98/254, M05-240355, SP17540) were used in bactericidal assays (table 2 below). In such SBA conditions, no killing was observed. These results confirm Map as a major antigen to induce cross bactericidal antibodies.

TABLE 1 bactericidal titer of anti-Map antibodies in presence of baby rabbit complement

| | | | H44/76 | MC58 | M97-250687 | SP17540 | M05-0240072 | M01-240355 | 760676 | BZ10 | SP17662 | M01-240101 | M05-240210 | NZ98/254 |
|---|---|---|---|---|---|---|---|---|---|---|---|---|---|---|
| | Map homology (H44/76 = 100%) | | 100% | 99.9% | 99.9% | 98.8% | 98.7% | 98.7% | 98.7% | 98.4% | 97% | 96.9% | 96.1% | 96% |
| | fHbp family | | B | B | B | B | B | A | A | A | A | B | B | B |
| | fHbp expression | | ++ | ++ | ++ | − | − | + | − | | + | + | + | + |
| | Immunotype | | L3 | L3 | L3 | L2 | L2 | L3 | L2 | L3 | L3 | L3 | L2 | L3 |
| | cc | | ST32 | ST32 | ST32 | ST11 | ST11 | CC213 | ST11 | ST8 | ST269 | ST269 | | ST41/4 |
| Animal | Treatment | | Serum bactericidal titers | | | | | | | | | | | |
| | fHbp B sera or A | | 3539 | 5786 | | <100 | <100 | <100 | <100 | 775 | 256 | 509 | <100 | 333 |
| mouse | native | lot 1 | 137 | | 2394 | 113 | <100 | 769 | <100 | 1578 | 896 | 2742 | <100 | 570 |
| | cleaved Map | lot 2 | 580 | 536 | 5036 | 510 | <100 | 744 | | 2443 | 1936 | | <100 | 1684 |
| | rec N-ter Map | | 471 | | | 1149 | | 2337 | | 1431 | | | | 157 |
| GP | native | lot 1 | 781 | 938 | 4658 | 1098 | <100 | 2679 | 116 | 6162 | 2353 | 4871 | <100 | 1617 |
| | cleaved Map | lot 2 | 4070 | 4762 | 12047 | 5658 | 143 | 6800 | | >12800 | 11884 | | <100 | 6688 |
| | rec N-ter | | 8286 | | | 2123 | | 10055 | | 8991 | | | | 5278 |

TABLE 1-continued bactericidal titer of anti-Map antibodies in presence of baby rabbit complement

| | Map | | M05-0240471 | M06-240877 | M06-241336 | DE 10038 | M01-240013 | M01-240149 | SP18025 | DE 10690-06 | M98-250771 | SP17567 |
|---|---|---|---|---|---|---|---|---|---|---|---|---|
| | Map homology (H44/76 = 100%) | | 96% | 90.6% | 90.6% | 90.6% | | | | | | |
| | fHbp family | | B | | | B | A | B | B | B | A | |
| | fHbp expression | | +/− | | | + | + | + | +/− | +/− | +/− | |
| | Immunotype | | L3 | | | | L3 | L3 | | | | L3 |
| | cc | | 4 | | | | ST269 | ST41/44 | | | | |
| Animal | Treatment | | | | | Serum bactericidal titers | | | | | | |
| mouse | fHbp B sera or A | | <100 | | 367 | | <100 | 2104 | 4373 | <100 | <100 | 110 |
| | native cleaved Map | lot 1 | <100 | <100 | 2327 | <100 | | | | | | |
| | | lot 2 | <100 | | | | <100 | <100 | 1217 | <100 | <100 | <100 |
| | rec N-ter Map | | | | | | 1365 | 920 | | | | |
| GP | native cleaved Map | lot 1 | <100 | <100 | 8561 | <100 | 7819 | 6300 | 1605 | <100 | 1527 | 121 |
| | | lot 2 | <100 | | | | >12800 | >12800 | 4263 | <100 | 6258 | 587 |
| | rec N-ter Map | | | | | | 7254 | 4448 | | | | |

TABLE 2 bactericidal titer of anti-Map antibodies against Map KO strains

| | | | NZ98/254 (fHBP B/+) strains | | M05-240355 (fHBP A/+) strains | | SP17540 (fHBP B/−) strains | |
|---|---|---|---|---|---|---|---|---|
| Species | Treatment | | WT | ΔMap | WT | ΔMap | WT | ΔMap |
| mouse | native cleaved Map | lot 2 | 1684 | <100 | 744 | <100 | 510 | <100 |
| | rec cytoplasmic Map | | NT | NT | NT | NT | 1149 | <100 |
| GP | native cleaved Map | lot 1 | 1617 | <100 | 2679 | <100 | 1098 | <100 |
| | | lot 2 | 6688 | <100 | 6800 | <100 | 5658 | <100 |
| | rec cytoplasmic Map | lot 2 | NT | NT | NT | NT | 2123 | <100 |

Conclusion

Map induces cross-bactericidal activity and provide effective killing of strains not killed by anti-fHbp including strains from clonal complex ST269 (eg M01-240013 strain) and strains from L2 immunotype (eg SP17540 strain).

The results suggest that a vaccine based on Map and fHbp will offer a better strain coverage than a vaccine based on fHbp.

Example 15

Hsf (also called Msf herein) induces bactericidal antibodies against wild type strains Methods Antigen Preparations OMVs Outer membranes vesicles (OMVs) were produced using classical 0.5% DOC extraction from recombinant H44/76 strain (porA KO, capsule minus, galE LOS and over-producing Msf and/or ZnuD protein).

fHbp

Recombinant fHbps variants (v) A and B were produced in BL21 (DE3) *E. coli* after IPTG induction and purification using IMAC column. The fHbp sequences were derived from strains MC58 (fHbp B) and 2996 (fHbp A). Genes were cloned in pET24b plasmid without the nucleotide sequence corresponding to the leader sequence and with a His-Tag in C-ter.

mAb mAb Hsfcross/5 was obtained from fusion of myeloma cells and lymphocyte B obtained from BALB/c mice immunized with 20 μg of OMVs from recombinant H44/76 strain (porA KO, capsule minus over-producing Msf from strain M01-0240101) using a repetitive, multiple site immunization strategy designated RIMMS.

Animal Procedures:

OMVs

Groups of 10 guinea-pigs (GP) were immunized three times by the intramuscular (IM) route on day 0, 14 and 28. Each injection contained OMV antigen normalized to 10 μg of protein and formulated with $AlPO_4$. On day 42, blood samples were taken for serum. Sera were from experiments 20090266.

fHbp

Groups of 6-10 guinea pigs were immunized three times by the intramuscular (IM) route on day 0, 14 and 28. Each injection contained 10 μg of monovalent fHbp vaccine (fHbp A or fHbp B) adsorbed onto $Al(OH)_3$. On day 42, blood samples were taken for serum. Sera were from experiments 20090200g3 or 20100464g10.

SBA

*N. meningitidis* strains were cultivated overnight on Petri Dishes at 37° C.+5% $CO_2$.

They were sub-cultured for 4 hours on Petri Dishes at 37° C.+5% $CO_2$. Serum samples (pooled sera) were inactivated for 40 min at 56° C. and then diluted 1/50 in PBS-glucose 0.1% and then twofold diluted in a volume of 25 μl in flat bottom microplates. Then 25 μl of a mix of bacteria, from agar-plate culture (diluted in PBS-glucose 0.1% to yield ~50-250 CFU per well) and baby rabbit complement (final concentration in microwell: 12.5% v/v) was added to the serum dilution. After 75 min of incubation at 37° C. under shaking, 2 layers of agar (0.9%) were added to the wells. The microplates were incubated overnight at 33° C.+$CO_2$. The CFU's were counted and the percentage of killing was calculated. The SBA titer is the dilution giving 50% of killing.

Msf/Hsf KO Strain Construction

*N. meningitidis* B strain 17567 (from J. Vasquez, CNM, Madrid, Spain) growth and transformation procedure were performed as described previously (Weynants et al, 2009). The msf/hsf::CmR plasmid was constructed as followed. Briefly, a DNA fragment of 4771 bp corresponding to the 1531 bp 5' flanking region of hsf gene, the 1775 bp of hsf coding sequence and the 1465 bp 3' flanking region was PCR amplified from H44/76 genomic DNA with primers Hsf sens (CGCAATAAATGGGGTTGTCAATAATTGT) and Hsf reverse (AGTCAAGGCGCACGCTGTCGGCAT) and cloned in pGEMT-Easy vector. The plasmid was then submitted to circle PCR mutagenesis with primers HSF5'ci2 (gaagatctgccgtctgaaacccgtaccgatgcggaaggctata) and HSF3'ci2 (gaagatctttcagacggcgataaagtcctgccgcgttgtgtttc) in order to (i) delete hsf gene, (ii) insert uptake sequences and (iii) insert BglII restriction sites allowing easy cloning of the antibiotic resistance gene. The CmR gene was amplified from pCMC plasmid (Weynants et al, 2009) using primers $BAD_2O$ (tcccccgggagatctcactagtattaccctgttatccc) and CAM3'Bgl2 (agatctgccgctaactataacggtcc) primers. This fragment was cloned into the circle PCR product after BglII restriction resulting in plasmid pRIT15456. Chloramphenicol-resistant colonies were screened for the inactivation of the msf/hsf gene by PCR on boiled bacterial lysate. Absence of Msf expression was further confirmed by Western Blot. Integrity of LOS was also checked by Tricine gel and Silver staining for all clones to avoid changes in complement sensitivity.

Genetically modified L3,7 and L2 lipooligosaccharides from *Neisseria meningitidis* serogroup B confer a broad cross-bactericidal response.

Weynants V, Denoel P, Devos N, Janssens D, Feron C, Goraj K, Momin P, Monnom D, Tans C, Vandercammen A, Wauters F, Poolman J T. Infect Immun. 2009 May; 77(5):2084-93.

Results

To evaluate the potential of Msf to induce bactericidal antibodies against wild type strains, strain SP17567 with a high level of Msf expression (western blotting results) was selected.

Sera against Msf or Msf-ZnuD OMVs and control blebs (without antigen overexpression or only ZnuD overexpression) were tested in serum bactericidal assay. Monoclonal antibody specific for Msf was also tested.

Results in table 1 below show an increase of at least 20 fold of bactericidal activity for Msf overexpressing blebs compared to control blebs. High bactericidal titer is also observed with Msf specific mAb. Only the recombinant fHbpA induces a low bactericidal response around the detection limit of the test.

To confirm that Msf is the major target of bactericidal antibodies, ΔMsf SP17567 strains was used in bactericidal assay. In such SBA conditions, no killing was observed. These results confirm Msf as antigen is able to induce killing of wild type strain expressing high level of Msf.

TABLE 1 bactericidal titer against strains SP17567 wild type and Msf KO

| | | SP17567 | |
|---|---|---|---|
| | | WT | ΔMsf |
| mAb Msf | | 2864 | <100 |
| OMVs | Ctrl OMVs | 390 | <100 |
| | ZnuD OMVs | <100 | <100 |
| | Msf OMVs | 7821 | <100 |
| | ZnuD-Msf OMVs | 5847 | <100 |
| fHbpA | | 110 | <100 |
| fHbpB | | <100 | <100 |
| mAb LOS (L7/12) | | 896 | 522 |

Conclusion

Anti-Msf antibodies could mediate the killing of a wild type strain that is poorly killed by anti-fHbp antibodies. This suggests that the addition of Msf to a fHbp based vaccine could enhance the coverage of a MenB vaccine.

Example 16

Effect of antibodies against Tdfl (also called ZnuD herein) overexpressing blebs on L2 strains Methods Antigen Preparations Outer membranes vesicles (OMVs) were produced using classical 0.5% DOC extraction from recombinant H44/76 strain (porA KO, capsule minus, galE LOS and over-producing ZnuD (and Msf) protein).

Animal Procedures:

OMVs

Groups of 26-30 mice were immunized three times by the intramuscular (IM) route on day 0, 21 and 28.

Groups of 10 guinea-pigs (GP) were immunized three times by the intramuscular (IM) route on day 0, 14 and 28.

Each injection contained OMV antigen normalized to 5 (mice) or 10 μg (GP) of protein and formulated with $AlPO_4$. On day 42, blood samples were taken for serum. Mice and guinea pig sera were from experiments 20090265, 20100463 and 20090266, 20100464 respectively.

fHbp

Groups of 20 mice were immunized three times by the intramuscular (IM) route on day 0, 21 and 35. Each injection contained 5 μg of monovalent fHbp vaccine (fHbp A or fHbp B) adsorbed onto $Al(OH)_3$. On day 49, blood samples were taken for serum. Mice sera were from experiment 20090833.

SBA

*N. meningitidis* strains were cultivated overnight on Petri Dishes at 37° C.+5% $CO_2$. They were sub-cultured for 4 hours on Petri Dishes without or with 20 μM TPEN (zinc chelator) 37° C.+5% $CO_2$. Serum samples (pooled sera) were inactivated for 40 min at 56° C. and then diluted 1/50 in PBS-glucose 0.1% and then twofold diluted in a volume of 25 μl in flat bottom microplates. Then 25 μl of a mix of bacteria, from agar-plate culture (diluted in PBS-glucose 0.1% to yield ~50-250 CFU per well) and baby rabbit complement (final concentration in microwell: 12.5% v/v) was added to the serum dilution. After 75 min of incubation at 37° C. under shaking, 2 layers of agar (0.9%) were added to the wells. The microplates were incubated overnight at 33° C.+$CO_2$. The CFU's were counted and the percentage of killing was calculated. The SBA titer is the dilution giving 50% of killing.

ZnuD KO SP17540 Strain Construction

*N. meningitidis* strains growth and transformation procedure were performed as described previously (Weynants et al, 2009). When needed, induction of ZnuD expression was obtained by adding 20 mM TPEN (N,N,N',N'-tetrakis(2-pyridylmethyl)ethylenediamine) in the medium. Strain 17540 was a gift from Julio Vasquez (CNM, Madrid, Spain).

The znuD kanR plasmid was a kind gift of Prof. Tommassen and is described in Stork et al, 2010. Kanamycin- The evaluation of the bactericidal potential of ZnuD antibodies was performed via the use of zinc-restricted growth media (like in-vivo conditions). This was achieved by using 20 μM of TPEN in MH agar plates.

Mouse anti-ZnuD OMVs sera tested in a bactericidal assay under TPEN conditions demonstrated the killing of the three strains tested. Similar results were observed with sera from guinea-pigs. In the absence of TPEN in the culture medium, strains were not killed by anti-ZnuD antibodies.

To confirm that ZnuD is a major target of bactericidal antibodies, a ΔZnuD SP17540 strain was used in bactericidal assays with TPEN. In such SBA condition, no killing was observed. These results demonstrate that ZnuD is the major target of bactericidal antibodies against strain SP17540.

TABLE 1 bactericidal titer of anti-OMVs against L2 strains

| | | | M05-0240072 | 760676 | SP17540 | SP17540 ZnuD KO |
|---|---|---|---|---|---|---|
| | fHbp family | | B | A | B | |
| | fHbp expression | | — | — | — | |
| | Immunotype (inner-core typing) | | L2 | L2 | L2 | |
| | Clonal complex | | ST11 | ST11 | ST11 | |
| Animal | Treatment | | Serum bactericidal titers | | | |
| | fHbp B sera or A | | <100 | <100 | <100 | <100 |
| mouse | Ctrl OMVs | MH-agar | <100 | | | |
| | | MH + TPEN agar | <100 | | | |
| | ZnuD OMVs | MH-agar | | <100 | | |
| | | MH + TPEN agar | 3400 | 1308 | 2130 | <100 |
| | ZnuD-Msf OMVs (B2468) (lot1) | MH-agar | <100 | | | |
| | | MH + TPEN agar | 6590 | 3182 | 3433 | <100 |
| | ZnuD-Msf OMVs (B2468) (lot2) | MH-agar | <100 | | | |
| | | MH + TPEN agar | 2943 | | | |
| GP | Ctrl OMVs | MH-agar | <100 | | | |
| | | MH + TPEN agar | <100 | | | |
| | ZnuD OMVs | MH-agar | | <100 | | |
| | | MH + TPEN agar | 5311 | 6315 | 8877 | <100 |
| | ZnuD-Msf OMVs (B2468) (lot1) | MH-agar | <100 | | | |
| | | MH + TPEN agar | 3631 | 2312 | 9344 | <100 |
| | ZnuD-Msf OMVs (B2468) (lot2) | MH-agar | <100 | | | |
| | | MH + TPEN agar | 4871 | | | | resistant colonies were screened for the partial deletion of the znuD gene by PCR on boiled bacterial lysate. ZnuD inactivation was further confirmed by Western blot on whole cell lysate after growth in presence of TPEN. Integrity of LOS was checked by Tricine gel and Silver staining for all clones to avoid changes in complement susceptibility.

Genetically modified L3,7 and L2 lipooligosaccharides from *Neisseria meningitidis* serogroup B confer a broad cross-bactericidal response. Weynants V, Denoel P, Devos N, Janssens D, Feron C, Goraj K, Momin P, Monnom D, Tans C, Vandercammen A, Wauters F, Poolman J T. Infect Immun. 2009 May; 77(5):2084-93.

An outer membrane receptor of *Neisseria meningitidis* involved in zinc acquisition with vaccine potential. Stork M, Bos M P, Jongerius I, de Kok N, Schilders I, Weynants V E, Poolman J T, Tommassen J. PLoS Pathog. 2010 Jul. 1; 6:e1000969.

Results

Three strains from L2 immunotype and clonal complex ST11 were used in rSBA. These strains are not killed by anti-fHbp antibodies and complement (table 1).

Discussion and Conclusion

It is to note that in previous experiment (see example 11 above), two L2 strains (760676 and M05-0240072) strains were not killed by anti-ZnuD antibodies. In repeated experiments (presented in this example), these two strains are killed by anti-ZnuD antibodies. Because the expression of ZnuD was not systematically checked on cultures done to perform SBA, it is thought that ZnuD was not expressed by the strains 760676 and M05-0240072 in the former series of experiments (presented in example 11). One possible explanation for absence of expression was the use of too old TPEN plates for an efficient chelation of zinc.

The new results, obtained with WT L2 strains as well as the SP17540 znuD KO strain, confirm that ZnuD (over-expressed in OMVs) provides effective killing of strains from L2 immunotype not killed by anti-fHbp. The data support the idea that a vaccine based on fHbp and additional antigen(s), like ZnuD, will improve the strain coverage compared to a vaccine based on fHbp only.

The invention claimed is:

1. A method of inducing an effective immunogenic response in an individual against a Neisserial infection comprising the step of administering to an individual a protective dose of an immunogenic composition comprising a combination of:

(a) a first, fHbp, polypeptide antigen that elicits anti-fHbp antibodies in the individual and (b) a second Tdfl polypeptide antigen that elicits anti-Tdfl antibodies in the individual against *Neisseria meningitidis* ST269, wherein said immunogenic composition does not induce an immune response to FrpB.

2. The method of claim 1, wherein the second antigen composition comprises an additional antigen other than Tdfl.

3. The method of claim 1, wherein the second antigen composition further comprises TdfH.

4. The method of claim 1, wherein the fHbp antigen is selected from the group consisting of: fhBP A and fhBP B.

* * * * *

SEQUENCE LISTING

<160> NUMBER OF SEQ ID NOS: 27

<210> SEQ ID NO 1
<211> LENGTH: 136
<212> TYPE: PRT
<213> ORGANISM: Neisseria meningitidis

<400> SEQUENCE: 1

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Lys Val Ser Arg Phe Asp Phe Ile Arg Gln
65                  70                  75                  80

Ile Glu Val Asp Gly Gln Leu Ile Thr Leu Glu Ser Gly Glu Phe Gln
                85                  90                  95

Val Tyr Lys Gln Ser His Ser Ala Leu Thr Ala Phe Gln Thr Glu Gln
            100                 105                 110

Ile Gln Asp Ser Glu His Ser Gly Lys Met Val Ala Lys Arg Gln Phe
        115                 120                 125

Arg Ile Gly Asp Ile Ala Gly Glu
    130                 135

<210> SEQ ID NO 2
<211> LENGTH: 119
<212> TYPE: PRT
<213> ORGANISM: Neisseria meningitidis

<400> SEQUENCE: 2

Gly Glu His Thr Ala Phe Asn Gln Leu Pro Asp Gly Lys Ala Glu Tyr
1               5                   10                  15

His Gly Lys Ala Phe Ser Ser Asp Asp Ala Gly Gly Lys Leu Thr Tyr
            20                  25                  30

Thr Ile Asp Phe Ala Ala Lys Gln Gly His Gly Lys Ile Glu His Leu
        35                  40                  45

Lys Thr Pro Glu Gln Asn Val Glu Leu Ala Ala Ala Glu Leu Lys Ala
    50                  55                  60

Asp Glu Lys Ser His Ala Val Ile Leu Gly Asp Thr Arg Tyr Gly Ser
65                  70                  75                  80

Glu Glu Lys Gly Thr Tyr His Leu Ala Leu Phe Gly Asp Arg Ala Gln
                85                  90                  95

Glu Ile Ala Gly Ser Ala Thr Val Lys Ile Gly Glu Lys Val His Glu
            100                 105                 110

Ile Gly Ile Ala Gly Lys Gln
        115

<210> SEQ ID NO 3
<211> LENGTH: 23
<212> TYPE: PRT
<213> ORGANISM: Neisseria meningitidis
<220> FEATURE:
<221> NAME/KEY: VARIANT
<222> LOCATION: (8)..(8)
<223> OTHER INFORMATION: "X" is I/T
<220> FEATURE:

<221> NAME/KEY: VARIANT
<222> LOCATION: (14)..(14)
<223> OTHER INFORMATION: "X" is Q/R

<400> SEQUENCE: 3

Lys Ile Asn Asn Pro Asp Lys Xaa Asp Ser Leu Ile Asn Xaa Arg Ser
1               5                   10                  15

Phe Leu Val Ser Gly Leu Gly
            20

<210> SEQ ID NO 4
<211> LENGTH: 23
<212> TYPE: PRT
<213> ORGANISM: Neisseria meningitidis
<220> FEATURE:
<221> NAME/KEY: VARIANT
<222> LOCATION: (2)..(2)
<223> OTHER INFORMATION: "X" is V/I/E
<220> FEATURE:
<221> NAME/KEY: VARIANT
<222> LOCATION: (5)..(5)
<223> OTHER INFORMATION: "X" is S/P
<220> FEATURE:
<221> NAME/KEY: VARIANT
<222> LOCATION: (7)..(7)
<223> OTHER INFORMATION: "X" is D/H
<220> FEATURE:
<221> NAME/KEY: VARIANT
<222> LOCATION: (9)..(9)
<223> OTHER INFORMATION: "X" is G/R
<220> FEATURE:
<221> NAME/KEY: VARIANT
<222> LOCATION: (10)..(10)
<223> OTHER INFORMATION: "X" is K/S
<220> FEATURE:
<221> NAME/KEY: VARIANT
<222> LOCATION: (16)..(16)
<223> OTHER INFORMATION: "X" is Q/R
<220> FEATURE:
<221> NAME/KEY: VARIANT
<222> LOCATION: (18)..(18)
<223> OTHER INFORMATION: "X" is R/K
<220> FEATURE:
<221> NAME/KEY: VARIANT
<222> LOCATION: (23)..(23)
<223> OTHER INFORMATION: "X" is A/V

<400> SEQUENCE: 4

Gln Xaa Gln Asp Xaa Glu Xaa Ser Xaa Xaa Met Val Ala Lys Arg Xaa
1               5                   10                  15

Phe Xaa Ile Gly Asp Ile Xaa
            20

<210> SEQ ID NO 5
<211> LENGTH: 255
<212> TYPE: PRT
<213> ORGANISM: Neisseria meningitidis strain MC58

<400> SEQUENCE: 5

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg

```
                65                  70                  75                  80
Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255

<210> SEQ ID NO 6
<211> LENGTH: 768
<212> TYPE: DNA
<213> ORGANISM: Neisseria meningitidis strain MC58

<400> SEQUENCE: 6
tgcagcagcg agggggtgg tgtcgccgcc gacatcggtg cggggcttgc cgatgcacta      60
accgcaccgc tcgaccataa agacaaaggt ttgcagtctt tgacgctgga tcagtccgtc    120
aggaaaaacg agaaactgaa gctggcggca caaggtgcgg aaaaaactta tggaaacggt    180
gacagcctca atacgggcaa attgaagaac gacaaggtca gccgtttcga ctttatccgc    240
caaatcgaag tggacgggca gctcattacc ttggagagtg gagagttcca agtatacaaa    300
caaagccatt ccgccttaac cgcctttcag accgagcaaa tacaagattc ggagcattcc    360
gggaagatgg ttgcgaaacg ccagttcaga atcggcgaca tagcgggcga acatacatct    420
tttgacaagc ttcccgaagg cggcagggcg acatatcgcg gacggcgtt cggttcagac    480 gatgccggcg gaaaactgac ctacaccata gatttcgccg ccaagcaggg aaacggcaaa    540
atcgaacatt tgaaatcgcc agaactcaat gtcgacctgg ccgccgccga tatcaagccg    600
gatggaaaac gccatgccgt catcagcggt tccgtccttt acaaccaagc cgagaaaggc    660
agttactccc tcggtatctt tggcggaaaa gcccaggaag ttgccggcag cgcggaagtg    720
aaaaccgtaa acggcatacg ccatatcggc cttgccgcca agcaataa                768

<210> SEQ ID NO 7
<211> LENGTH: 254
<212> TYPE: PRT
<213> ORGANISM: Neisseria meningitidis strain 8047

<400> SEQUENCE: 7

Cys Ser Ser Gly Gly Gly Gly Val Ala Ala Asp Ile Gly Ala Arg Leu
1               5                   10                  15
```

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 8
<211> LENGTH: 765
<212> TYPE: DNA
<213> ORGANISM: Neisseria meningitidis strain 8047

<400> SEQUENCE: 8
tgcagcagcg gaggcggcgg tgtcgccgcc gacatcggcg cgaggcttgc cgatgcacta      60
accgcaccgc tcgaccataa agacaaaagt ttgcagtctt tgacgctgga tcagtccgtc     120
aggaaaaacg agaaactgaa gctggcggca caaggtgcgg aaaaaactta tggaaacggc     180
gacagcctca atacgggcaa attgaagaac gacaaggtca gccgcttcga ctttatccgt     240
caaatcgaag tggacgggca gctcattacc ttggagagcg gagagttcca aatatacaaa     300
caggaccact ccgccgtcgt tgccctacag attgaaaaaa tcaacaaccc gacaaaatc      360 gacagcctga taaccaacg ctccttcctt gtcagcggtt tgggcggaga acataccgcc      420
ttcaaccaac tgcctgacgg caaagccgag tatcacggca agcattcag ctccgacgat      480 gctggcggaa aactgaccta taccatagat ttcgccgcca acagggaca cggcaaaatc      540 gaacacctga aacacccga gcaaaatgtc gagcttgccg ccgccgaact caaagcagat      600
gaaaaatcac acgccgtcat tttgggcgac acgcgctacg gcagcgaaga aaaaggcact      660
taccacctcg ccctttttcgg cgaccgcgcc caagaaatcg ccggctcggc aaccgtgaag      720
ataggggaaa aggttcacga aatcggcatc gccggcaaac agtag                      765

<210> SEQ ID NO 9
<211> LENGTH: 254
<212> TYPE: PRT
<213> ORGANISM: Artificial Sequence
<220> FEATURE:
<223> OTHER INFORMATION: aa 27 to 273 of full length fHbp from Neisseria meningitidis strain 8047 with histidine tag

<400> SEQUENCE: 9

```
Met His His His His His His Val Ala Ala Asp Ile Gly Ala Arg Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 10
<211> LENGTH: 762
<212> TYPE: DNA
<213> ORGANISM: Artificial Sequence
<220> FEATURE:
<223> OTHER INFORMATION: nucleic acid sequence for aa 27 to 273 of full length fHbp from Neisseria meningitidis strain 8047 with histidine tag

<400> SEQUENCE: 10

```
atgcatcatc atcaccatca tgttgcagca gatattggtg cacgtctggc agatgcactg      60
accgcaccgc tggatcataa agataaaagc ctgcagagcc tgaccctgga tcagagcgtt     120
cgcaaaaatg aaaaactgaa actggcagca cagggtgcag aaaaaaccta tggtaatggc     180
gatagcctga ataccggcaa actgaaaaat gataaagtga gccgctttga ttttattcgc     240
```

```
cagattgaag ttgatggtca gctgattacc ctggaaagcg gtgaatttca gatttataaa    300
caggatcata gcgcagttgt tgcactgcag attgaaaaaa ttaataatcc ggataaaatt    360
gatagcctga ttaatcagcg tagctttctg gttagcggtc tgggtggtga acataccgca    420
tttaatcagc tgccggatgg taaagcagaa tatcatggca agcctttag ctctgatgat     480 gccggtggta aactgaccta taccattgat tttgcagcca acagggtca tggcaaaatt     540 gaacatctga aacaccgga acagaatgtt gaactggcag cagcagaact gaaagcagat    600 gaaaaagcc atgccgttat tctgggtgat acccgttatg gtagcgaaga aaaaggcacc     660
tatcatctgg cactgtttgg tgatcgtgca caggaaattg caggtagcgc aaccgttaaa    720
attggcgaaa agtgcatga aattggcatt gccggtaaac ag                         762
```

<210> SEQ ID NO 11
<211> LENGTH: 255
<212> TYPE: PRT
<213> ORGANISM: Artificial Sequence
<220> FEATURE:
<223> OTHER INFORMATION: aa 73 to 320 of full length fHbp from Neisseria
       meningitidis strain MC58 with histidine tag

<400> SEQUENCE: 11

```
Met His His His His His His Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255
```

```
<210> SEQ ID NO 12
<211> LENGTH: 765
<212> TYPE: DNA
<213> ORGANISM: Artificial Sequence
<220> FEATURE:
<223> OTHER INFORMATION: nucleic acid sequence for aa 73 to 320 of full
      length fHbp from Neisseria meningitidis strain MC58 with histidine
      tag

<400> SEQUENCE: 12
atgcatcatc atcaccatca tgttgcagca gatattggcg caggtctggc agatgcactg     60
accgctccgc tggatcataa agataaaggt ctgcagagcc tgaccctgga tcagagcgtt    120
cgcaaaaatg aaaaactgaa actggcagca cagggtgcag aaaaaaccta tggtaatggc    180
gatagcctga ataccggcaa actgaaaaat gataaagtga gccgctttga ttttattcgc    240
cagattgaag ttgatggtca gctgattacc ctggaaagcg gtgaatttca ggtgtataaa    300
cagagccata gcgcactgac cgcctttcag accgaacaaa ttcaggatag cgaacatagc    360
ggtaaaatgg ttgccaaacg ccagtttcgt attggtgata ttgccggtga acataccagc    420
tttgataaac tgccggaagg tggtcgtgca acctatcgtg gcaccgcatt tggttctgat    480
gatgccggtg gtaaactgac ctataccatt gattttgcag ccaaacaggg caatggcaaa    540
attgaacatc tgaaatctcc ggaactgaat gttgatctgg cagcagccga tattaaaccg    600
gatggtaaac gccatgcagt tattagcggt agcgtgctgt ataatcaggc agaaaaaggt    660
agctatagcc tgggtatttt tggtggtaaa gcacaggaag ttgcaggtag cgcagaagtt    720
aaaaccgtca acggcattcg tcatattggt ctggcagcga aacag                    765

<210> SEQ ID NO 13
<211> LENGTH: 7
<212> TYPE: PRT
<213> ORGANISM: Neisseria meningitidis (group B)

<400> SEQUENCE: 13

Cys Ser Ser Gly Gly Gly Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Histidine tag

<400> SEQUENCE: 14

Met His His His His His His
1               5

<210> SEQ ID NO 15
<211> LENGTH: 4
<212> TYPE: PRT
<213> ORGANISM: Neisseria meningitidis (group B)

<400> SEQUENCE: 15

Gly Glu His Thr
1

<210> SEQ ID NO 16
<211> LENGTH: 254
<212> TYPE: PRT
<213> ORGANISM: Artificial Sequence
<220> FEATURE:
<223> OTHER INFORMATION: Fusion protein LVL491
```

<400> SEQUENCE: 16

```
Met His His His His His Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 17
<211> LENGTH: 762
<212> TYPE: DNA
<213> ORGANISM: Artificial Sequence
<220> FEATURE:
<223> OTHER INFORMATION: Nucleic acid sequence for fusion protein LVL491

<400> SEQUENCE: 17

```
atgcatcatc atcaccatca tgttgcagca gatattggcg caggtctggc agatgcactg      60
accgctccgc tggatcataa agataaaggt ctgcagagcc tgaccctgga tcagagcgtt     120
cgcaaaaatg aaaaactgaa actggcagca caggtgcaga aaaaaccta tggtaatggc     180
gatagcctga ataccggcaa actgaaaaat gataaagtga gccgctttga ttttattcgc     240
cagattgaag ttgatggtca gctgattacc ctggaaagcg gtgaatttca ggtgtataaa     300
cagagccata gcgcactgac cgcctttcag accgaacaaa ttcaggatag cgaacatagc     360
ggtaaaatgg ttgccaaacg ccagtttcgt attggtgata ttgccggtga acataccgca     420
tttaatcagc tgccggatgg taaagcagaa tatcatggca agcctttag ctctgatgat     480
gccggtggta aactgaccta taccattgat tttgcagcca acaggggtca tggcaaaatt     540
```

```
gaacatctga aaacaccgga acagaatgtt gaactggcag cagcagaact gaaagcagat      600
gaaaaaagcc atgccgttat tctgggtgat acccgttatg gtagcgaaga aaaaggcacc      660
tatcatctgg cactgtttgg tgatcgtgca caggaaattg caggtagcgc aaccgttaaa      720
attggcgaaa aagtgcatga aattggcatt gccggtaaac ag                         762
```

<210> SEQ ID NO 18
<211> LENGTH: 254
<212> TYPE: PRT
<213> ORGANISM: Artificial Sequence
<220> FEATURE:
<223> OTHER INFORMATION: Fusion Protein A

<400> SEQUENCE: 18

```
Met His His His His His Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ala Phe Asn Gln Leu
130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Ala Lys Gly Thr Tyr His Leu Ala
    210                 215                 220

Leu Phe Gly Asp Arg Ala Gln Glu Ile Ala Gly Ser Ala Ala Val Lys
225                 230                 235                 240

Ile Gly Glu Lys Val His Glu Ile Gly Ile Ala Gly Lys Gln
                245                 250
```

<210> SEQ ID NO 19
<211> LENGTH: 765
<212> TYPE: DNA
<213> ORGANISM: Artificial Sequence
<220> FEATURE:
<223> OTHER INFORMATION: Nucleotide sequence for Fusion protein A

<400> SEQUENCE: 19

```
tgcagcagcg agggggtgg tgtcgccgcc gacatcggtg cggggcttgc cgatgcacta      60
accgcaccgc tcgaccataa agacaaaggt ttgcagtctt tgacgctgga tcagtccgtc     120
```

```
aggaaaaacg agaaactgaa gctggcggca caaggtgcgg aaaaaactta tggaaacggt    180
gacagcctca atacgggcaa attgaagaac gacaaggtca gccgtttcga ctttatccgc    240
caaatcgaag tggacgggca gctcattacc ttggagagtg gagagttcca agtatacaaa    300
caaagccatt ccgccttaac cgcctttcag accgagcaaa tacaagattc ggagcattcc    360
gggaagatgg ttgcgaaacg ccagttcaga atcggcgaca tagcgggaga catacccgcc    420
ttcaaccaac tgcctgacgg caaagccgag tatcacggca aagcattcag ctccgacgat    480
gctggcggaa aactgaccta taccatagat ttcgccgcca acagggaca cggcaaaatc    540 gaacacctga aaacccccga gcaaaatgtc gagcttgccg ccgccgaact caaagcagat    600
gaaaaatcac acgccgtcat tttgggcgac acgcgctacg gcagcgaagc aaaaggcact    660
taccacctcg cccttttcgg cgaccgcgcc caagaaatcg ccggctcggc agccgtgaag    720 atagggggaaa aggttcacga aatcggcatc gccggcaaac agtag    765
```

<210> SEQ ID NO 20
<211> LENGTH: 254
<212> TYPE: PRT
<213> ORGANISM: Artificial Sequence
<220> FEATURE:
<223> OTHER INFORMATION: Fusion Protein B

<400> SEQUENCE: 20

```
Met His His His His His Val Ala Ala Asp Ile Gly Ala Gly Leu
 1               5                  10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Ala Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 21
<211> LENGTH: 762
<212> TYPE: DNA
<213> ORGANISM: Artificial Sequence
<220> FEATURE:
<223> OTHER INFORMATION: nucleic acid sequence for Fusion Protein B

<400> SEQUENCE: 21

```
atgcatcatc atcaccatca tgttgcagca gatattggcg caggtctggc agatgcactg      60
accgctccgc tggatcataa agataaaggt ctgcagagcc tgaccctgga tcagagcgtt     120
cgcaaaaatg aaaaactgaa actggcagca cagggtgcag aaaaaaccta tggtaatggc     180
gatagcctga ataccggcaa actgaaaaat gataaagtga gccgctttga ttttattcgc     240
cagattgaag ttgatggtca gctgattacc ctggaaagcg gtgaatttca ggtgtataaa     300
cagagccata gcgcactgac cgcctttcag accgaacaaa ttcaggatag cgaacatagc     360
ggtaaaatgg ttgccaaacg ccagtttcgt attggtgata ttgccggtga acataccgca     420
tttaatcagc tgccggatgg taaagcagaa tatcatggca agcctttag ctctgatgat       480
gccggtggta aactgaccta taccattgat tttgcagcca acagggtca tggcaaaatt       540
gaacatctga aaacaccgga acagaatgtt gaactggcag cagcagaact gaaagcagat     600
gaaaaaagcc atgccgttat tctgggtgat acccgttatg gtagcgaagc aaaaggcacc     660
tatcatctgg cactgtttgg tgatcgtgca caggaaattg caggtagcgc aaccgttaaa     720
attggcgaaa aagtgcatga aattggcatt gccggtaaac ag                         762
```

<210> SEQ ID NO 22
<211> LENGTH: 255
<212> TYPE: PRT
<213> ORGANISM: Artificial Sequence
<220> FEATURE:
<223> OTHER INFORMATION: Fusion protein C

<400> SEQUENCE: 22

```
Met His His His His His His Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ala Phe Asn Gln Leu
    130                 135                 140

Pro Glu Gly Gly Arg Ala Glu Tyr His Gly Lys Ala Phe Ser Ser Asp
145                 150                 155                 160

Asp Ala Gly Gly Lys Leu Thr Tyr Thr Ile Asp Phe Ala Ala Lys Gln
```

165                 170                 175
Gly His Gly Lys Ile Glu His Leu Lys Thr Pro Glu Gln Asn Val Glu
                180                 185                 190

Leu Ala Ala Ala Glu Leu Lys Ala Asp Glu Lys Arg His Ala Val Ile
            195                 200                 205

Leu Gly Asp Thr Arg Tyr Gly Ser Glu Ala Lys Gly Thr Tyr His Leu
        210                 215                 220

Ala Leu Phe Gly Asp Arg Ala Gln Glu Ile Ala Gly Ser Ala Ala Val
225                 230                 235                 240

Lys Ile Gly Glu Lys Val His Glu Ile Gly Ile Ala Gly Lys Gln
                245                 250                 255

<210> SEQ ID NO 23
<211> LENGTH: 765
<212> TYPE: DNA
<213> ORGANISM: Artificial Sequence
<220> FEATURE:
<223> OTHER INFORMATION: Nucleic sequence of Fusion Protein C

<400> SEQUENCE: 23
atgcatcatc atcaccatca tgttgcagca gatattggcg caggtctggc agatgcactg        60
accgctccgc tggatcataa agataaaggt ctgcagagcc tgaccctgga tcagagcgtt       120
cgcaaaaatg aaaaactgaa actggcagca cagggtgcag aaaaaaccta tggtaatggc       180
gatagcctga ataccggcaa actgaaaaat gataaagtga gccgctttga tttattcgc        240 cagattgaag ttgatggtca gctgattacc ctggaaagcg gtgaatttca ggtgtataaa       300
cagagccata gcgcactgac cgcctttcag accgaacaaa ttcaggatag cgaacatagc       360
ggtaaaatgg ttgccaaacg ccagtttcgt attggtgata ttgccggtga acataccgca       420
tttaatcagc tgccggaagg tggtcgtgca gaatatcatg gcaaagcctt tagctctgat       480
gatgccggtg gtaaactgac ctataccatt gattttgcag ccaaacaggg tcatggcaaa       540
attgaacatc tgaaaacacc ggaacagaat gttgaactgg cagcagcaga actgaaagca       600
gatgaaaaac gtcatgccgt tattctgggt gatacccgtt atggtagcga agcaaaaggc       660
acctatcatc tggcactgtt tggtgatcgc gcacaggaaa ttgcaggtag cgcagcagtt       720
aaaattggcg aaaaagtgca tgaaattggc attgccggta acag                       765

<210> SEQ ID NO 24
<211> LENGTH: 255
<212> TYPE: PRT
<213> ORGANISM: Artificial Sequence
<220> FEATURE:
<223> OTHER INFORMATION: Fusion Protein E

<400> SEQUENCE: 24

Met His His His His His Val Ala Ala Asp Ile Gly Ala Gly Leu
1                5                  10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe

```
                85                  90                  95
Gln Val Tyr Lys Gln Ser His Ser Ala Leu Thr Ala Phe Gln Thr Glu
                100                 105                 110

Gln Ile Gln Asp Ser Glu His Ser Gly Lys Met Val Ala Lys Arg Gln
                115                 120                 125

Phe Arg Ile Gly Asp Ile Ala Gly Glu His Thr Ala Phe Asn Gln Leu
                130                 135                 140

Pro Glu Gly Gly Arg Ala Glu Tyr His Gly Lys Ala Phe Ser Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Thr Pro Glu Gln Asn Val Glu
                180                 185                 190

Leu Ala Ala Ala Glu Leu Lys Ala Asp Glu Lys Arg His Ala Val Ile
                195                 200                 205

Leu Gly Asp Thr Arg Tyr Gly Ser Glu Ala Lys Gly Thr Tyr His Leu
                210                 215                 220

Ala Leu Phe Gly Asp Lys Ala Gln Glu Ile Ala Gly Ser Ala Ala Val
225                 230                 235                 240

Lys Ile Gly Glu Lys Val His Glu Ile Gly Ile Ala Gly Lys Gln
                245                 250                 255
```

<210> SEQ ID NO 25
<211> LENGTH: 765
<212> TYPE: DNA
<213> ORGANISM: Artificial Sequence
<220> FEATURE:
<223> OTHER INFORMATION: Nucleic sequence for Fusion Protein E

<400> SEQUENCE: 25

```
atgcatcatc atcaccatca tgttgcagca gatattggcg caggtctggc agatgcactg      60
accgctccgc tggatcataa agataaaggt ctgcagagcc tgaccctgga tcagagcgtt     120
cgcaaaaatg aaaaactgaa actggcagca cagggtgcag aaaaaaccta tggtaatggc     180
gatagcctga ataccggcaa actgaaaaat gataaagtga ccgctttga ttttattcgc      240
cagattgaag ttgatggtca gctgattacc ctggaaagcg tgaatttca ggtgtataaa      300
cagagccata cgcactgac cgcctttcag accgaacaaa ttcaggatag cgaacatagc     360
ggtaaaatgg ttgccaaacg ccagtttcgt attggtgata ttgccggtga acataccgca     420
tttaatcagc tgccggaagg tggtcgtgca gaatatcatg gcaaagcctt tagctctgat     480
gatgccggtg gtaaactgac ctataccatt gattttgcag ccaaacaggg tcatggcaaa     540
attgaacatc tgaaaacacc ggaacagaat gttgaactgg cagcagcaga actgaaagca     600
gatgaaaaac gtcatgccgt tattctgggt gatacccgtt atggtagcga agcaaaaggc     660
acctatcatc tggcactgtt tggtgataaa gcacaggaaa ttgcaggtag cgcagcagtt     720
aaaattggcg aaaaagtgca tgaaattggc attgccggta acag                      765
```

<210> SEQ ID NO 26
<211> LENGTH: 4
<212> TYPE: PRT
<213> ORGANISM: Neisseria meningitidis (group B)

<400> SEQUENCE: 26

Arg Glu Lys Val
1

-continued

```
<210> SEQ ID NO 27
<211> LENGTH: 4
<212> TYPE: PRT
<213> ORGANISM: Neisseria meningitidis (group B)

<400> SEQUENCE: 27

Val Asn Gly Ile
1
```